United States Patent
Stoughton et al.

(10) Patent No.: US 6,859,735 B1
(45) Date of Patent: Feb. 22, 2005

(54) COMPUTER SYSTEMS FOR IDENTIFYING PATHWAYS OF DRUG ACTION

(75) Inventors: Roland Stoughton, San Diego, CA (US); Stephen H. Friend, Seattle, WA (US)

(73) Assignee: Rosetta Inpharmatics LLC, Seattle, WA (US)

( * ) Notice: Subject to any disclaimer, the term of this patent is extended or adjusted under 35 U.S.C. 154(b) by 0 days.

(21) Appl. No.: 09/374,565

(22) Filed: Aug. 13, 1999

Related U.S. Application Data

(62) Division of application No. 09/074,983, filed on May 8, 1998, now Pat. No. 5,965,352.

(51) Int. Cl.[7] .................. G01N 33/48; G01N 33/53; C12Q 1/68; C12P 21/06; G06G 7/48
(52) U.S. Cl. ..................... 702/19; 435/6; 435/7.1; 435/69.1; 703/11
(58) Field of Search ................. 435/6, 69.1, 7.1, 435/4, 91.2; 702/19; 703/11; 536/23.1, 24.3; 720/19, 20

(56) References Cited

U.S. PATENT DOCUMENTS

| | | | |
|---|---|---|---|
| 5,331,573 A | | 7/1994 | Balaji et al. |
| 5,434,796 A | | 7/1995 | Weininger |
| 5,445,934 A | | 8/1995 | Fodor et al. |
| 5,569,588 A | | 10/1996 | Ashby et al. |
| 5,645,988 A | | 7/1997 | Vande Woude et al. |
| 5,657,255 A | | 8/1997 | Fink et al. |
| 5,744,305 A | | 4/1998 | Fodor et al. |
| 5,777,888 A | | 7/1998 | Rine et al. |
| 5,800,992 A | | 9/1998 | Fodor et al. |
| 5,811,231 A | | 9/1998 | Farr et al. |
| 5,930,154 A | * | 7/1999 | Thalhammer-Reyero ..... 703/11 |
| 6,132,969 A | | 10/2000 | Stoughton et al. ............ 435/6 |
| 6,165,709 A | | 12/2000 | Friend et al. .................. 435/4 |
| 2002/0091666 A1 | * | 7/2002 | Rice et al. ..................... 707/1 |
| 2003/0033127 A1 | * | 2/2003 | Lett ............................. 703/11 |
| 2003/0154003 A1 | * | 8/2003 | Eker et al. .................. 700/266 |

FOREIGN PATENT DOCUMENTS

| | | |
|---|---|---|
| EP | 0 816 511 A1 | 1/1996 |
| WO | WO 94/17208 | 8/1994 |
| WO | WO 97/10365 | 3/1997 |
| WO | WO 97/27317 | 7/1997 |
| WO | WO 98/06874 | 2/1998 |

OTHER PUBLICATIONS

Straus and Weiss, 1992, "Genetic evidence for the involvement of the lck tyrosine kinase in signal transduction through the T cell antigen receptor", Cell 70:585–593.

Thomas et al., 1995, "Dynamical behaviour of biological regulatory networks—I. Biological role of feedback loops and practical use of the concept of the loop–characteristic state", Bull. Math. Biol. 57:247–276.

Yuh et al., 1998, "Genomic Cis–regulatory logic: experimental and computational analysis of a sea urchin gene", Science 279:1896–1902.

Velculescu et al., 1995, "Serial analysis of gene expression", Science 270:484–487.

(List continued on next page.)

Primary Examiner—Ardin H. Marschel
(74) Attorney, Agent, or Firm—Jones Day

(57) ABSTRACT

The present invention provides methods and computer systems for identifying and representing the biological pathways of drug action on a cell The present invention also provides methods and computer systems for assessing the significance of the identified representation and for verifying that the identified pathways are actual pathway of drug action. The present invention also provides methods and computer systems for drug development based on the methods for identifying biological pathways of drug action, and methods and computer systems for representing the biological pathways involved in the effect of an environmental change upon a cell.

41 Claims, 12 Drawing Sheets

OTHER PUBLICATIONS

Zhao et al., 1995, "High–density cDNA filter analysis: a novel approach for large–scale, quantitative analysis of gene expression", Gene 156:207–213.
Ecker et al., 1997 "Estimation of the chemosensitizing activity of modulators of multi–drug resistance via combined simultaneous analysis of sigmoidal dose response curve", J. Pharm. Pharmacol. 49:305–309.
Uhlmann et al., 1990, "Antisense oligonucelotides: A new therapeutic principle", Chemical Rev. 90(4):543–584.
Anderson et al., 1994, "Involvement of the protein tyrosine kinase p56$^{lck}$ in T cell signalling and thymocyte development", Adv. Immunol. 56:151–178.
U.S. Appl. No. 09/031,216, filed Feb. 26, 1998, Friend et al.
U.S. Appl. No. 09/099,722, filed Jun. 19, 1998, Stoughton et al.
U.S. Provisional Appl. No. 60/084,742, filed May 8, 1998, Friend et al.
U.S. Provisional Appl. No. 60/090,004, filed Jun. 19, 1998, Friend et al.
U.S. Provisional Appl. No. 60/090,046, filed Jun. 19, 1998, Friend et al.
U.S. Provisional Appl. No. 60/092,512, filed Jul. 13, 1998, Friend et al.
Baudin et al., 1993, "A simple and efficient method for direct gene deletion in Saccharomyces cerevisiae", Nucl. Acids Res. 21:3329–3330.
Belshaw et al., 1996, "Controlling protein association and subcellular localization with a synthetic ligand that induces heterodimerization of proteins", Proc. Natl. Acad. Sci. USA 93:4604–4607.
Biocca, 1995, "Intracellular immunization: antibody targeting to subcellular compartments", Trends in Cell Biology 5:248–253.
Blanchard et al., 1996, "Sequence to array: probing the genome's secrets", Nature Biotechnology 14:1649.
Blanchard et al., 1996, "High–density oligonucleotide arrays", Biosensors & Bioelectronics 11:687–690.
Chee et al., 1996, "Accessing genetic information with high–density DNA arrays", Science 274:610–614.
Cotten and Birnstiel, 1989, "Ribozyme mediated destruction of RNA in vivo", EMBO J. 8:3861–3866.
Dohmen et al., 1994, "Heat–inducible degron: a method for constructing temperature–sensitive mutants", Science 263:1273–1276.
Gari et al., 1997, "A set of vectors with a tetracycline–regulatable promoter system for modulated gene expression in Saccharomyces crevisiae", Yeast 13:837–848.
Goffreau et al., 1996, "Life with 6000 genes", Science 274:546–567.
Gossen and Bujard, 1992, "Tight control of gene expression in mammalian cells by tetracycline–responsive promoters", Proc. Natl. Acad. Sci. USA 89:5547–5551.
Gossen et al., 1995, "Transcriptional activation by tetracyclines in mammalian cells" Science 268:1766–1769.
Guo et al., 1994, "Direct fluorescence analysis of genetic polymorphisms by hybridization with oligonucleotide arrays on glass supports", Nucl. Acids. Res. 22:5456–5465.
Hanke et al., 1996, "Discovery of a novel, potent, and Src family–selective tyrosine kinase inhibitor", J. Biol. Chem. 271:695–701.
Hartwell et al., 1997, "Integrating genetic approaches into the discovery of anticancer drugs", Science 278:1064–1068.

Hayden et al., 1997, "Antibody engineering", Curr, Opin. Immunol. 9:201–212.
Herskowitz, 1987, "Functional inactivation of genes by dominant negative mutations", Nature 329:219–222.
Hoffmann et al., 1997, "A novel tetracycline–dependent expression vector with low basal expression and potent regulatory properties in various mammalian cell lines", Nucl. Acids Res. 25:1078–1079.
Johnston and Davis, 1984, "Sequences that regulate the divergent GAL1–GAL10 promoter in Saccharomyces cerevisiae", Mol. Cell. Biol. 4:1440–1448.
Kerjan et al., 1986, "Nucleotide sequence of Saccharomyces cerevisiae MET25 gene", Nucl. Acids Res. 14:7861–7871.
Lander, 1996, "The new genomics: Global views of biology", Science 274:536–539.
Lennon and Lehrach, 1991, "Hybridization analyses of arrayed cDNA libraries" TIG 7:314–317.
Mascorro–Gallardo et al., 1996, "Construction of a CUP1 promoter–based vector to modulate gene expression in Saccharomyces cerevisiae", Gene 172:169–170.
Matheos et al., 1997, "Tcn1p/Crz1p, a calcineurin–dependent transcription factor that differentially regulates gene expression in Saccharomyces cerevisiae", Genes & Dev. 11:3445–3458.
McAdams and Shapiro, 1995, "Circuit simulation of genetic networks", Science 269:650–656.
Mikulecky, 1990, "Modeling intestinal absorption and other nutrition–related processes using PSPICE and STELLA", J. Ped. Gastroenterol. Nutr. 11:7–20.
Mounts and Liebman, 1997, "Qualitative modeling of normal blood coagulation and its pathological states using stochastic activity networks", Int. J. Biol. Macromolecules 20:265–281.
Mumberg et al., 1994, "Regulatable promoters of Saccharomyces cerevisiae: Comparison of transcriptional activity and their use for heterologous expression", Nucl. Acids. Res. 22:5767–5768.
Nguyen et al., 1995, "Differential gene expression in the murine thymus assayed by quantitative hybridization of arrayed cDNA clones", Genomics 29:207–216.
No et al., 1996, "Ecdysone–inducible gene expression in mammalian cells and transgenic mice", Proc. Natl. Acad. Sci. USA 93:3346–3351.
Nocka et al., 1990, Molecular bases of dominant negative and loss of function mutations at the murine c–kit/white spotting locus: $W_{37}$, $W^v$, $W^{41}$ and $W^{11}$, EMBO J. 9:1805–1813.
Oliff and Friend, 1997, "Cancer, principles & practice of oncology, molecular targets for drug development", Mol. Pharmacol. 68:3115–3125.
Perlmutter and Alberola–lla, 1996, "The use of dominant––negative mutations to elucidate signal transduction pathways in lymphocytes", Curr. Opin. Immunol. 8:285–290.
Polyak et al., 1997, "A model for p53–induced apoptosis", Nature 389:300–306.
Reinitz and Sharp, 1995, "Mechanism of eve stripe formation", Mech. Dev. 49:133–158.
Schena, 1996, "Genome analysis with gene expression microarrays", BioEssays 18:427.
Schena et al., 1996, "Parallel human genome analysis: microarray–based expression monitoring of 1000 genes", Proc. Natl. Acad. Sci. USA 93:10614–10619.

Schena et al., 1995, "Quantitative monitoring of gene expression patterns with a complementary DNA microarray", Science 270:467–470.

Shalon et al., 1996, "A DNA microarray system for analyzing complex DNA samples using two–color fluorescent probe hybridization", Genome Research 639–645.

Shiue, 1997, "Identification of candidate genes for drug discovery by differential display", Drud Dev. Res. 41:142–159.

Shoemaker et al., 1996, "Quantitative phenotypic analysis of yeast deletion mutants using a highly parallel molecular bar–coding strategy", Nature Genetics 14:450–456.

Southern, 1996, "DNA chips: analysing sequence by hybridization to oligonucleotides on a large scale", TIG 12:110–115.

Spencer, 1996, "Creating conditional mutations in mammals", TIG 12:181–187.

Stathopoulos and Cyert,,, 1997, "Calcineurin acts through the CRZ1/TCN1–encoded transcription factor to regulate gene expression in yeast", Genes & Dev. 11:3432–34444.

* cited by examiner

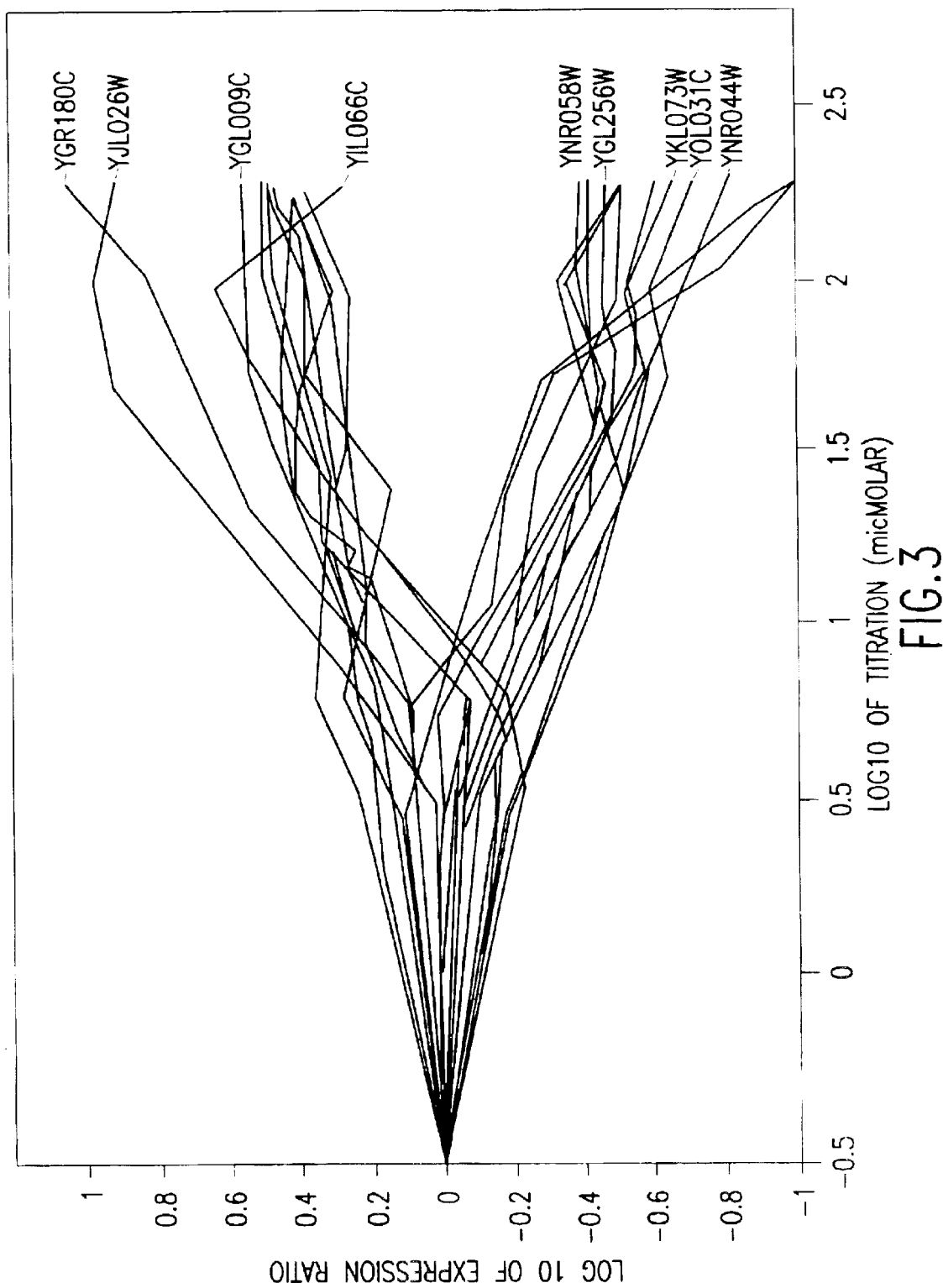

COMPUTER SYSTEMS FOR IDENTIFYING PATHWAYS OF DRUG ACTION

This is a divisional application of U.S. patent application Ser. No. 09/074,983, filed on May 8, 1998, now U.S. Pat. No. 5,965,352, which is incorporated by reference herein in its entirety.

FIELD OF THE INVENTION

The field of this invention relates to methods for characterizing the action of drugs in cells, in particular for finding biological pathways in a cell affected by drug action, as well as application of these methods to drug discovery.

BACKGROUND

The identification of the biological pathway of action of a drug or drug candidate is a problem of great commercial and human importance. Although the primary molecular target of and cellular pathways affected by a drug are often known or suspected because the drug was originally selected by a specific drug screen, it is important to verify its action on such a primary pathway and to quantify its action along other secondary pathways which may be harmful, or may be beneficial, often in unsuspected ways. In other cases, the primary pathways of drug action are unknown, and these must be determined.

This information is important in many areas of practical research, such as, for example, drug discovery, which is a process by which bioactive compounds are identified and preliminarily characterized. Drug discovery is a critical step in the development of treatments for human diseases. Two approaches presently dominate the search for new drugs. The first begins with a screen for compounds that have a desired effect on a cell (e.g., induction of apoptosis), or organism (e.g., inhibition of angiogenesis) as measured in a specific biological assay. Compounds with the desired activity may then be modified to increase potency, stability, or other properties, and the modified compounds retested in the assay. Thus, a compound that acts as an inhibitor of angiogenesis when tested in a mouse tumor model may be identified, and structurally related compounds synthesized and tested in the same assay. One limitation of this approach is that, often, the mechanisms of action, such as the molecular target(s) and cellular pathways affected by the compound, are unknown, and cannot be determined by the screen. In addition, the assay may provide little information about the specificity, either in terms of targets or pathways, of the drug's effect. Finally, the number of compounds that can be screened by assaying biological effects on cells or animals is limited by the required experimental efforts.

In contrast, the second approach to drug screening involves testing numerous compounds for a specific effect on a known molecular target, typically a cloned gene sequence or an isolated enzyme or protein. For example, high-throughput assays can be developed in which numerous compounds can be tested for the ability to change the level of transcription from a specific promoter or the binding of identified proteins. Although the use of high-throughput screens is a powerful methodology for identifying drug candidates, it has limitations. A major drawback is that the assay provides little or no information about the effects of a compound at the cellular or organismal level, in particular information concerning the actual cellular pathways affected. These effects must be tested by using the drug in a series of cell biologic and whole animal studies to determine toxicity or side effects in vivo. In fact, analysis of the specificity and toxicity studies of candidate drugs can consume a significant fraction of the drug development process (see, e.g., Oliff et al., 1997, "Molecular Targets for Drug Development," in DeVita et al. *Cancer: Principles & Practice of Oncology* 5th Ed. 1997 Lippincott-Raven Publishers, Philadelphia).

Several gene expression assays are now becoming practicable for quantitating the drug effect on a large fraction of the genes and proteins in a cell culture (see, e.g., Schena et al, 1995, Quantitative monitoring of gene expression patterns with a complementary DNA micro-array, Science 270:467–470; Lockhort et al., 1996, Expression monitoring by hybridization to high-density oligonucleotide arrays, Nature Biotechnology 14:1675–1680; Blanchard et al., 1996, Sequence to array: Probing the genome's secrets, Mature Biotechnology 14, 1649; 1996, U.S. Pat. No. 5,569,588, issued Oct. 29, 1996 to Ashby et al. entitled "Methods for Drug Screening"). Raw data from these gene expression assays are often difficult to coherently interpret. Such measurement technologies typically return numerous genes with altered expression in response to a drug, typically 50–100, possibly up to 1,000 or as few as 10. In the typical case, without more analysis, it is not possible to discern cause and effect from such data alone. The fact that one or a few genes among many has an altered expression in a pair of related biological states yields little or no insight into what caused this change and what the effects of this change are. These data in themselves do not inform an investigator about the pathways affected or mechanism of action. They do not indicate which effects result from affects on a primary pathway versus which effects are the result of other secondary pathways affected by the drug. Knowledge of all these affected pathways individually is useful in understanding efficacy, side-effects, toxicities, possible failures of efficacy, activation of metabolic responses, and so forth. Further, identification of all pathways of drug action can lead to discovery of alternate pathways suitable to achieve the original therapeutic purpose.

Without effective methods of analysis, one is left to ad hoc further experimentation to interpret such gene expression results in terms of biological pathways and mechanisms. Systematic procedures for guiding the interpretation of such data and such further experimentation, at least in the case of drug target screening, are needed.

Thus, there is a need for improved (e.g., faster and less expensive) methods for characterizing drug activities, and cellular pathways affected by drugs based on effective interpretation of such data as gene expression data. The present invention provides methods for rapidly identifying the molecular targets and pathways affected by candidate drugs and for characterizing their specificity. It further provides methods based on measurement methodologies other than gene expression analysis.

SUMMARY OF THE INVENTION

The invention provides methods for determining the primary and secondary biological pathways through which a drug acts on a cell, and identifying the proteins and genes which are affected via each pathway. The method involves comparing measurements of RNA or protein abundances or activities in response to drug exposure with measurements of RNA or protein abundances or activities in pathways possibly affected by the drug in response to controlled, known perturbations of each pathway. RNA or protein abundances or activities are measured at varying strengths of drug exposure. The known pathway perturbations are controlled to be of varying strengths over a substantial part of the range from pathway inhibition up to pathway saturation.

Additionally, the invention provides methods for verifying likely pathways affected by a drug by comparing measurements of RNA or protein abundances or activities in response to simultaneous drug treatment and controlled pathway perturbation. Further, the invention provides methods for comparing the effects of two different drugs by comparing measurements of RNA or protein abundances in response to exposure to a first drug with RNA or protein abundances in response to exposure to another drug or drugs.

The methods of this invention are based on the discovery that analysis of biological pathways of drug action can be made robust and reliable by utilizing data covering a range of pathway perturbation strengths and drug exposure levels. In general, perturbations of biological pathways and drug exposure levels preferably cover the range from no effects all the way to saturation. In prior methods, such analysis is often based on only two points within these ranges, namely no exposure or perturbation and fully saturating exposure or perturbation. Such limited information leads to less robust and reliable results.

For example, these methods achieve significant benefits and improvements over methods of analysis based merely on use of genetic deletions or over-expression, which typically yield only data for fixed saturating conditions. First, genetic deletions or over-expression strains are not always available for the biological system of interest. Second, use of response data from a range of biological pathway perturbation strengths and drug exposure levels greatly improves the ability to distinguish effects mediated along different pathways. For example, a drug under study may have different potencies along two pathways which converge to affect an overlapping set of genes. Experiments spanning a range of pathway perturbation strengths and drug exposure levels can show that these pathways become effective at different drug exposure levels. On the other hand, data from genetic deletion mutations which completely interrupt each pathway are incapable of resolving such differences in potencies.

In more detail, the present invention provides methods for identifying and representing the biological pathways of drug action on a cell by: (i) measuring responses of cellular constituents to graded exposures of the cell to a drug of interest; (ii) measuring the responses of cellular constituents to perturbations in one or more biological pathways of the cell; and (iii) scaling a combination of the measured pathway responses to fit the measured drug responses best according to an objective measure. In alternative embodiments, the present invention also provides for assessing the significance of the identified representation and for verifying that the identified pathways are actual pathways of drug action. In various embodiments, the responses of cellular constituents can be measured by measuring gene expression (i.e., RNA levels), protein abundances, protein activities, or a combination of such measurements. In various embodiments, perturbation to a biological pathway in the cell can be made by use of titratable expression systems, use of transfection systems, modification to abundances of pathway RNAs, modifications to abundances of pathway proteins, or modifications to activities of the pathway proteins. The present invention also provides methods for drug development based on the methods for identifying biological pathways of drug action.

In a first embodiment, this invention provides a method of representing biological pathways involved in the action of a drug in a cell type comprising: (a) providing a drug response of said drug in said cell type, said drug response having been obtained by a method comprising measuring a plurality of cellular constituents in a cell of said cell type at a plurality of levels of exposure to said drug; (b) representing a model drug response as a combination of one or more biological pathway responses in said cell type, wherein a biological pathway response in said cell type is the product of a method comprising measuring cellular constituents of said biological pathway in a cell of said cell type at a plurality of levels of a perturbation to said biological pathway, and wherein each of said one or more biological pathway responses in said combination are subject to an independent scaling transformation; and (c) determining best scaling transformations of said one or more biological pathway responses which minimize the value of an objective function of the difference between said drug response and said model drug response, whereby said combination of said one or more biological pathways responses subject to said best scaling transformations represents the biological pathways involved in the action of said drug in said cell type.

In a first aspect of the first embodiment, the invention further provides that said determining step further comprises determining an "actual" minimized value of said objective function, and, after said step of determining (i.e., step (c), above), a step of assessing the statistical significance of said best scaling transformations of said one or more biological pathways by a method comprising: (a) obtaining an expected probability distribution of minimized values of said objective function; and (b) assessing the statistical significance of said actual minimum value of said objective function in view of said expected probability distribution of minimum values of said objective function, wherein said actual minimized value of said objective function is the minimized value of said objective function determined from said provided drug response and said model drug response. In this aspect of the first embodiment, the invention further provides that said step of obtaining said expected probability distribution of minimum values of said objective function further comprises the steps of: (a) randomizing said drug response with respect to said plurality of levels of drug exposure and randomizing said model drug response by randomizing said one or more biological pathway responses with respect to said plurality of levels of perturbation to said one or more biological pathways; (b) determining a "theoretical" minimized value of said objective function by finding best scaling transformations of said one or more randomized biological pathway responses which minimize said objective function of the difference between said randomized drug response and said randomized model drug response; and (c) repeating the two previous steps to determine a plurality of theoretical minimum values, said plurality of theoretical minimized values forming said expected probability distribution of minimized values.

In a third aspect of the first embodiment, the invention further provides, after said step of determining, a step of verifying that said one or more biological pathways are biological pathways actually involved in the action of said drug in said cell type by a method comprising: (a) providing combined drug-perturbation responses in said cell type by a method comprising measuring a plurality of cellular constituents in a cell of said cell type exposed simultaneously to one or more levels of said exposure to said drug and to one or more levels of perturbations in said one or more biological pathways; and (b) selecting which of the following model responses behaves most similarly to said combined drug-perturbation responses: (i) a first model response comprising said combination of said one or more biological pathway responses subject to said best scaling transformations evaluated at one or more first sums, each said first sum being the sum of one of said one or more levels of drug exposure subject to said scaling transformations and one of said one or more levels of perturbations to said biological pathways, (ii) a second model response comprising said one or more second sums, each said second sum being the sum of said drug response evaluated at one of said one or more levels of drug exposure and said combination of said one or more biological pathway responses subject to said best scaling transformations evaluated at one of said one or more levels of perturbations to said biological pathways, whereby said one or more biological pathways are verified as biological pathways actually involved in the action of said drug in said cell type if said first model response is selected.

In a fourth aspect of the first embodiment, the invention further provides, after said step of determining, a step of assigning a cellular constituent present in said drug response to the one of said one or more biological pathways in which said biological pathway response of said cellular constituent subject to its best scaling transformation has the greatest correlation with said drug response of said cellular constituent.

In a second embodiment, this invention provides a method of determining a more pathway-specific drug candidate from an initial drug candidate comprising: (a) representing the biological pathways involved in the action of an initial drug candidate by the method of the first embodiment; (b) modifying the structure of said initial drug candidate; (c) representing the biological pathways involved in the action of said modified initial drug candidate by the method of the first embodiment; and (d) determining that said modified initial drug candidate is a more pathway-specific drug candidate than said initial drug candidate if said modified initial drug candidate has fewer biological pathways involved in its action than said initial drug candidate.

In a third embodiment, this invention provides a method of identifying one or more specific biological pathways that are involved in the action of a drug and that mediate side-effects of the drug, said method comprising: (a) carrying out the method of the first embodiment for a first drug; (b) carrying out the method of the first embodiment for a second drug, wherein the first and the second drug are different and exhibit therapeutic efficacy for the same disease or disorder; and (c) identifying those specific biological pathways involved in the action of said first drug that are different from those biological pathways involved in the action of said second drug, thereby identifying one or more specific biological pathways that are involved in the action of said first drug and that mediate side-effects of said first drug.

In a fourth embodiment, this invention provides a method of identifying one or more specific biological pathways that are involved in mediating therapeutic efficacy for a disease or disorder, said method comprising: (a) carrying out the method of the first embodiment for a first drug; (b) carrying out the method of the first embodiment for a second drug, wherein the first and the second drug are different and exhibit therapeutic efficacy for the same disease or disorder; and (c) identifying those specific biological pathways involved in the action of both said first drug and said second drug, thereby identifying one or more specific biological pathways that are involved in the action of said first drug and that mediate therapeutic efficacy for said disease or disorder.

In a fifth embodiment, this invention provides a method for comparing drug responses from two different drugs on a cell type, and thereby measuring the similarity of the effects of the two different drugs on said cell type by: (a) providing a first drug response for a first drug of interest in said cell type, said drug response having been obtained by a method comprising measuring a plurality of cellular constituents in a cell of said cell type at a plurality of levels of exposure to said first drug; (b) providing a second drug response for a second drug of interest in a cell type, said second drug response having been obtained by a method comprising measuring a plurality of cellular constituents in a cell of said cell type at a plurality of levels of exposure to said second drug; and (c) determining best scaling transformation of said second drug response which minimizes the value of an objective function of the difference between said first and second drug responses.

In a sixth embodiment, this invention provides a method of representing biological pathways involved in the effect of an environmental change upon a cell type comprising: (a) providing an environmental response to said environmental change in said cell type, said environmental response having been obtained by a method comprising measuring a plurality of cellular constituents in a cell of said cell type at a plurality of degrees of severity of said environmental change; (b) representing a model environmental response as a combination of one or more biological pathway responses in said cell type, wherein a biological pathway response in said cell type is the product of a method comprising measuring cellular constituents of said biological pathway in a cell of said cell type at a plurality of levels of a perturbation to said biological pathway, and wherein each of said one or more biological pathway responses in said combination are subject to an independent scaling transformation; and (c) determining best scaling transformations of said one or more biological pathway responses which minimize the value of an objective function of the difference between said environmental response and said model environmental response, whereby said combination of said one or more biological pathway responses subject to said best scaling transformations represents the biological pathways involved in the effect of said environmental change upon said cell type.

In a seventh embodiment, this invention provides a computer system for representing biological pathways involved in the action of a drug in a cell type comprising a processor and a memory coupled to said processor, said memory encoding one or more programs, said one or more programs causing said processor to perform a method comprising the steps of: (a) receiving a drug response of said drug in said cell type, said drug response comprising measurements of a plurality of cellular constituents in a cell of said cell type at a plurality of levels of drug exposure; (b) receiving one or more biological pathway responses, each of said one or more biological pathway responses comprising measurements of cellular constituents of said biological pathway in a cell of said cell type at a plurality of levels of a perturbation to said biological pathway; (c) forming a model drug response as a combination of said one or more biological pathway, each of said one or more biological pathway responses in said combination subject to an independent scaling transformation; (d) determining the value of an objective function of the difference between said drug response and said model drug response; and (e) minimizing said determined value of said objective function by varying the scaling transformations of said one or more biological pathway responses to obtain best scaling transformation that minimize said determined value of said objective function; whereby said combination of said one or more biological pathways responses subject to said best scaling transformations represents the biological pathways involved in the action of said drug in said cell type.

BRIEF DESCRIPTION OF THE DRAWINGS

FIG. 3 illustrates response curves of the 30 yeast genes, out of approximately 6000 measured yeast genes, that had the largest expression ratio changes to methotrexate drug exposure; methotrexate exposure levels were 3, 6, 25, 50, 100, and 200 $\mu$m; the 100 $\mu$m titration resulted in a 50% growth defect; responses have been set to zero at the arbitrary abscissa of −0.5.

FIG. 5D illustrates a correlation of the responses illustrated in FIG. 8C to the sum of the response in FIGS. 8A-B.

DETAILED DESCRIPTION

Figure 1:
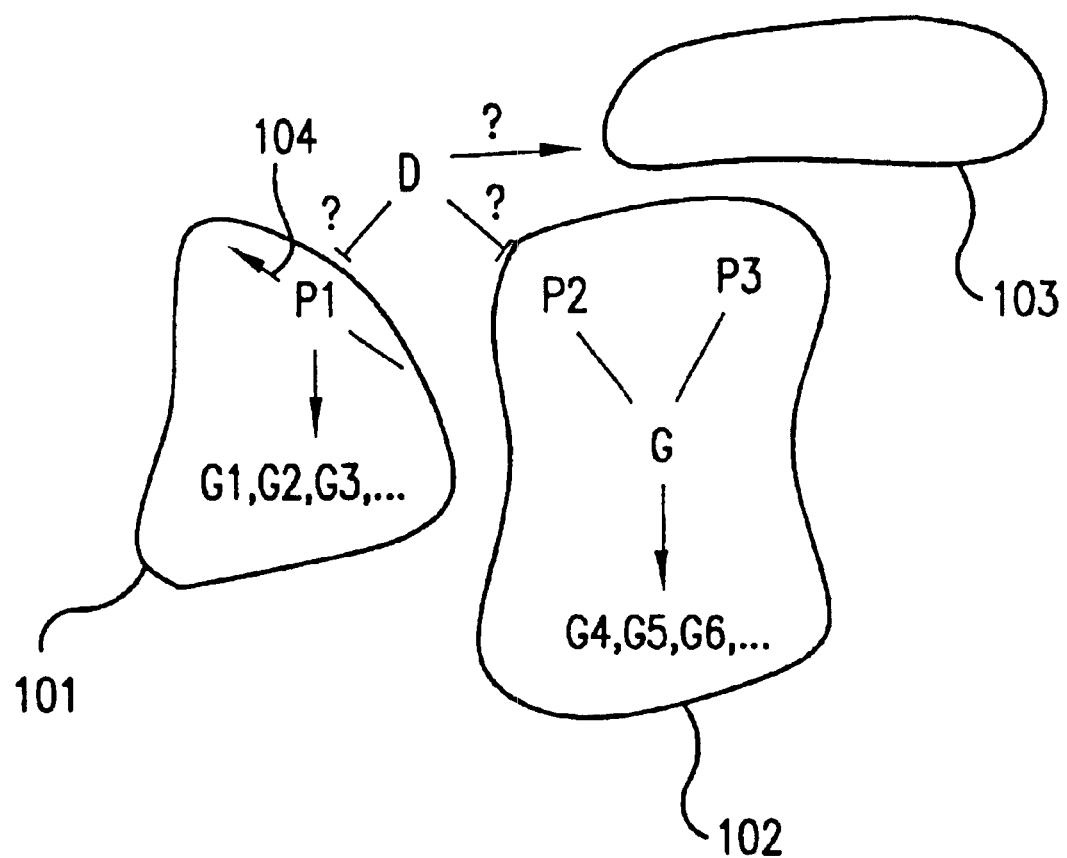
FIG. 1 illustrates exemplary pathways hypothesized for the action of drug D on a biological system.

This section presents a detailed description of the invention and its application to drug discovery. This description is by way of several exemplary illustrations, in increasing detail and specificity, of the general methods of this invention. These examples are non-limiting, and related variants that will be apparent to one of skill in the art are intended to be encompassed by the appended claims. Following these examples are descriptions of embodiments of the data gathering steps that accompany the general methods.

5.1 INTRODUCTION

The invention includes methods for determining the biological pathways through which a drug acts on a biological system (e.g., a cell, or an organism, or a patient). These methods involve comparing measurements of changes in the biological state of a cell in response to graded drug exposure with measurements of changes in the biological state of biological pathways that are likely to be involved in the effects of the drug, the changes being in response to known and graded perturbations of these pathways. Output from this comparison is a representation of the action of the drug on the cell as a combination of independent actions of the drug on each individual biological pathways.

This section first presents certain preliminary concepts including those of drug action, of the biological state of a cell, and of biological pathways, which, according to this invention, represent drug action in a cell. Next, a schematic and non-limiting overview of the methods of this invention is presented. The following sections present the methods of this invention in greater detail.

Although, for simplicity this disclosure often makes reference to single cells (e.g., "RNA is isolated from a cell perturbed at a single gene"), it will be understood by those of skill in the art that more often any particular step of the invention will be carried out using a plurality of genetically similar cells, e.g., from a cultured cell line. Such similar cells are called herein a "cell type". Such cells are either from naturally single celled organisms or derived from multi-cellular higher organisms.

In particular, Section 5.1 describes certain preliminary concepts useful in the further description of this invention. Section 5.2 generally describes the methods of this invention. Section 5.3 describes a preferred analytic embodiment of the methods of this invention. Section 5.4 describes methods of perturbing biological pathways. Section 5.5 describes methods of measuring cellular constituents. Finally, Section 5.6 describes certain exemplary applications of this invention to drug discovery and development.

Drug Action and Biological State

According to the current invention, drugs are any compounds of any degree of complexity that perturb a biological system, whether by known or unknown mechanisms and whether or not they are used therapeutically. Drugs thus include: typical small molecules of research or therapeutic interest; naturally-occurring factors, such as endocrine, paracrine, or autocrine factors or factors interacting with cell receptors of all types; intracellular factors, such as elements of intracellular signaling pathways; factors isolated from other natural sources; and so forth. The biological effect of a drug may be a consequence of, inter alia, drug-mediated changes in the rate of transcription or degradation of one or more species of RNA, the rate or extent of translation or post-translational processing of one or more polypeptides, the rate or extent of the degradation of one or more proteins, the inhibition or stimulation of the action or activity of one or more proteins, and so forth. In fact, most drugs exert their affects by interacting with a protein. Drugs that increase rates or stimulate activities of a protein are called herein "activating drugs," while drugs that decrease rates or inhibit activities of a protein are called herein "inhibiting drugs."

In addition to drugs, this invention is equally applicable to those changes in or aspects of the physical environment that perturb a biological system in targeted manners. Such environmental changes can include moderate changes of temperature (e.g., a temperature elevation of 100° C.) or exposure to moderate doses of radiation. Other environmental aspects include the nutritional environment, such as the presence of only particular sugars, amino acids, and so forth.

The biological effects of a drug (or a physical environmental change) are measured in the instant invention by observations of changes in the biological state of a cell. The biological state of a cell, as used herein, is taken to mean the state of a collection of cellular constituents, which are sufficient to characterize the cell for an intended purpose, such as for characterizing the effects of a drug. The measurements and/or observations made on the state of these constituents can be of their abundances (i.e., amounts or concentrations in a cell), or their activities, or their states of modification (e.g., phosphorylation), or other measurement relevant to the characterization of drug action. In various embodiments, this invention includes making such measurements and/or observations on different collections of cellular constituents. These different collections of cellular constituents are also called herein aspects of the biological state of the cell. (As used herein, the term "cellular constituents" is not intended to refer to known subcellular organelles, such as mitochondria, lysozomes, etc.)

One aspect of the biological state of a cell usefully measured in the present invention is its transcriptional state. The transcriptional state of a cell includes the identities and abundances of the constituent RNA species, especially mRNAs, in the cell under a given set of conditions. Preferably, a substantial fraction of all constituent RNA species in the cell are measured, but at least, a sufficient fraction is measured to characterize the action of a drug of interest. The transcriptional state is the currently preferred aspect of the biological state measured in this invention. It can be conveniently determined by, e.g., measuring cDNA abundances by any of several existing gene expression technologies.

Another aspect of the biological state of a cell usefully measured in the present invention is its translational state. The translational state of a cell includes the identities and abundances of the constituent protein species in the cell under a given set of conditions. Preferably, a substantial fraction of all constituent protein species in the cell are measured, but at least, a sufficient fraction is measured to characterize the action of a drug of interest. As is known to those of skill in the art, the transcriptional state is often representative of the translational state.

Other aspects of the biological state of a cell are also of use in this invention. For example, the activity state of a cell, as that term is used herein, includes the activities of the constituent protein species (and also optionally catalytically active nucleic acid species) in the cell under a given set of conditions. As is known to those of skill in the art, the translational state is often representative of the activity state.

This invention is also adaptable, where relevant, to "mixed" aspects of the biological state of a cell in which measurements of different aspects of the biological state of a cell are combined. For example, in one mixed aspect, the abundances of certain RNA species and of certain protein species, are combined with measurements of the activities of certain other protein species. Further, it will be appreciated from the following that this invention is also adaptable to other aspects of the biological state of the cell that are measurable.

Drug exposure will typically affect many constituents of whatever aspect of the biological state of a cell is being measured and/or observed in a particular embodiment of this invention. For example, as a result of regulatory, homeostatic, and compensatory networks and systems known to be present in cells, even an "ideal drug," i.e., a drug that directly affects only a single constituent in a cell, and without direct effects on any other constituent, will have complicated and often unpredictable indirect effects. Consider, for example, a drug that specifically and completely inhibits activity of a single hypothetical protein, protein P. Although the drug itself will directly change the activity of only protein P, additional cellular constituents that are inhibited or stimulated by protein P, or which are elevated or diminished to compensate for the loss of protein P activity will also be affected. Still other cellular constituents will be affected by changes in the levels or activity of the second tier constituents, and so on. Therefore, the direct effect of the drug on its target, protein P, is hidden in the large number of indirect effects downstream from protein P. Such downstream effects of protein P are called herein the biological pathway originating at protein P (see below).

Accordingly, a drug that is not ideal, e.g., one that directly affects more than one molecular target, may have still more complicated downstream effects. In one aspect, according to the present invention, the analysis of these effects provides considerable information about the drug including, for example, identification of biological pathways effected by the drug and which explain its action and side effects of toxicities in the cell. In a related aspect, the present invention provides methods for carrying out this analysis.

Measurement of the transcriptional state of a cell is preferred in this invention, not only because it is relatively easy to measure but also because, although a drug may act through a post-transcriptional mechanism (such as inhibition of the activity of a protein or change in its rate of degradation), the administration of a drug to a cell almost always results in a measurable change, through direct or indirect effects, in the transcriptional state. A reason that drug exposure changes the transcriptional state of a cell is because the previously mentioned feedback systems, or networks, which react in a compensatory manner to infections, genetic modifications, environmental changes, including drug administration, and so forth, do so primarily by altering patterns of gene expression or transcription. As a result of internal compensations, many perturbations to a biological system, although having only a muted effect on the external behavior of the system, can nevertheless profoundly influence the internal response of individual elements, e.g., gene expression, in the cell.

Biological Pathways

In the instant invention, drug effects on a cell, whether an ideal or a non-ideal drug and however measured in a particular implementation, are represented by combining the effects of the drug on individual biological pathways. For example, FIG. 1 illustrates that drug D acts on a cell by interacting with biological pathways 101, 102, and 103 (details of pathway 103 are not illustrated). The arcs between drug D and these pathways represent possible action of drug D on these pathways. The entire action of drug D on the cell is assumed to be expressible as a combination of drug D's actions on one or more of these three pathways. In the following paragraphs, first, biological pathways as generally used according to this invention are described, followed by description of particular biological pathways to which this invention is advantageously applied.

As used herein, a biological pathway is generally understood to be a collection of cellular constituents related in that each cellular constituent of the collection is influenced according to some biological mechanism by one or more other cellular constituents in the collection. The cellular constituents making up a particular pathway can be drawn from any aspect of the biological state of a cell, for example, from the transcriptional state, or the translational state, or the activity state, or mixed aspects of the biological state. Therefore, cellular constituents of a pathway can include mRNA levels, protein abundances, protein activities, degree of protein or nucleic acid modification (e.g., phosphorylation or methylation), combinations of these types of cellular constituents, and so forth. Each cellular constituent of the collection is influenced by at least one other cellular constituent in the collection by some biological mechanism, which need not be specified or even understood. In illustrations presented herein, the influence, whether direct or indirect, of one cellular constituent on another is presented as an arc between the two cellular constituents, and the entire pathway is presented as a network of arcs linking the cellular constituents of the pathway. A biological pathway, therefore, refers both to the collection of cellular constituents drawn from some aspect of the biological state together with the network of influences between the constituents.

For example, in FIG. 1, biological pathway 101 includes protein P1 (for example, either the abundance or activity of P1) and genes G1, G2, and G3 (for example, their transcribed mRNA levels) together with the influence, direct or indirect, of protein P1 on these three genes, represented as the arc leading from P1 to these three genes. The mechanism of this influence might arise, for example, because protein P1 can bind to promoters of these genes and increase the abundance of their transcripts.

Concrete examples of biological pathways, as understood herein, are well known in the art. They depend on various biological mechanisms by which the cellular constituents influence one another. For example, biological pathways include well-known biochemical synthetic pathways in which, for example, molecules are broken down to provide cellular energy or built up to provide cellular energy stores, or in which protein or nucleic acid precursors are synthesized. The cellular constituents of synthetic pathways include enzymes and the synthetic intermediates, and the influence of a precursor molecule on a successor molecule is by direct enzyme-mediated conversion. Biological pathways also include signaling and control pathways, many examples of which are also well known. Cellular constituents of these pathways include, typically, primary or intermediate signaling molecules, as well as the proteins participating in the signal or control cascades usually characterizing these pathways. In signaling pathways, binding of a signal molecule to a receptor usually directly influences the abundances of intermediate signaling molecules and indirectly influences on the degree of phosphorylation (or other modification) of pathway proteins. Both of these effects in turn influence activities of cellular proteins that are key effectors of the cellular processes initiated by the signal, for example, by affecting the transcriptional state of the cell. Control pathways, such as those controlling the timing and occurrence of the cell cycle, are similar. Here, multiple, often ongoing, cellular events are temporally coordinated, often with feedback control, to achieve a consistent outcome, such as cell division with chromosome segregation. This coordination is a consequence of functioning of the pathway, often mediated by mutual influences of proteins on each other's degree of phosphorylation (or other modification). Also, well known control pathways seek to maintain optimal levels of cellular metabolites in the face of a fluctuating environment. Further examples of cellular pathways operating according to understood mechanisms will be known to those of skill in the art.

Pathways of particular interest in this invention are defined as those that "originate" at particular cellular constituents, especially hierarchical pathways that originate at particular cellular constituents. A pathway originating at particular cellular constituents includes those particular cellular constituents, a second group of cellular constituents that are directly influenced by the particular cellular constituents, a third group of cellular constituents that are directly influenced by the second group of cellular constituents, and so forth, along with the network of influences between the groups of cellular constituents. Influences between the cellular constituents can be according to any biological mechanism, for example, a signaling mechanism, or a regulatory or homeostatic control mechanism, or a synthetic mechanism. In FIG. 1, pathway 101, including a protein and several genes, originates at protein P1. Pathway 102, including two proteins and several genes, originates at proteins P2 and P3.

Biological pathways can also be either hierarchical or non-hierarchical. Generally, a hierarchical biological pathway has no feedback loops. In more detail, a hierarchical pathway is one in which its cellular constituents can be arranged into a hierarchy of numbered levels so that cellular constituents belonging to a particular numbered level can be influenced only by cellular constituents belonging to levels of lower numbers. A hierarchical pathway originates from the lowest numbered cellular constituents. In FIG. 1, pathways 101 and 102 are hierarchical. Pathway 101 is clearly hierarchical. In pathway 102, proteins P2 and P3, on a lowest numbered level, both (directly) affect gene G, on an intermediate numbered level. In turn, gene G (perhaps indirectly) affects genes G4, G5, and G6, all on a highest numbered level. In contrast, a non-hierarchical pathway has one or more feedback loops. A feedback loop in a biological pathway is a subset of cellular constituents of the pathway, each constituent of the feedback loop influences and also is influenced by other constituents of the feedback loop. For example, in pathway 102 of FIG. 1, if gene G6 (perhaps indirectly) affected protein P3, a feedback loop including genes G and G6 and protein P3 would be created.

In summary, therefore, as used herein, a biological pathway includes a collection of cellular constituents that influence one another through any biological mechanism, known or unknown, such as by a cell's synthetic, regulatory, homeostatic, or control networks. The influence of one cellular constituent on another can be, inter alia, by a synthetic transformation of the one cellular constituent into the other, by a direct physical interaction of the two cellular constituents, by an indirect interaction of the two cellular constituents mediated through intermediate biological events, or by other mechanisms. Further, certain pathways that are of particular interest in this invention can be said to originate at particular cellular constituents, which influence, but are not in turn influenced by, the other cellular constituents in the pathway and among such pathways, those without feedback loops are said to be hierarchical.

Because this invention is directed to representing drug action by combinations of biological pathways, certain types of pathways are of particular interest. Drugs typically act on a cell by directly interacting with one cellular constituent, and more usually with a plurality of 5 to 10 to 50 or more cellular constituents. Such cellular constituents are called herein the "targets" of the drug. Further effects of the drug on the cell flow from the other cellular constituents influenced, directly or indirectly, by the direct targets of the drug. Therefore, pathways of interest in this invention for representing drug action include those that originate at particular cellular constituents, and especially, are hierarchical. In particular, the originating cellular constituents are preferably those that are potential drug targets. Since most drug targets are proteins, in particular, pathways originating at cellular proteins are of especial interest in representing drug action. Hierarchical pathways are advantageous in representing drug action, because the feedback loops present in non-hierarchical pathways can obscure drug effects by causing compensating influences in cellular constituents that mute drug influences.

The following descriptions of the various embodiments of this invention, for economy of language only and without any limitation, are primarily directed to pathways, and often only to hierarchical pathways, originating at particular proteins. In view of the following description, it will be apparent to one of skill in the art how to apply the invention to pathways, including non-hierarchical pathways, originating at other cellular constituents, such as mRNA abundances.

Identification and Perturbation of Biological Pathways

Biological pathways, especially pathways that originate at proteins or that are hierarchical, can be identified for use in this invention by several means, including by use of known pathways and by measurements of aspects of the biological state of a cell. A known pathway, such as one of the exemplary types of pathways mentioned above, often includes known active proteins (or other types of cellular constituents) which may be drug targets. This entire known pathway can be used to represent drug action. Alternatively, parts (also called herein "sub-pathways") of such a known pathway can be used in this invention. For example, sub-pathways originating from any one or more of these known proteins (or other cellular constituents likely to be drug targets) include pathway constituents directly or indirectly influenced by the one or more known proteins (and excluding pathway constituents influencing these one or more proteins). A plurality of sub-pathways can be derived from a single known pathway. One or more of these sub-pathways can be used to represent drug action in the methods of this invention.

Biological pathways for use in this invention can also be identified in sufficient detail by measurements of aspects of the biological state of a cell, for example, by measurements of the transcriptional state, or of the translational state, or of the activity state, or of mixed aspects of the biological state. By measurements of an aspect of the biological state of a cell subject to various perturbing conditions, such as conditions resulting from exposure to various drugs or from various genetic manipulations, collections of cellular constituents that vary in a correlated fashion can be identified. Correlated variation means herein that the relative variation of the cellular constituents in the collection, in other words the pattern of variation of the cellular constituents, is similar in the different conditions. A network of mutual influences linking the collection of constituents into a biological pathway can be inferred from the similar pattern of variations in different conditions. When the various conditions during measurement act on the biological pathway, the constituents of the pathway respond with similar patterns of variation determined by the type and direction of their mutual influences. Even if neither the exact network of influences nor the mechanism of their action is known, this collection of constituents can be used as one biological pathway in this invention.

For example, a drug known to act at a single defined target can be used to measure the pathway originating from this target. A cell is exposed to varying concentrations of the drug and the cellular constituents of an aspect of the biological state, for example, the transcriptional state, are measured. Those cellular constituents that vary in a correlated pattern as the concentrations of the drug are changed can be identified as a pathway originating at that drug.

Additionally, as in the case of already known pathways, sub-pathways of a measured pathway can be determined if measurement during exposure to further conditions reveals that sub-collections of the original pathway vary according to different patterns. These differently varying sub-collections then constitute sub-pathways applicable in this invention. Cellular constituents of the measured pathway can be grouped according to the sub-pathway through which they are most affected.

For example, where a pathway has been identified by measurements of a cell exposed to varying concentrations of a drug, sub-pathways can be identified by performing gene knockouts on the cell. By measuring, e.g., the transcriptional state of a cell exposed to the drug and having certain gene knockouts, sub-pathways of the drug pathway originating at the deleted gene can be identified.

FIG. 3 illustrates an example of a pathway identified by measurement. This figure illustrates mRNA expression levels of 30 genes of the yeast *saccharomyces cerevisiae* that, of the approximately 6000 genes in the genome of this yeast, had the largest expression changes in response to six different titrations of the drug methotrexate. These gene expression level measurements were made with gene transcript arrays as described in Section 5.4. Each of these 30 genes exhibited a correlated variation in response to exposure to various concentrations of methotrexate, in that each gene exhibited either a uniform increase or decrease from a native abundance to a saturation abundance in response to increasing concentrations of methotrexate. Accordingly, these 30 genes can be employed in this invention as a pathway, which encompasses cellular constituents of the transcriptional state influenced by methotrexate. Additionally, if exposure to further conditions, such as to different drugs or to drug knockouts, reveals additional patterns of behavior, then this group of 30 genes may be subdivided into yet additional sub-pathways.

The methods of this invention employ measurements of graded perturbations of biological pathways. They compare measurements of graded perturbations of pathways likely to be relevant to the action of a drug with measurements of graded exposure of a cell to the drug in order to identify pathways actually involved in action of the drug. Graded pathway perturbations can be performed in several manners. In the case of known or measured pathways which originate from known proteins (or other cellular constituents), the abundance or activity of these proteins (or other cellular constituents) can be perturbed in a graded manner by methods such as mutation, transfection, controllable promoter systems, or other drugs of specific known action. These methods are described in more detail in described in Section 5.4.

Graded perturbations to the originating cellular constituents will be propagated to other cellular constituents of the pathway by means of the network of influences defining the pathway. The response data consist of, inter alia, gene transcript or protein abundance measurements for the genes or gene products in the affected pathway. Response data can be measured by methods described in more detail subsequently in Sections 5.5.

In the case of pathways defined by measurement, it is particularly advantageous if the constituents from which the pathway originates are identified. In that case, these originating constituents can be perturbed as described for known pathways. If the originating constituents are not identified, the conditions defining the pathway can be manipulated in a graded fashion. For example, in a pathway one of whose defining conditions is drug exposure, the drug exposure can be graded and the cellular constituents observed. If the defining conditions involve genetic manipulation, the genetic manipulation can be performed in a graded manner according to methods to be described in Section 5.4.

5.2 Decomposing Drug Responses into Pathway Contributions

This section presents, first, an overview of the methods of this invention, and second, an extended illustrative example of the principal of these methods.

Overview of the Methods of this Invention

The methods of this invention determine the biological pathways through which a drug acts on a biological system by comparing measurements of changes in the biological state of a cell in response to graded drug exposure with measurements of changes in the biological state of biological pathways that are likely to be involved in the effects of the drug, the changes being in response to graded perturbations of these pathways.

Aspects of the biological state of a cell, for example, the transcriptional state, the translational state or the activity state, are measured (as described in Section 5.6) in response to a plurality of strengths of drug exposure, preferably graded from drug absence to full drug effect. The collection of these measurements, optionally graphically presented, are called herein the "drug response". Pathway perturbations useful in this invention can be graded in varying strengths over a substantial part of the range from complete pathway inhibition up to full pathway saturation. Aspects of the biological state of a cell which are similar to those measured in the drug response, e.g., the transcriptional state, are measured in response to a plurality of graded pathway perturbation strengths. The collection of these measurements, optionally graphically presented, are called herein the "pathway response" or "pathway signature". The pathway responses are preferably measured in experiments in which the activity or abundance of the leading protein or gene in the pathway is changed.

Cellular constituents varying in the drug response are compared to cellular constituents varying in the pathway responses in order to find that biological pathway, or combination of biological pathways, which matches all or substantially all of the drug response. Substantially all of a drug response is matched by pathway responses when most of the cellular constituents varying in the drug response are found to vary in a similar fashion in one or more of the pathway responses. Preferably, at least 75% of the cellular constituents varying in the drug response can be matched, more preferably at least 90% can be so matched, and even more preferably at least 95% can be so matched. Cellular constituents vary in a similar fashion in two responses when both sets of data are likely to be the same in view of experimental error.

In a preferred embodiment, comparison of a drug response with one or more pathway responses is performed by a method in which an objective measure of differences between the measured drug response and a model drug response is minimized. The model drug response is constructed by combining the pathway responses of those pathways considered likely to be involved in the effects of the drug. If a particular cellular constituent varies in only one pathway response, the variation of that cellular constituent in the model drug response is the variation in that one pathway response. If a particular cellular constituent varies in two or more pathway responses, the variation of that cellular constituent in the model drug response is a combination of the variation in the pathway responses. This combination can be performed additively or by another numerical combination (see Section 5.3). Since the relation of the strength of the drug (described, for example, by the kinetic constants describing its actions) to the effectiveness of the graded pathway perturbation (described, for example, by arbitrary measures of a perturbation control parameter) is not known, an adjustable scaling is made between the intensity of the graded perturbations for each pathway response that are combined in the model drug response and the graded drug exposures. The variations of the cellular constituents are combined together into the model drug response with adjustable scalings. The adjustable scaling for one pathway is usually independent of the scalings for the other pathways.

In one embodiment, the objective measure can be minimized by adjusting the scaling of each pathway response in the model drug response and/or by varying the number or identity of biological pathways combined in the model drug response. Varying the pathways combined in the model drug response can be simply achieved by setting the adjustable scalings in the biological pathways not desired so that no variation in the cellular constituents occurs. In a preferred embodiment, where the adjustable scalings are performed by linear transformation between the pathway perturbation parameters and the drug exposure, minimization of the objective measure can be performed by standard techniques of numerical analysis. See, e.g., Press et al., 1996, *Numerical Recipes in C*, 2nd Ed. Cambridge Univ. Press, Ch. 10.; Branch et al., 1996, *Matlab Optimization Toolbox User's Guide*, Mathworks (Natick, Mass.). Also, the method of numerically combining variations of the same cellular constituent from different pathways can be varied. For example, multiplicative cross-product terms could be included which would represent, inter alia, multiplicative responses from multiple transcription factors coming together from different convergent pathways to form a transcription complex.

The pathways combined in the model drug response in order to represent measured drug response in advance of minimization of the objective function can be chosen in various ways. Most simply a large collection of biological pathways covering many cellular functions can be combined with independently adjustable scalings; the objective measure minimized; and the combination of biological pathways best representing the drug response determined. A "compendium" of biological pathways is a set of pathways which is substantially complete in the biological system used for the assay, or at least sufficiently complete to cover all pathways likely to be relevant for drug action. Preferably, the minimization is made more efficient if the collection of pathways can be narrowed to those likely to be involved in the action of the drug. Such narrowing can be predicated on, for example, prior knowledge of drug effect and biological pathway significance.

More preferably, pathways are selected that originate at particular cellular constituents, and advantageously, are also hierarchical (minimizing the muting effects of negative feedback loops or the amplifying effects of positive feedback loops). Most preferably, the originating cellular constituents are likely to be targets of the drug of interest, usually functionally active proteins. For example, given a drug of interest and a selection of potential targets in the cell, first, the biological pathways originating at each of the potential targets can be measured (as previously described in Section 5.1). Second, these pathways can be combined with independent scaling factors, the objective measure minimized, and the combination of pathways best representing the drug's action determined. Thereby, along with determination of the actual pathways involved in drug action, the actual targets of the drug are also identified as the cellular constituents from which the actual pathways originate.

After the pathways involved in drug action are determined, they can be confirmed by the following additional methods of this invention. According to a first confirmation method, the significance of the pathways determined is decided based on statistical tests referencing the minimum value computed from the objective measure. One preferred test computes pathway representations as above with a plurality of randomizations of the drug response data in order to determine a distribution of minimum values of the objective measure. The statistical significance of the minimum value of the objective measure actually obtained from the un-randomized drug response data can be judged against this distribution.

According to a second confirmation method, determined pathways can be confirmed by making measurements of a cell simultaneously both exposed to the drug and also having one or more of the determined pathways perturbed. By perturbing drug exposed cells (or drugging perturbed cells), verification can be obtained that the pathway is in fact involved in the response of specific downstream genes and proteins. If the biological pathways perturbed are not involved in the action of the drug, the drug and the perturbations will produce independent, usually substantially additive, effects on the variation of cellular constituents. If the biological pathways perturbed are indeed involved in the action of the drug, the effects of the drug and the perturbations will not be independent. The effects will interfere and the variation of cellular constituents will saturate at values observed for either drug exposure or pathway perturbations alone.

Illustration of the Methods of this Invention

The following paragraphs generally illustrate several of the methods of this invention with respect to FIG. 1 and FIGS. 2A–C. FIG. 1 illustrates drug D that may act on a cell through three potential pathways. Pathways 101 and 102 originate with proteins P1 and P2 and P3, respectively, and ultimately influence the expression levels of the indicated genes, perhaps by influencing additional mediating cellular constituents. The details of pathway 103 are not illustrated. The methods of this invention determine which of these three pathways, alone or in some combination, explains the actual action of drug D on the cell To make this determination, the methods of this invention attempt to represent drug D's action on the cell, that is its drug response, by a combination of the pathway responses of pathways 101, 102, and 103. This representation will be successful, and drug D's response will be adequately represented, for that combination of pathways which drug D actually effects. If the observed response of drug D can be represented adequately by only one of the pathway responses, that pathway is identified as being the only pathway of action for drug D.

In the case of pathways 101 and 102 which originate at proteins P1 and P2 and P3, respectively, the pathway responses can be directly determined by known perturbations of the abundance, or activity, or some other characteristic relevant for drug D's action, of the originating proteins. For example, application of variable perturbation 104 changes a relevant characteristic of protein P1, thereby influencing characteristics of the other cellular constituents in pathway 101, for example, the expression levels of genes G1, G2, and G3. Perturbation 104 is capable of being applied in a graded fashion in order to generate pathway responses at a plurality of perturbation control values, from the native level of the characteristic of protein P1 perturbed to full saturation or inhibition of that characteristic. Similar known perturbations can be made to protein P2 and the expression levels of genes G4, G5, and G6 measured.

Additionally, if the response of drug D on a cell can be represented as pathway responses generated by perturbing P1 or P2, one of skill on the art will appreciate that these P1 or P2 are thereby identified as protein targets of drug D.

Figure 2A:
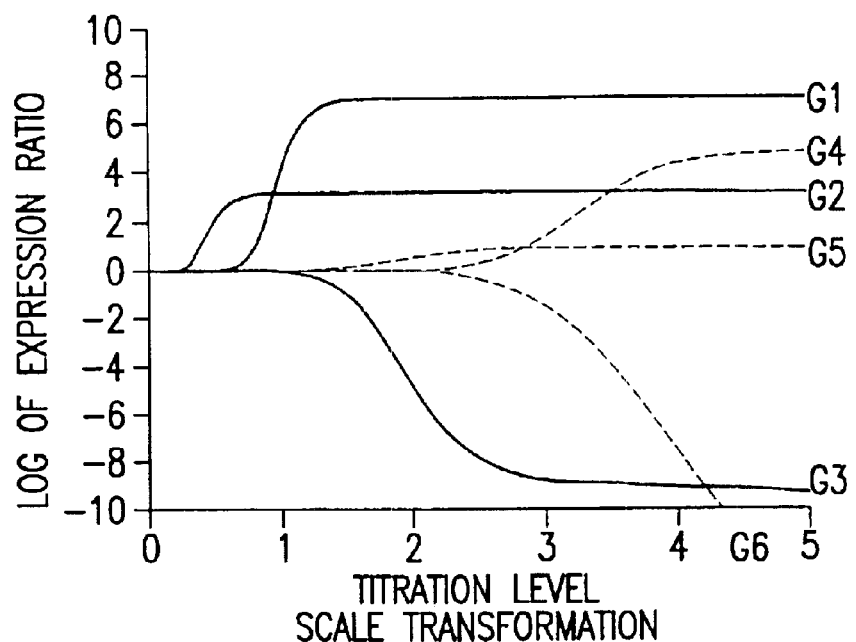
FIG. 2A illustrates exemplary responses of expression of genes G1, G2, and G3 in the biological system of FIG. 1 to exposure to drug D (values are normalized to untreated value)

FIG. 2A illustrates a possible transcriptional response of a cell to drug D. The horizontal axis indexes the degree of drug exposure, for example, the concentration of the drug in the cell's environment, ranging from no exposure at the value 0 to saturating exposure at the value 5. The vertical axis indexes the logarithm of the ratio of the gene expression on exposure to drug D to the gene expression in the absence of drug D. Accordingly, the drug response curves all begin at 0 in the absence of drug D, corresponding to an expression ratio of 1. It is assumed for the purposes of this example that only genes G1, G2, and G3 of a cell significantly respond to exposure to drug D with the response indicated by the labeled response curves.

Although the gene response curves are presented for the purposes of illustration as continuous curves, in an actual experimentally determined drug response, expression ratios are measured for only a limited set of discrete levels of drug exposure. In an actual case, the graphical representation of a drug response would consist of expression ratios only at these discrete exposure levels. Preferably, the discrete drug exposure levels are chosen and positioned so that the steepest regions of the drug response curves are adequately sampled. Preferably, at least 5 and more preferably 10 or more exposure levels are positioned in these regions of the response curves, where the drug response varies from the unexposed level to the saturating level.

Such response curves can be generated and measured by the methods of Sections 5.5. In particular, by employing technologies for gene expression analysis in concert with the genome sequence of the yeast S. cerevisiae, such response curves can be experimentally generated for nearly all of the genes in that yeast. Although much of the description of this invention is directed to measurement and modeling of gene expression data, this invention is equally applicable to measurements of other aspects of the biological state of a cell, such as protein abundances or activities.

Figure 2B:
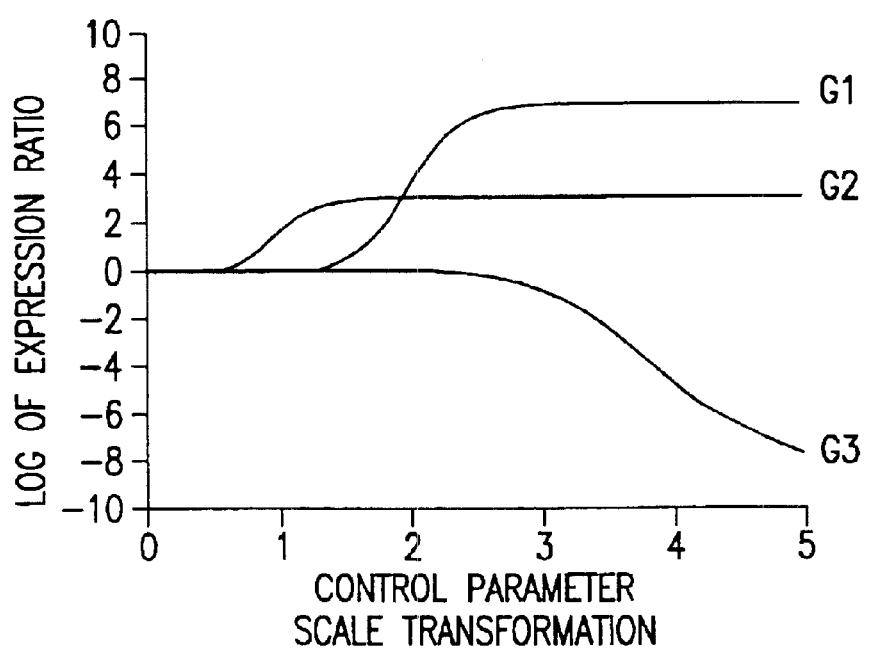
FIG. 2B illustrates exemplary responses of genes G1, G2, and G3 in pathway originating at protein P1 to graded perturbations of P1.

FIG. 2B illustrates a possible pathway response for pathway 101 (in FIG. 1), which originates with protein P1 and involves the expression levels of genes G1, G2, and G3, in response to perturbation 104 to originating protein P1. The horizontal axis in this figure indexes the strength of perturbation 104 applied to P1, ranging from no perturbation of P1 at the value 0 to saturating perturbation of P1 at the value 5. Perturbation 104 can be either inhibiting or activating protein P1 as the case may be. As set out in more detail in Section 5.4, such perturbation might be accomplished, inter alia, by transfection with varying amounts of a gene expressing P1 in order to increase the abundance of P1, or by expression of P1 under the control of a controllable promoter in turn controlled by a drug or small molecule, or by inhibition of P1 activity by exposure to a different drug of specific known action against P1. Similarly to FIG. 2A, the vertical axis in FIG. 2B indexes the logarithm of the ratio of the gene expression on exposure to perturbation 104 to the gene expression in the absence of perturbation 104. The response of the expression levels of genes G1, G2, and G3, which are components of pathway 101 influenced by protein P1 (whether directly or indirectly), are illustrated by the labeled curves.

Also similarly to FIG. 2A, although these pathway response curves are illustrated as continuous, in actual fact perturbation 104 to protein P1 would be applied at a limited set of discrete values and the "curves" are actually expression ratio values at these discrete perturbation control parameter values. Also preferably, the discrete perturbation values are chosen and positioned so that the steepest regions of the pathway response curves are adequately sampled, with at least 5 and more preferably 10 or more perturbation control parameter values positioned in the regions of the response curves where the responses vary from the unexposed level to the saturating level.

The drug and pathway response curves in FIGS. 2A and 2B illustrate the generally expected shape of such curves. This expected shape includes a below threshold region at low drug exposure or perturbation control parameter over which there is effectively no response of the cellular constituents in the pathway. After this below threshold region, the drug or perturbation begins to be efficacious and the values of characteristics of the cellular constituents are perturbed. The curve of perturbed values is expected to usually have a monotonic increase or decrease toward an asymptotic level at saturation beyond which no further change is observed. The response curves terminate in this saturation region.

In fact, more complicated, non-monotonic response curve shapes are possible and expected in some situations. For example, in the case where the drug or the perturbation has toxic effects, as toxicity sets in rising abundances of cellular constituents may start to fall and falling abundances may start to fall even faster. Also, nonlinear and feedback mechanisms known to be present in the biological systems may result in non-monotonic, multi-phasic responses. Such a response might first increase and then decrease with increasing perturbation amplitude or drug exposure. For example, a drug or a perturbation may act on certain cellular constituents through two pathways with different thresholds and with opposite effects to generate increasing then decreasing (or vice versa) responses. Although the methods of this invention are illustrated and primarily described with respect to monotonic response curves, such as illustrated FIGS. 2A-B, as will be apparent to one of skill in the art from subsequent description, these methods are equally applicable to non-monotonic response curves.

Having measured drug and pathway responses, the problem of determining the pathways by which drug D (of FIG. 1) acts on a cell requires matching the drug response as a combination of pathway responses. FIG. 2A illustrates how the abundances of genes G1, G2, G3, G4, G5, and G6 vary in the drug response of drug D. Since these same genes vary in the disjoint pathways originating at P1 and P2, it can be determined according to the methods of this invention whether either of these two pathway is actually involved in the response of drug D.

According to the methods of this invention, these determinations are made by inquiring whether the pathway response curves of the pathways originating at P1 and P2 can be transformed to match the drug response curves of FIG. 2A. Concerning only the pathway originating at protein P1, the determination of whether this pathway is actually involved in the action of drug D is met by attempting to transform the pathway response curves of this pathway, illustrated in FIG. 2B, into the drug response curves for G1, G2, and G3, illustrated in FIG. 2A. The drug response curves for G4, G5, and G6 need not be considered here because the pathway originating at P1 does not affect these genes.

The transformation of the pathway response curves of FIG. 2B into the drug response curves of FIG. 2A generally can have both a vertical and a horizontal component. No vertical transformation of these response curves is expected in this example. The amplitudes of both sets of response curves will be the same, since they both vary over the same range, from 0, in a resting state without perturbation or drug exposure, to saturation, in a state where both drug and the perturbation have maximally affected pathway 101. However, horizontal transformation is likely to be necessary. Because there is no reason for the values defining the perturbation control, such as the exposure value of a viral transfection vector expressing P1, or controllable promoter of P1 expression, or another drug of specific known action on P1, to be the same as the values defining exposure to drug D under study, the drug and pathway response curves must be horizontally transformed in order to ascertain any possible match. Since the curves for G1, G2, and G3 in FIG. 2B have the same general shape as the corresponding curves in FIG. 2A, such a horizontally transformation is likely to be possible in this case.

Finding a horizontal transformation, according to this invention, proceeds by parameterization of a class of possible transformations. Then, optimum values of the parameters are sought that will make the pathway response explain the drug response as closely as possible. A preferable and simple class of transformations are linear scaling from values of the perturbation control parameter to values of the drug exposure, which are simply parameterized by the degree of stretch or shrinkage. Optimum values of the linear stretch can then be found by standard means, such as by minimization of an objective measure of the difference of the pathway and drug response curves.

Figure 2C:
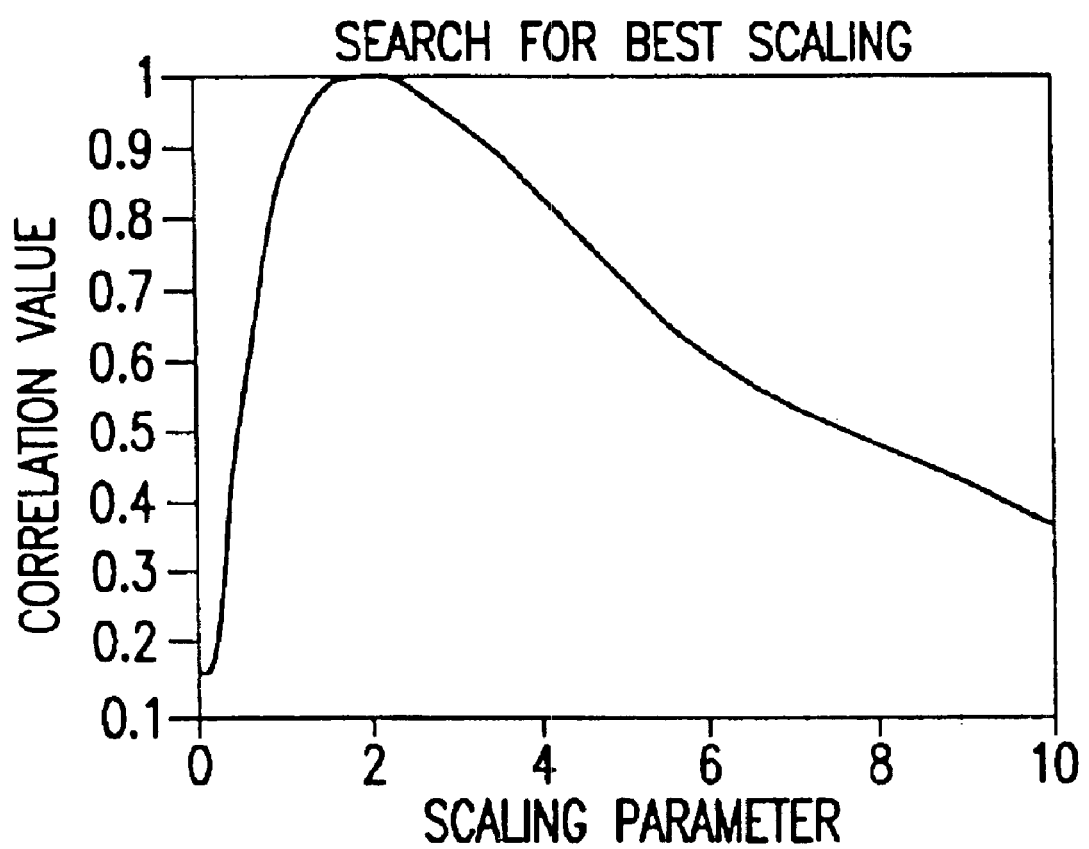
FIG. 2C illustrates an exemplary correlation between response illustrated in FIGS. 2A-B.

FIG. 2C sets forth an exemplary illustration of finding an optimum linear scaling parameter. The vertical axis of the graph of this figure indexes the average correlation value computed between the pathway response curves G1, G2, and G3 of FIG. 2B and the drug response curves G1, G2, and G3, respectively, of FIG. 2A. It is well known in the art that, when two curves are identical, they will have a perfect correlation of 1.0. The horizontal axis indexes possible linear scaling parameters from 0 to 10. In this example, a perfect correlation value of 1.0 occurs at a scaling parameter of 2. The pathway response curves of FIG. 2B can be transformed with a linear scaling of 2 to fully match the drug response curves of FIG. 2A. Therefore, it can be concluded that the pathway originating at P1 is one of the pathways of action of drug D.

In order to determine whether the entire action of drug D can be explained by the pathways originating at P1 and P2, according to this invention the sum (the pathways are disjoint) of the both pathway responses (the response of the pathway originating at P2 is not illustrated) can be transformed into the response curves of all six genes to drug D.

5.3 Analytic Embodiments

The analytic embodiments of the methods of this invention include, first, embodiments for representing drug response as a combination of pathway responses, and second, embodiments for assessing the statistical significance and verifying the results of the representation found.

Figure 5:
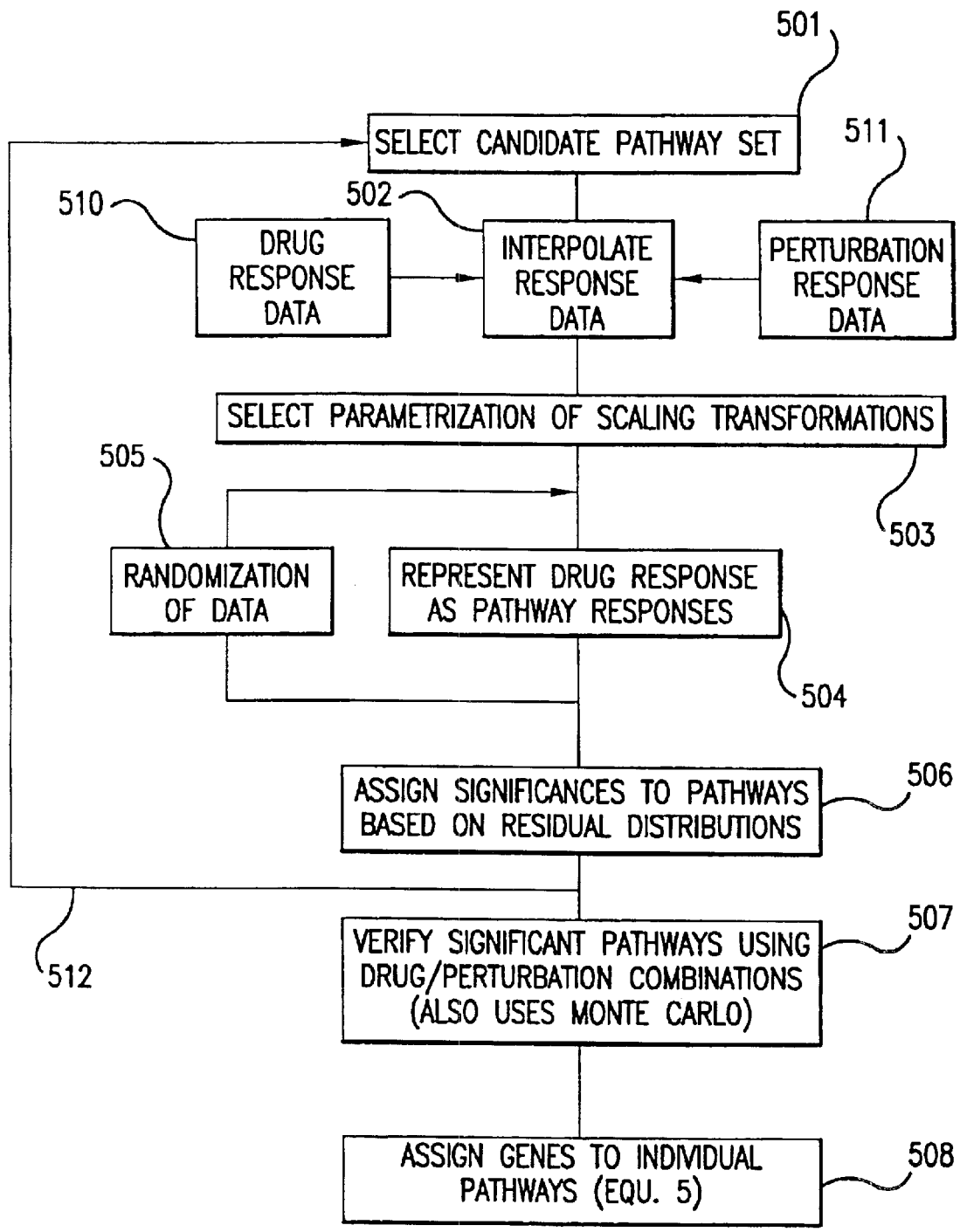
FIG. 5 illustrates a flow chart of an embodiment of the methods of the invention.

FIG. 5 sets out a flow chart for a preferred embodiment of the methods of this invention. This embodiment determines a representative drug response data 510 for a particular drug in terms of pathway response data 511 for one or more pathways along with significance assessment and verification of the representation determined.

In other embodiments of this invention, certain steps illustrated in FIG. 5 may be omitted or performed in orders other than as illustrated. For example, in certain embodiments candidate pathway selection, step 501, and scaling parameterization selection, step 502, can be performed once for the analysis of the response data from several, preferably related, drugs and need not be performed for each drug analysis separately. Also, in particular embodiments, pathway significance assignment and verification may not be performed, and accordingly, one or more of steps 505 and 506, step 507, or step 508 may be omitted.

5.3.1 Drug Response Representation

The representation of drug response data in terms of pathway response data preferably begins at step 501 with the selection of one or more candidate biological pathways with which to represent drug response data for a drug of interest. As discussed, the pathways preferably employed are those that originate at one or more cellular constituents, more referably at constituents that are proteins likely to be argets of the drug of interest. Most preferably, the candidate pathways originate at single cellular constituents that are likely to be targets of the drug of interest.

Where candidate drug targets are not known, single pathways can be chosen from among available pathways, perhaps stored in a compendium of pathways, and tested for significance in representing the drug response data according to the following steps illustrated in FIG. 5. Those pathways individually found to have significance in representing drug response data can then be employed combined, and the steps of FIG. 5 performed in order to determine the best pathway combination for representing drug action. A compendium of pathways is preferably substantially complete in the biological system used for the assay (in that it includes substantially all biological pathways in that system), or at least includes substantially all pathways likely to be involved in drug action.

Pathway response data are measured in step 511 for the pathways selected in step 501. In many cases, for example, where a pathway has been defined by measurement, response data will already have been measured for perturbations to the selected pathways. In other cases, this response data must be measured prior to the succeeding steps of this invention. As described above, response data for a pathway includes measurements of relative changes in relevant characteristics of the cellular constituents present in the pathway for a plurality of control levels of a perturbation to the pathway. For example, where the pathway is defined by gene expression levels originating at a protein constituent, the activity of the originating protein can be perturbed in a graded manner and the resulting ratios (or logarithms of these ratios) of native to perturbed gene expression levels are measured. The perturbation control levels are preferably chosen so that five or more, or more preferably ten or more, perturbation control levels are present in the region where the characteristics of the cellular constituents rapidly change from native levels to saturation levels.

In the following, the variable "p" refers generally to perturbation control levels, and the variable "R" refers generally to the pathway response data. In detail, the l'th perturbation control level in the i'th biological pathway is referred to as "$p_{i,l}$". The pathway response for the k'th cellular constituent in the i'th pathway is $R_{i,k}$. Therefore, $R_{i,k}(P_{i,l})$ is the response of the k'th cellular constituent in the i'th pathway at the l'th level of the perturbation control parameter.

Similarly, drug response data are obtained in step 510, and must be measured if not already available. As described above, these data are obtained by measuring changes in characteristics of cellular constituents at a plurality of levels of drug exposure (also called herein "levels of drug titration"). As with pathway response data, the drug exposure levels (or "drug titrations") are preferably chosen so that five or more, or more preferably ten or more, exposure values are present in the region where the characteristics of the cellular constituents rapidly change from native levels to saturation exposure levels, In the following, the variable "t" is used to refer generally to drug exposure (or "titration") levels, and the variable "D" refers generally to the drug response data. In detail, the l'th measured drug exposure level is referred to as "$t_l$". The drug response for the k'th cellular constituent is $D_k$. Therefore, $D_k(t_l)$ is the drug response of the k'th cellular constituent at the l'th level of drug exposure.

In the subsequent steps of these methods, in particular in step 504, values of the drug response data and the pathway response data may be needed at values of the drug exposure or perturbation control parameter which may not have been measured. This result follows from the fact that the measured drug exposure levels and pathway perturbation control parameters are not necessarily related. That is, for a particular l, the variables $t_l$ and $p_{i,l}$, for the various pathways, i, have no a priori relationship. Accordingly, it is necessary in step 502 to provide for interpolating of the various response data to obtain needed values. This interpolation method is preferably accomplished either by spline fitting or by model-fitting. The selection of an interpolation method and any necessary parameters are accomplished in step 502.

In spline fitting, the drug and pathway response data are interpolated by summing products of an appropriate spline interpolation function, S, multiplied by the measured data values, as illustrated by the following equations.

$$R_{i,k}(u) = \sum_l S(u - p_{i,l}) R_{i,k}(p_{i,l}) \qquad (1)$$

$$D_k(u) = \sum_l S(u - t_l) D_k(t_l)$$

The variable "u" refers to an arbitrary value of the drug exposure level or the perturbation control parameter at which the drug response data and the pathway response data, respectively, are to be evaluated. In general, S may be any smooth (at least piece-wise continuous) function of limited support having a width characteristic of the structure expected in the response functions. An exemplary width can be chosen to be the distance over which the response function being interpolated rises from 10% to 90% of its asymptotic value. Different S functions may be appropriate for the drug and the pathway response data, and even for the response data of different pathways. Exemplary S functions include linear and Gaussian interpolation.

In model fitting, the drug and pathway responses are interpolated by approximating each by a single parameterized function. An exemplary model-fitting function appropriate for approximating transcriptional state data is the Hill function, which has adjustable parameters a, $u_0$, and n.

$$H(u) = \frac{a(u/u_0)^n}{1 + (u/u_0)^n} \qquad (2)$$

The adjustable parameters are selected independently for each cellular constituent of the drug response and for each cellular constituent of the pathway response. Preferably, the adjustable parameters are selected so that for each cellular constituent of each pathway response the sum of the squares of the distances of $H(p_{i,l})$ from $R_{i,k}(p_{i,l})$ is minimized, and so that for each cellular constituent of the drug response the sum of the squares of the distances of $H(t_l)$ from $D_k(t_l)$ is minimized. This preferable parameter adjustment method is known in the art as a least squares fit of H( ) to $R_{i,k}$( ) or to $D_k$( ). Other possible model functions are based on polynomial fitting, for example by various known classes of polynomials.

Figure 4:
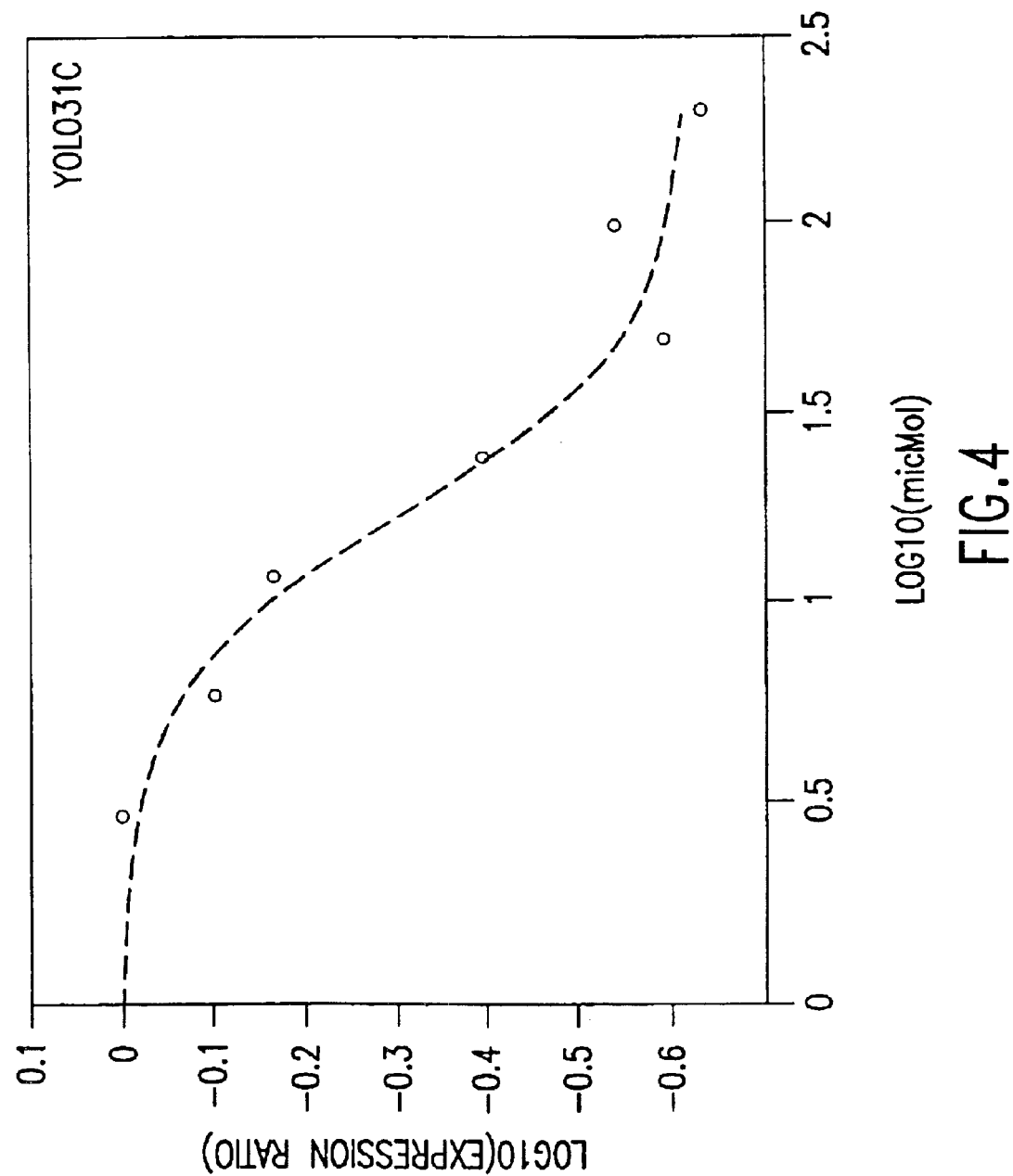
FIG. 4 illustrates the fit of a Hill function to the response of gene YOL031C illustrated in FIG. 3.

Model fitting with a Hill function is illustrated with respect to FIGS. 3 and 4. As discussed, FIG. 3 illustrates an example of a pathway perturbed by methotrexate and identified by measurement. This figure illustrates the mRNA expression levels of 30 genes of the yeast *S. cerevisiae* that, of the approximately 6000 genes in the genome of this yeast, had the largest expression changes in response to six different exposure levels of methotrexate. FIG. 4 illustrates a fit of the pathway response of one of these gene expression levels by a Hill function. In particular, the yeast gene YOL031C was fit by a Hill function with parameters n=2, a =−0.61, and $\log_{10}(u_0)$=1.26 selected by the previously described least squares method.

Since all of the 30 genes with largest responses behaved monotonically, i.e., none of the responses decreased significantly from its maximum amplitude (or increased significantly from its minimum amplitude) with increasing drug exposure, the Hill function is an appropriate model fitting function. For non-monotonic behavior it would not be.

After selection of a response data interpolation method, the last step prior to drug response data fitting, step 503, is the selection of a scaling transformation, along with any necessary parameters, which will relate the biological pathway responses to the drug responses. In general, a scaling transformation may need to scale vertically as well as horizontally. Vertical scalings may be necessary to relate the various measurements of the relevant characteristics of each cellular constituent made in acquiring the response data. For example, such measurements might be of abundances of mRNA species or activities of proteins. Where these measurements are made in commensurate units, vertical scalings are needed merely to relate the various units of measurement. Alternatively, where both drug and pathway measurements are made across a range of parameters from native levels to full saturation, as is preferable, these measurements can be scaled, for example, by the saturation values. Such scaling obviates the need for any vertical scaling. In this case, for example, where pathway responses are interpolated by fitting with a Hill function, the value of the parameter "a" for all response data will be substantially equal to 1. In the following, it is assumed that any necessary vertical scaling by saturation values has been done and that all pathway data vary between common native level and saturation values.

In general, horizontal scaling is expected to be necessary. As discussed above in Section 5.2, such scaling is necessary because values of the perturbation control parameters for the various candidate biological pathways are likely not to cause saturation responses at the same numerical perturbation control values nor at the same numerical value as the saturation response of the drug exposure. For example, the pathway perturbations may act according to such entirely different mechanisms as the titration of a viral transfection vector expressing a protein from which a pathway originates, or the control parameter of a controllable promoter controlling expression of an originating protein, or the exposure level of a drug of specific known action on an originating protein. The saturating control values of these mechanisms, and indeed their kinetic characteristics, are likely to be all unrelated. All of these mechanisms may be different from the action of the drug of interest. For example, where perturbation action on a cellular constituent from which a pathway originates can be modeled as a Hill function, there is no reason that the various "$u_0$" parameters will be the same.

The preferred horizontal scaling transformation is a linear transformation of the drug exposure level into corresponding perturbation control parameters. An exemplary expression of such a transformation follows.

$$p_{i,l} = \alpha_i t_l + \beta_i \quad (3)$$

Eqn. 3 provides the perturbation control value in the i'th pathway corresponding to the l'th drug exposure level. The linear scaling constants are $\alpha_i$ and $\beta_i$. Each pathway is characterized by one set of scaling parameters. Generally, $\beta_i$ will be 0 since both drug exposure and perturbation control values begin with zero. In essence, $\alpha_i$, represents a ratio of the strengths of the particular pathway perturbation to the drug of interest. For example, where the response data can be modeled as Hill functions, $\alpha_i$ is the ratio of the $u_0$ parameters of the drug of interest to that of the particular pathway.

More general horizontal scaling transformations are possible characterized by additional parameters. Flexible scaling transformations are possible with a number of parameters small enough, even though nonlinear, to be usefully employed in the minimization procedure of step 504. Multiple scaling parameters for the i'th pathway are represented herein by "$\alpha_i$". Another example of a scaling transformation is a polynomial expansion generalizing the linear transformation of Eqn 3. A simple example of a more general scaling transformation is the previously described Hill function employed according to the following equation.

$$p_{i,l} = \frac{\alpha_i (t_l / \mu_i)^{n_i}}{1 + (t_l / \mu_i)^{n_i}} \quad (4)$$

Again, Eqn. 3 provides the perturbation control value in the i'th pathway corresponding to the l'th drug exposure level and is parameterized for each pathway by the three parameters $\alpha_i$, $\mu_i$, and $n_i$. The Hill function scaling is more general at least in that it reduces to a linear scaling when $n_i$ is 1 and $t_l$ is much less than $\mu_i$.

Step 504 is the central step of the methods of this invention in which the drug response is represented as a combination of appropriately scaled pathway responses. The preferred representation of the drug response is as a scaled linear combination of the pathway responses. Such a representation is particularly useful when the cellular constituents affected by one pathway are either unaffected by the other pathways, or have linearly additive effects if multiple pathways converge on the same cellular constituent, such as an mRNA or protein abundance. Since the convergence or overlap of pathways is most likely far downstream of the primary targets, where the influences have branched out to include many genes, the effects of multiple pathways are more likely to accidentally act as independent and additive effects. If the effects converged through a new cellular constituent in the two pathways, independence and additivity is less likely. In such cases, multiplicative cross-product terms could be included which would represent, inter alia, multiplicative responses of a cellular constituent resulting from convergence of multiple pathways at that cellular constituent. Even in the latter case and in other cases where linear additivity does not hold, errors introduced by the linear additivity can be corrected with the techniques of Section 5.3.1.

Therefore, preferably, the drug response data is represented in terms of the pathway response data according to the following equation.

$$D_k(t_l) \simeq \sum_i R_{i,k}(\alpha_i, t_l); \quad k = 1, K; \quad l = 1, L \quad (5)$$

Eqn. 5 represents the model drug response of the k'th cellular constituent at the l'th level of drug exposure in terms of the sum of pathway responses for the k'th cellular constituent scaled according to the selected transformation parameterized by the $\alpha_i$. It is understood that in general, here and subsequently, that the $R_{i,k}(\ )$ are interpolated according to the methods of step 502, since it is rarely the case that measurements will have been made at the perturbation control values given by the scaled drug exposure levels. In cases where multiplicative cross-product terms are included (for example, in the cases previously described) Eqn. 5 would also include terms such as $R_{i,k}(\alpha_i, t_l) R_{j,k}(\alpha_j, t_l)$.

Sufficiently accurate solutions of this latter equation can be obtained by numerical approximation methods known in the art. These solutions determine the best scaling transformation so that the model drug response matches the drug response as closely as possible. Preferred methods provide a numerical indication (herein referred to as a "residual") of the degree to which Eqn. 5 is not perfectly satisfied. According to a preferred method, pathway scaling parameters can be determined from the minimization of the related least squares approximation problem.

$$\min_{\{\alpha_i\}} \left\{ \sum_k \sum_l \left| D_k(t_l) - \sum_i R_{i,k}(\alpha_i; t_l) \right|^2 \right\} \quad (6)$$

In Eqn. 6, the inner sum of the $R_{i,k}$, is over all interpolated pathway responses scaled according to the parameters $\alpha_i$ to correspond to the drug exposure level $t_l$. The parameters $\alpha_i$ for each biological pathway are generally a set of few parameters, such as from 1–5 parameters, defining the scaling transformation. The absolute square of the difference of this sum and the drug response at $t_l$ is in turn summed over all drug exposure levels, indexed by "l", and over all cellular constituents in the drug response or in the biological pathways, indexed by "k". The representation of the drug response in terms of the biological pathways is determined from the minimization of this latter sum with respect to the scaling transformation parameters for each pathway, the $\{\alpha_i\}$. The minimum value of this sum provides a numerical indication of the degree to which Eqn. 5 is satisfied, that is, the residual.

For linear scale transformations, Eqn. 6 has the following simpler form.

$$\min_{\{\alpha_i\}} \left\{ \sum_k \sum_l \left| D_k(t_l) - \sum_i R_{i,k}(\alpha_i t_l) \right|^2 \right\} \quad (7)$$

In Eqn. 7, each $\alpha_l$ is a single scaling constant for each biological pathway. Naturally, each $\alpha_l$ depends on the units chosen for the drug exposure and those chosen for the perturbation control value as well as on the actual physical relation between the potency of the drug and the potency of the perturbation method.

Minimization of least squares Eqns. 6 or 7 is performed using any of the many available numerical methods. See, e.g., Press et al., 1996, *Numerical Recipes in C*, 2nd Ed. Cambridge Univ. Press, Chs. 10, 14.; Branch et al., 1996, *Matlab Optimization Toolbox User's Guide*, Mathworks (Natick, Mass.). A preferred method is the Levenberg-Marquandt method (described in Press at al., Section 14.4). Since there are K genes, and L level of drug exposure, Eqns. 6 or 7 represent KL individual equations. The number of unknowns is equal to the number of hypothesized pathways times the number of scaling parameters per pathway. In the case of linear scaling, the number of scaling parameters equals the number of pathways. Typically, the number KL is much larger than the number of scaling parameters so that the least squares problem is considerably over-determined. Over-determination is advantageous in that it makes the solution robust, i.e., insensitive to measurement errors in individual cellular constituent responses.

An alternative to the least-squares procedure outlined in Eqns. 6 and 7 for solving Eqn. 5 is to maximize the normalized correlation between the model drug response and the measured drug response. This procedure is closely related mathematically to the least squares procedure. According to this procedure the $\alpha_i$ are determined from the solution to Eqn. 8.

$$\max_{\{\alpha_i\}} \left\{ \frac{\sum_k p_k(\alpha_i) A_{Dk} A_{Rk}}{\left( \sum_k (A_{Dk})^2 \sum_{k'} (A_{Rk'})^2 \right)^{1/2}} \right\} \quad (8)$$

In this equation, $p_k(\alpha_i)$ is the correlation coefficient between the drug response data for the k'th cellular constituent and the model pathway response for the k'th cellular constituent. In detail, this correlation coefficient is given by Eqn. 9.

$$p_k(\alpha_j) = \frac{\sum_l D_k(t_l) \left( \sum_i R_{i,k}(\alpha_i t_l) \right)}{\left( \sum_m (D_k(t_m))^2 \sum_n \sum_i (R_{ik}(\alpha_i t_n))^2 \right)^{1/2}} \quad (9)$$

In Eqn. 9, the inner sum (over i) represents the model drug response for the k'th cellular constituent. The product of the model and measured drug responses are summed over all levels of drug exposure, and the sum is normalized by the root-mean-square (also called herein "RMS") values of the these responses to give the correlation coefficients. Returning to Eqn. 8, the values of the correlation coefficient are preferably normalized by the amplitudes $A_{Dk}$ and $A_{Rk}$, which are the response amplitudes for the measured and model drug responses for the k'th cellular constituents. These amplitudes are chosen to be RMS values of the measured and model drug responses over all levels of drug exposure. This normalization gives greater weight to cellular constituents with larger amplitude responses, while ensuring that perfect correlation gives a value of unity.

Alternatively and less preferably, the correlation coefficients can be unnormalized, in which case the amplitudes in Eqn. 8 are taken to be unity. Also, instead of the correlation coefficients, the negative of the correlation coefficients can be used, in which case the expression of Eqn. 8 is minimized (instead of maximized) to find the best scaling parameters.

Eqns. 8 and 9 can be solved by the methods described in the case of the least squares methods. It will be clear to those skilled in the art that the above fitting approach is equivalent to minimizing the negative value of Eqn. 8.

In both the least squares and the correlation methods, the summation of the pathway responses over the transformed drug exposure levels may lead to values outside of the measured interval of perturbation control parameters. This is because the scaling parameters, $\alpha_i$, can be substantially greater or less than unity. In order to avoid extrapolation of measured values, the sums in both cases (in Eqns. 6 and 8) are extended only over the interval in which there is measured data.

When drug responses from two different drugs are being compared, the steps outlined above in this section can be performed to generate a correlation coefficient, or, alternatively, a least squares residual, which is a measure of similarity of the effects of the two drugs. In such an embodiment, only one response pathway is scaled to fit the drug response data. Thus, in this particular embodiment the response R of the second "perturbation" drug is compared to the response data of the first drug D according to Eqn. 5, above, where K=1.

5.3.2 Pathway Verification

Following determination of a representation of the drug response as a combination of pathway responses, it is preferable, although optional, to assign a statistical significance to the pathway combination determined in step 506 and to verify the pathways determined to be significant in step 507.

Assessing Statistical Significance

Concerning step 506, the statistical significance of a pathway combination is determined by comparing the value of the minimum residual determined from the solution of Eqn. 5 to an expected probability distribution of residuals. The less likely the minimum residual is in terms of such a distribution, the more significant is the determined pathway combination. In the case of the correlation maximization method, the same methods can be applied to the maximum found in Eqn. 8. In particular, an expected distribution of this maximums can be found (as described below), and the significance of the actually obtained maximum determined from this distribution.

An expected probability distribution of residuals can be estimated by any method known in the art. Typically, this distribution is estimated analytically based on certain a priori assumptions concerning input probability distributions. Since such analytic estimation is difficult in this case, it is preferable to estimate the residual distribution by modeling based on a method described by Fisher. See, e.g., Conover, 2nd ed. 1980, *Practical Nonparametric Statistics*, John Wiley. This method provides an empirical residual distribution by taking permutations or random subsets of the input data. In detail, here the input can be permuted with respect to the levels of drug exposure.

According to the preferred method, a residual distribution is constructed by repetitively solving Eqn. 5 with randomized input data and accumulating the residuals to form the empirical residual distribution. Thereby, the constructed empirical residual distribution arises from random data that has the same population statistics as the actual data. In detail, first, either the drug response data or the pathway response data (but not both) are randomized in step 505 with respect to the drug exposure levels or the perturbation control parameters, respectively. This randomization transformation is represented by the following transformation.

$$D_k(t_l) \leftarrow D_k(t_{\pi(l)})$$
$$R_{i,k}(p_{i,l}) \leftarrow R_{i,k}(p_{i,\pi(l)}) \qquad (10)$$

In Eqn. 10, $\pi$ represents a perturbation independently chosen for each cellular constituent. Either the drug response or the each pathway response (but not both) is randomized according to Eqn. 10. Accordingly, the randomized drug or pathway response data are derived from the measured data by independent perturbations of the measurement points. Second, Eqn. 5 is then solved by the chosen numerical approximation technique in step 504 and the value of the resulting residual saved. These steps are repeated for enough randomizations to construct a sufficiently significant expected probability distribution of residuals. In order to obtain confidence levels of 99% or better (i.e., a P-value less than 0.01), then more than 100 randomizations are needed.

Having constructed the empirical residual distribution, in step 506, the actually determined residual is compared to the constructed distribution and its probability determined in view of that distribution. This probability is the significance assigned to the pathway. In other words, the statistical significance of any fit of a combination of pathways to the drug response is given in the preferred embodiment by the smallness of the probability value that randomized data are fit better by the assumed combination of pathways than the actual data.

In some cases, the pathway combination initially chosen in step 501 has adequate significance. For example, this is so if the pathway combination has at least the standard 95% probability threshold commonly used in medical sciences. If so, then this initial pathway combination can be verified in step 507 and cellular components assigned to individual biological pathways in step 508. In other cases, an acceptable significance threshold will not be met at first. If so, then, as indicated by arrow 512, it can be advantageous to return to step 501 and select a new set of candidate pathways in order to find a set meeting the chosen threshold standard of significance.

Accordingly, the assigned significance provides an objective method for assigning significance values and choosing between pathway combinations. This objective method of assigning significance allows meaningful identification of pathways from a large set of possible pathways likely to be involved in the action of a drug of interest, and provides an objective basis for halting the search for the additional pathways when the model drug response (possibly combining a plurality of pathways) attains sufficient objective significance.

In an alternative use of the significance as determined above, a single candidate pathway may be tested for significance according to two different approaches. In a first approach, the model drug response is taken to involve only that candidate pathway, and the pathway response data along that pathway are compared to the drug response data by correlation or least-squares residual (as described in Section 5.3.1). The significance of the fit, as determined by the randomization methods above, is compared to a threshold, such as the 95% threshold standard in the medical sciences, and the candidate pathway is taken to be a pathway of drug action if the significance is greater than that threshold.

In a second approach, the model drug response is assumed to involve multiple pathways, including the candidate pathway of interest. The pathway response data are then selectively randomized by randomizing only the pathway data for the candidate pathway according to Eqn. 10. The significance of the model drug response against this selectively randomized data is assessed by the previous methods. If this latter significance is significantly less than the former significance of the actual data, then the candidate pathway is taken to have significantly improved the model drug response. In that case, the pathway is likely to be a pathway of action of the drug of interest.

Verifying Pathway Combinations

Concerning next step 507, the representation of a drug response in terms of pathway responses can be independently verified by the preferred, but optional, steps described in this subsection. In the previous steps of this invention (steps 510 and 511), a biological system was perturbed either by drug exposure or by perturbations of selected pathways, but not by both drug exposure and pathway perturbations. In steps 504 and 506, the results of drug exposure were fit by a combination of the results of selected pathway perturbations, and then the statistical significance of this fit was estimated. Now in step 507, simultaneous drug exposure and perturbation of the significant pathways determined in step 504 are used to verify the that these pathways are indeed the actual pathways of drug action.

Figure 6:
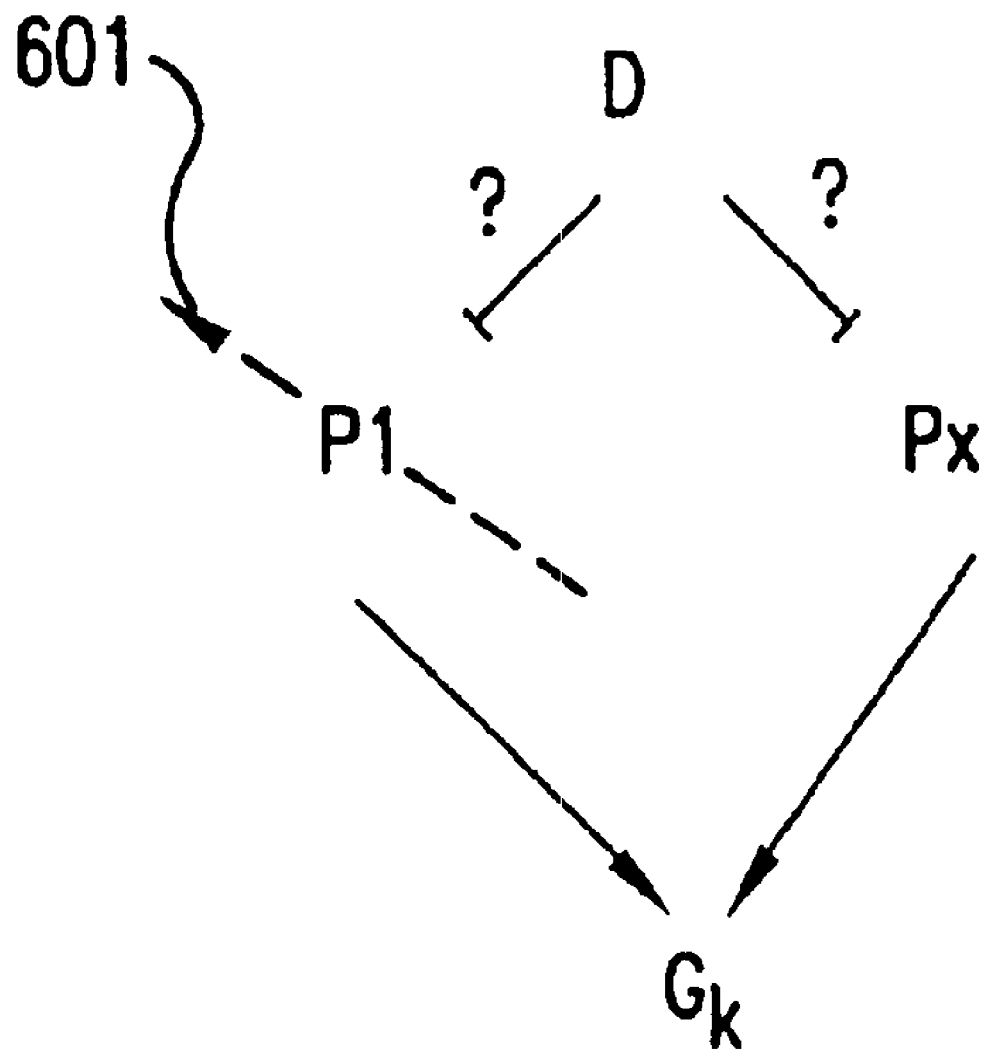
FIG. 6 illustrates possible alternative pathways for the action of drug D on Gene $G_k$.

Before describing the analytic details of pathway verification, the advantages of simultaneous drug exposure and pathway perturbation are exemplified with respect to the situation illustrated in FIG. 6. In FIG. 6., the expression of genes $G_k$ (for example, transcription state measurements of mRNA abundances) is affected by two pathways, one originating at protein P1 and the other at protein Px. Drug D is assumed to act on genes $G_k$ either by inhibiting P1 or by inhibiting Px. If the inhibitory perturbations to the two pathways produce similar responses in the genes Gk, then even if drug D acts only by inhibiting Px, its drug response will be well fit in step 504 by inhibitory perturbation 601 to the pathway originating at P1, and this pathway may be incorrectly identified as being the likely pathway of action of drug D. This error can be remedied by simultaneous exposure to drug D and inhibition of P1 or of Px. Exposure to drug D and inhibition of P1 will not result in a changed drug response, since the drug response is in fact mediated via Px. However, exposure to drug D and inhibition of Px will result in a changed drug response, since both the drug and the perturbation now act at Px. The different responses to simultaneous drug exposure and pathway perturbation in these two cases allow the correct pathway of action of drug D to be unambiguously identified.

The general description of verification step 507 begins, first, with consideration of the case where only one pathway is involved in representing the drug response, and follows with consideration of the general case of multiple pathways. In the following, as previously, $D_k(t_l)$ refers to the response of the k'th cellular constituent to the l'th level of drug exposure, and $R_{i,k}(p_{i,l})$ refers to the response of the k'th cellular constituent in the i'th pathway in response to the l'th level of the appropriate perturbation control parameter. Further, the variable DR refers to the results of the combined exposure of the biological system to both the drug and to a pathway perturbation. In detail, $D_{i,k}(p_{i,l}, t_m)$ refers to the response of the k'th cellular constituent in the i'th pathway in response to the l'th level of the appropriate perturbation control parameter and to the m'th level of drug exposure.

In the case of a single pathway of drug action, if the drug indeed acts on that pathway then the combined response, DR, is given by the following.

$$DR_{i,k}(p_{i,l}, t_m) = R_{i,k}(p_{i,l} + \alpha_i t_m) \quad (11)$$

where $\alpha_i$ is the best scaling parameter determined for this pathway. A linear scaling is assumed here; adaptation to more general scaling transformations is apparent from the preceding description. DR has the foregoing form because, in this case, both the drug and the perturbation act on the same constituents of the pathway, in particular on their originating constituents, and the response of the pathway is due to the summed effect.

Figure 7A:
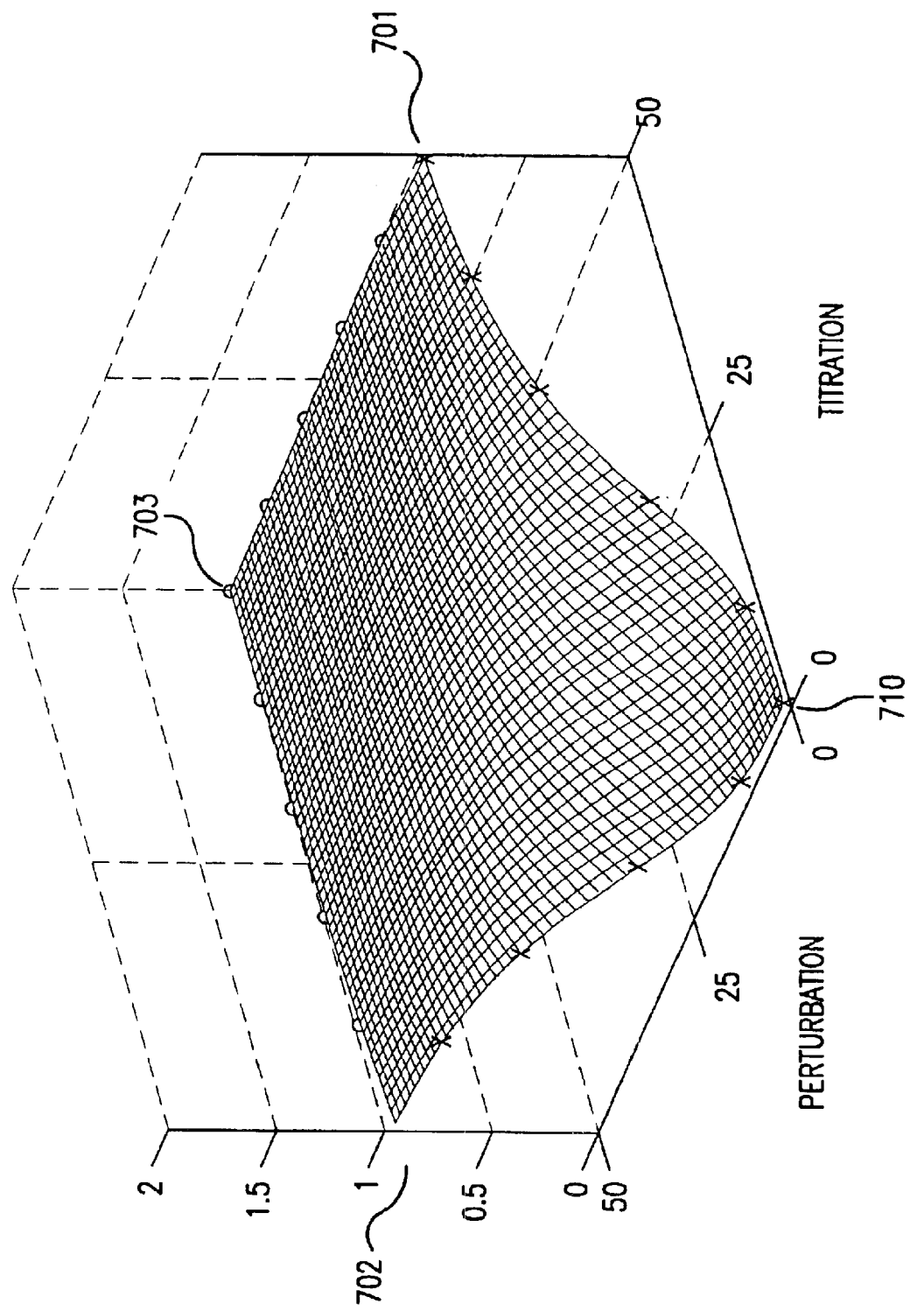
FIGS. 7A-B illustrate surface renderings of Eqns. 10 and 11.

The behavior of Eqn. 11 is illustrated in FIG. 7A, where, for purposes of example only, D and R have been modeled by the Hill function. Characteristically, the function DR in this case saturates at substantially the same values for large drug exposure (drug "titrations"), near asterisk 701, for large perturbation, near asterisk 702, and for the combination of large drug exposure and large perturbations, near open circle 703.

If, instead, the drug acts on a different pathway, not on the i'th pathway, then the combined response, DR, is given by the following.

$$DR_{i,k}(p_{i,l}, t_m) = R_{l,k}(p_{i,l}) + D_k(t_m) \quad (12)$$

The response has this form in this case because the drug acts only on cellular constituents outside of the i'th pathway. Since the pathway perturbation is limited to cellular constituents in the i'th pathway, it acts independently of the drug. Consequently, the action of the drug and the perturbation are independent and their effects are additive on cellular constituents. (The effects may be combined as needed according to the other combination functions discussed in Section 5.2)

Figure 7B:
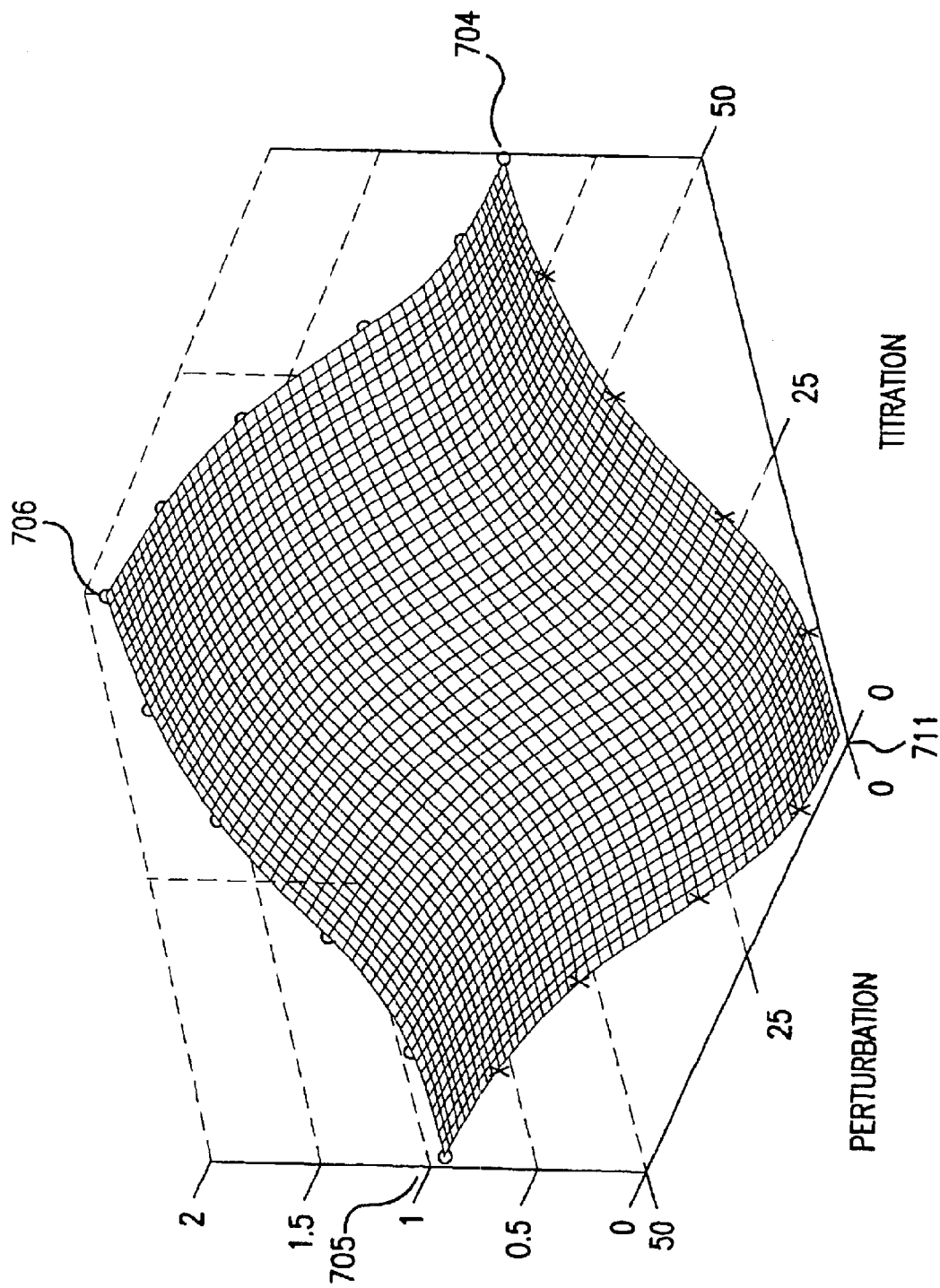

The behavior of Eqn. 12 (assuming $\alpha_i$, equals 1) is illustrated in FIG. 7B, where, for purposes of example only, D and R have again been modeled by the Hill function. In this case, the function DR saturates at substantially the same values for large drug exposure (drug "titrations"), near asterisk 704, and for large perturbation, near asterisk 705. But for the combination of large drug exposure and large perturbations, this function reaches substantially higher values near open circle 706 than at either asterisks 704 or 705, where only the drug exposure or the perturbation alone is saturating.

Clearly, it is possible to distinguish the cases represented by FIGS. 7A and 7B by performing experiments for verification conditions where both the drug exposure and the pathway perturbation are simultaneously present. Such experiments are preferably at drug exposure and perturbation values represented by the open circles in FIGS. 7A and 7B, and most preferably at open circles 703 and 706. Less preferably, these experiments are performed at values in the interior of the surfaces illustrated in these figures, especially in the region bounded by lines between asterisks 701 and 702 and open circle 703 in FIG. 7A, and in the region bounded by lines between asterisks 703 and 704 and open circle 705 in FIG. 7B. It is also clear that it would not be possible to distinguish these cases solely by performing experiments in which only one of the drug exposure or perturbation control values are non-zero. The curves in FIG. 7A between asterisk 710 and either asterisk 701 or asterisk 702 are substantially the same as the curves in FIG. 7B between asterisk 711 and either asterisk 704 or asterisk 705.

In summary, the identification of the i'th pathway as the pathway of drug action is verified if experimental results more closely resemble FIG. 7A than FIG. 7B.

Considering the case of multiple pathway in general, $TR_k(p_{i,l}, t_m)$ refers to the total response of the k'th cellular constituent in response to the l'th level of the appropriate perturbation control parameter in the i'th pathway and to the m'th level of drug exposure. TR is given by the following equation if the drug acts through the indicated pathways.

$$TR_k(p_{i,l}, t_m) = \sum_i DR_{i,k}(p_{i,l}, t_m) = \sum_i R_{i,k}(p_{i,l} + \alpha_i t_m) \quad (13)$$

TR is given by the following equation if the drug does not act through the indicated pathways.

$$TR(p_{i,l}, t_m) = \sum_i DR_{i,k}(p_{i,l}, t_m) = \sum_i (R_{i,k}(p_{i,l}) + D_k(t_m)) \quad (14)$$

An objective choice between these two possibilities can be made in a manner similar to the statistical confidence estimation method described in the previous subsection. Values for $TR_k(p_{i,l}, t_m)$, the left-hand side of Eqns. 13 and 14, are experimentally determined for various preferred verification conditions, and values for the right-hand side are computed from the measurements of the drug response and the pathway responses in steps 510 and 511 and from the determination of the optimum scaling parameters in step 504. The residuals for these equations, that is the sum of the squares of the differences of the left- and right-hand sides, are then computed. Without more, the alternative with the lesser residual is the objective choice.

The statistical significance of the residuals can be estimated by, first, estimating a probability distribution of residuals. The estimated residual probability distribution is determined by repeatedly randomizing the right hand sides of Eqns. 13 and 14 with respect to the perturbation control parameter index and the drug exposure index and then recomputing the residuals. The statistical significance of the actual residuals are then determined with respect to this model probability distribution.

Typically, only a small number of verification conditions are needed to confirm with significance the existence of a pathway which was determined to be significant in step 506.

In final optional step 508, after drug responses have been represented as a combination of pathway responses in step 504 and best-fit scaling parameters have been accordingly determined, each affected cellular constituent can be assigned to the pathway with which its drug response is most correlated. Optionally, the pathways have also been declared significant in step 506 based, for example, on a significance threshold, such as the standard 95% probability threshold often used in the medical sciences. For the k'th cellular constituent its drug response, $D_k(t_1)$, is correlated with the individual response of that constituent in the response data of each pathway.

$$\rho_{i,k} = \text{corr}(D_k(t_l) R_{i,k}(\alpha_i t_l)) \quad (15)$$

$$= \frac{\sum_l D_k(t_l) R_{i,k}(\alpha_i t_l)}{\left( \sum_m (D_k(t_m))^2 \sum_n (R_{Jk}(\alpha_J t_n))^2 \right)^{1/2}}$$

In Eqn. 15, $p_{i,k}$ is the correlation of the drug response of the k'th cellular constituent with its response in the i'th pathway. The k'th cellular constituent is assigned to the i'th pathway where $p_{i,k}$ is larger than $p_{i,k}$ for all 1 not equal to i. Similarly to the previous significance estimations, the statistical significance of this correlation can be determined by randomizing the drug response data in Eqn. 15.

5.3.3 Implementation Systems and Methods

Figure 9:
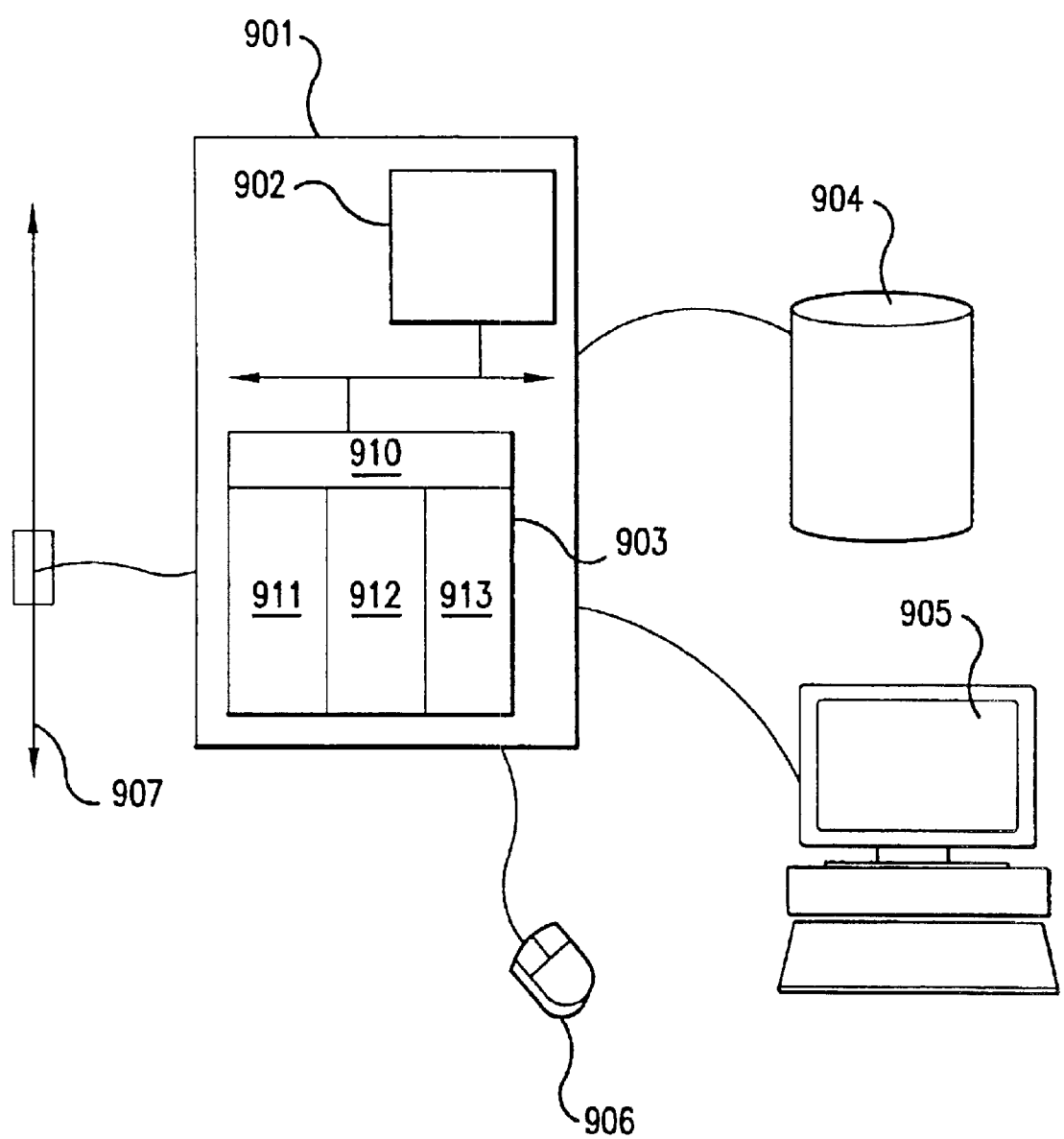
FIG. 9 illustrates an exemplary embodiment of a computer system of this invention.

The analytic methods described in the previous subsections can preferably be implemented by use of the following computer systems and according to the following programs and methods. FIG. 9 illustrates an exemplary computer system suitable for implementation of the analytic methods of this invention. Computer system 901 is illustrated as comprising internal components and being linked to external components. The internal components of this computer system include processor element 902 interconnected with main memory 903. For example, computer system 901 can be an Intel Pentium®-based processor of 200 Mhz or greater clock rate and with 32 MB or more of main memory.

The external components include mass storage 904. This mass storage can be one or more hard disks (which are typically packaged together with the processor and memory). Such hard disks are typically of 1 GB or greater storage capacity. Other external components include user interface device 905, which can be a monitor and keyboard, together with pointing device 906, which can be a "mouse", or other graphic input devices (not illustrated). Typically, computer system 901 is also linked to network link 907, which can be part of an Ethernet link to other local computer systems, remote computer systems, or wide area communication networks, such as the Internet. This network link allows computer system 901 to share data and processing tasks with other computer systems.

Loaded into memory during operation of this system are several software components, which are both standard in the art and special to the instant invention. These software components collectively cause the computer system to function according to the methods of this invention. These software components are typically stored on mass storage 904. Software component 910 represents the operating system, which is responsible for managing computer system 901 and its network interconnections. This operating system can be of the Microsoft Windows™ family, such as Windows 95, Windows 98, or Windows NT. Software component 911 represents common languages and functions conveniently present on this system to assist programs implementing the methods specific to this invention. Languages that can be used to program the analytic methods of this invention include C and C++, or, less preferably, JAVA®. Most preferably, the methods of this invention are programmed in mathematical software packages which allow symbolic entry of equations and high-level specification of processing, including algorithms to be used, thereby freeing a user of the need to procedurally program individual equations or algorithms. Such packages include Matlab from Mathworks (Natick, Mass.), Mathematica from Wolfram Research (Champaign, Ill.), or S-Plus from Math Soft (Seattle, Wash.).

Accordingly, software components 912 and 913 represent the analytic methods of this invention as programmed in a procedural language or symbolic package. Component 912 represents programs implementing the methods for drug response representation described in Section 5.3.1, and component 913 represents programs implementing the methods for assessing the significance of a drug response representation described in Section 5.3.2.

In an exemplary implementation, to practice the methods of this invention, a user first loads drug response data and pathway response data into computer system 901. These data can be directly entered by the user from monitor and keyboard 905, or from other computer systems linked by network connection 907, or on removable storage media (not illustrated). Next, the user causes execution of drug response representation software 912, after optionally supplying initial pathways of interest, followed by execution of significance assessment software 913. Thereby, the user obtains a model drug response and its statistical significance. Finally, as described in Section 5.3.2, the user can iteratively improve on a first model drug response according to several alternatives by causing repetitive and iterative execution of the drug response representation software and the statistical significance assessment software.

Alternative systems and methods for implementing the analytic methods of this invention will be apparent to one of skill in the art and are intended to be comprehended within the accompanying claims. In particular, the accompanying claims are intended to include the alternative program structures for implementing the methods of this invention that will be readily apparent to one of skill in the art.

5.4 Pathway Perturbation Methods

Methods for targeted perturbation of biological pathways at various levels of a cell are increasingly widely known and applied in the art. Any such methods that are capable of specifically targeting and controllably modifying (e.g., either by a graded increase or activation or by a graded decrease or inhibition) specific cellular constituents (e.g., gene expression, RNA concentrations, protein abundances, protein activities, or so forth) can be employed in performing pathway perturbations. Controllable modifications of cellular constituents consequentially controllably perturb pathways originating at the modified cellular constituents. Such pathways originating at specific cellular constituents are preferably employed to represent drug action in this invention. Preferable modification methods are capable of individually targeting each of a plurality of cellular constituents and most preferably a substantial fraction of such cellular constituents.

The following methods are exemplary of those that can be used to modify cellular constituents and thereby to produce pathway perturbations which generate the pathway responses used in the steps of the methods of this invention as previously described. This invention is adaptable to other methods for making controllable perturbations to pathways, and especially to cellular constituents from which pathways originate.

Pathway perturbations are preferably made in cells of cell types derived from any organism for which genomic or expressed sequence information is available and for which methods are available that permit controllably modification of the expression of specific genes. Genome sequencing is currently underway for several eukaryotic organisms, including humans, nematodes, *Arabidopsis*, and flies. In a preferred embodiment, the invention is carried out using a yeast, with *Saccharomyces cerevisiae* most preferred because the sequence of the entire genome of a *S. cerevisiae* strain has been determined. In addition, well-established methods are available for controllably modifying expression of year genes. A preferred strain of yeast is a *S. cerevisiae* strain for which yeast genomic sequence is known, such as strain S288C or substantially isogeneic derivatives of it (see, e.g., *Nature* 369, 371-8 (1994); *P.N.A.S.* 92:3809–13 (1995); *E.M.B.O. J.* 13:5795–5809 (1994), *Science* 265:2077–2082 (1994); *E.M.B.O. J.* 15:2031–49 (1996), all of which are incorporated herein. However, other strains may be used as well. Yeast strains are available from American Type Culture Collection, Rockville, Md. 20852. Standard techniques for manipulating yeast are described in C. Kaiser, S. Michaelis, & A. Mitchell, 1994, *Methods in Yeast Genetics: A Cold Spring Harbor Laboratory Course Manual*, Cold Spring Harbor Laboratory Press, New York; and Sherman et al., 1986, Methods in Yeast Genetics: A Laboratory Manual, Cold Spring Harbor Laboratory, Cold Spring Harbor. N.Y., both of which are incorporated by reference in their entirety and for all purposes.

The exemplary methods described in the following include use of titratable expression systems, use of transfection or viral transduction systems, direct modifications to RNA abundances or activities, direct modifications of protein abundances, and direct modification of protein activities including use of drugs (or chemical moieties in general) with specific known action.

Titratable Expression Systems

Any of the several known titratable, or equivalently controllable, expression systems available for use in the budding yeast *Saccharomyces cerevisiae* are adaptable to this invention (Mumberg et al., 1994, Regulatable promoter of *Saccharomyces cerevisiae*: comparison of transcriptional activity and their use for heterologous expression, Nucl. Acids Res. 22:5767-5768). Usually, gene expression is controlled by transcriptional controls, with the promoter of the gene to be controlled replaced on its chromosome by a controllable, exogenous promoter. The most commonly used controllable promoter in yeast is the GAL1 promoter (Johnston et al., 1984, Sequences that regulate the divergent GAL1–GAL10 promoter in *Saccharomyces cerevisiae*, Mol Cell. Biol. 8:1440-1448). The GAL1 promoter is strongly repressed by the presence of glucose in the growth medium, and is gradually switched on in a graded manner to high levels of expression by the decreasing abundance of glucose and the presence of galactose. The GAL1 promoter usually allows a 5–100 fold range of expression control on a gene of interest.

Other frequently used promoter systems include the MET25 promoter (Kerjan et al., 1986, Nucleotide sequence of the *Saccharomyces cerevisiae* MET25 gene, Nucl. Acids. Res. 14:7861–7871), which is induced by the absence of methionine in the growth medium, and the CUP1 promoter, which is induced by copper (Mascorro-Gallardo et al., 1996, Construction of a CUP1 promoter-based vector to modulate gene expression in *Saccharomyces cerevisiae*, Gene 172:169–170). All of these promoter systems are controllable in that gene expression can be incrementally controlled by incremental changes in the abundances of a controlling moiety in the growth medium.

One disadvantage of the above listed expression systems is that control of promoter activity (effected by, e.g., changes in carbon source, removal of certain amino acids), often causes other changes in cellular physiology which independently alter the expression levels of other genes. A recently developed system for yeast, the Tet system, alleviates this problem to a large extent (Gari et al., 1997, A set of vectors with a tetracycline-regulatable promoter system for modulated gene expression in *Saccharomyces cerevisiae*, Yeast 13:837–848). The Tet promoter, adopted from mammalian expression systems (Gossen et al., 1995, Transcriptional activation by tetracyclines in mammalian cells, Proc. Nat. Acad. Sci. USA 89:5547–5551) is modulated by the concentration of the antibiotic tetracycline or the structurally related compound doxycycline. Thus, in the absence of doxycycline, the promoter induces a high level of expression, and the addition of increasing levels of doxycycline causes increased repression of promoter activity. Intermediate levels gene expression can be achieved in the steady state by addition of intermediate levels of drug. Furthermore, levels of doxycycline that give maximal repression of promoter activity (10 micrograms/ml) have no significant effect on the growth rate on wild type yeast cells (Gari et al., 1997, A set of vectors with a tetracycline-regulatable promoter system for modulated gene expression in *Saccharomyces cerevisiae*, Yeast 13:837–848).

In mammalian cells, several means of titrating expression of genes are available (Spencer, 1996, Creating conditional mutations in mammals, Trends Genet. 12:181–187). As mentioned above, the Tet system is widely used, both in its original form, the "forward" system, in which addition of doxycycline represses transcription, and in the newer "reverse" system, in which doxycycline addition stimulates transcription (Gossen et al., 1995, Proc. Natl. Acad. Sci. USA 89:5547–5551; Hoffmann et al., 1997, Nucl. Acids. Res. 25:1078–1079; Hofmann et al., 1996, Proc. Natl. Acad. Sci. USA 83:5185–5190; Paulus et al., 1996, Journal of Virology 70:62–67). Another commonly used controllable promoter system in mammalian cells is the ecdysone-inducible system developed by Evans and colleagues (No et al., 1996, Ecdysone-inducible gene expression in mammalian cella and transgenic mice, Proc. Nat. Acad. Sci. USA 93:3346–3351), where expression is controlled by the level of muristerone added to the cultured cells. Finally, expression can be modulated using the "chemical-induced dimerization" (CID) system developed by Schreiber, Crabtree, and colleagues (Belshaw et al., 1996, Controlling protein association and subcellular localization with a synthetic ligand that induces heterodimerization of proteins, Proc. Nat. Acad. Sci. USA 93:4604–4607; Spencer, 1996, Creating conditional mutations in mammals, Trends Genet. 12:181–187) and similar systems in yeast. In this system, the gene of interest is put under the control of the CID-responsive promoter, and transfected into cells expressing two different hybrid proteins, one comprised of a DNA-binding domain fused to FKBP12, which binds FK506. The other hybrid protein contains a transcriptional activation domain also fused to FKBP12. The CID inducing molecule is FK1012, a homodimeric version of FK506 that is able to bind simultaneously both the DNA binding and transcriptional activating hybrid proteins. In the graded presence of FK1012, graded transcription of the controlled gene is activated.

For each of the mammalian expression systems described above, as is widely known to those of skill in the art, the gene of interest is put under the control of the controllable promoter, and a plasmid harboring this construct along with an antibiotic resistance gene is transfected into cultured mammalian cells. In general, the plasmid DNA integrates into the genome, and drug resistant colonies are selected and screened for appropriate expression of the regulated gene. Alternatively, the regulated gene can be inserted into an episomal plasmid such as pCEP4 (Invitrogen, Inc.), which contains components of the Epstein-Barr virus necessary for plasmid replication.

In a preferred embodiment, titratable expression systems, such as the ones described above, are introduced for use into cells or organisms lacking the corresponding endogenous gene and/or gene activity, e.g., organisms in which the endogenous gene has been disrupted or deleted. Methods for producing such "knock outs" are well known to those of skill in the art, see e.g., Pettitt et al., 1996, Development 122:4149–4157; Spradling et al., 1995, Proc. Natl. Acad. Sci. USA, 92:10824–10830; Ramirez-Solis et al., 1993, Methods Enzymol. 225:855–878; and Thomas et al., 1987, Cell 51:503–512.

Transfection Systems for Mammalian Cells

Transfection or viral transduction of target genes can introduce controllable perturbations in biological pathways in mammalian cells. Preferably, transfection or transduction of a target gene can be used with cells that do not naturally express the target gene of interest. Such non-expressing cells can be derived from a tissue not normally expressing the target gene or the target gene can be specifically mutated in the cell. The target gene of interest can be cloned into one of many mammalian expression plasmids, for example, the pcDNA3.1+/−system (Invitrogen, Inc.) or retroviral vectors, and introduced into the non-expressing host cells. Transfected or transduced cells expressing the target gene may be isolated by selection for a drug resistance marker encoded by the expression vector. The level of gene transcription is monotonically related to the transfection dosage. In this way, the effects of varying levels of the target gene may be investigated.

A particular example of the use of this method is the search for drugs that target the src-family protein tyrosine kinase, lck, a key component of the T cell receptor activation pathway (Anderson et al., 1994, Involvement of the protein tyrosine kinase p56 (lck) in T cell signaling and thymocyte development, Adv. Immunol. 56:171–178). Inhibitors of this enzyme are of interest as potential immunosuppressive drugs (Hanke JH, 1996, Discovery of a Novel, Potent, and src family-selective tyrosine kinase inhibitor, J. Biol Chem 271(2):695–701). A specific mutant of the Jurkat T cell line (JcaM1) is available that does not express lck kinase (Straus et al., 1992, Genetic evidence for the involvement of the lck tyrosine kinase in signal transduction through the T cell antigen receptor, Cell 70:585–593). Therefore, introduction of the lck gene into JCaM1 by transfection or transduction permits specific perturbation of pathways of T cell activation regulated by the lck kinase. The efficiency of transfection or transduction, and thus the level of perturbation, is dose related. The method is generally useful for providing perturbations of gene expression or protein abundances in cells not normally expressing the genes to be perturbed.

Methods of Modifying RNA Abundances or Activities

Methods of modifying RNA abundances and activities currently fall within three classes, ribozymes, antisense species, and RNA aptamers (Good et al., 1997, Gene Therapy 4: 45–54). Controllable application or exposure of a cell to these entities permits controllable perturbation of RNA abundances.

Ribozymes are RNAs which are capable of catalyzing RNA cleavage reactions. (Cech, 1987, Science 236:1532–1539; PCT International Publication WO 90/11364, published Oct. 4, 1990; Sarver et al., 1990, Science 247:1222–1225). "Hairpin" and "hammerhead" RNA ribozymes can be designed to specifically cleave a particular target mRNA. Rules have been established for the design of short RNA molecules with ribozyme activity, which are capable of cleaving other RNA molecules in a highly sequence specific way and can be targeted to virtually all kinds of RNA. (Haseloff et al., 1988, Nature 334:585–591; Koizumi et al., 1988, FEBS Lett., 228:228–230; Koizumi et al., 1988, FEBS Lett., 239:285–288). Ribozyme methods involve exposing a cell to, inducing expression in a cell, etc. of such small RNA ribozyme molecules. (Grassi and Marini, 1996, Annals of Medicine 28: 499–510; Gibson, 1996, Cancer and Metastasis Reviews 15:287–299).

Ribozymes can be routinely expressed in vivo in sufficient number to be catalytically effective in cleaving mRNA, and thereby modifying mRNA abundances in a cell. (Cotten et al., 1989, Ribozyme mediated destruction of RNA in vivo, The EMBO J. 8:3861–3866). In particular, a ribozyme coding DNA sequence, designed according to the previous rules and synthesized, for example, by standard phosphoramidite chemistry, can be ligated into a restriction enzyme site in the anticodon stem and loop of a gene encoding a tRNA, which can then be transformed into and expressed in a cell of interest by methods routine in the art. Preferably, an inducible promoter (e.g., a glucocorticoid or a tetracycline response element) is also introduced into this construct so that ribozyme expression can be selectively controlled. tDNA genes (i.e., genes encoding tRNAs) are useful in this application because of their small size, high rate of transcription, and ubiquitous expression in different kinds of tissues. Therefore, ribozymes can be routinely designed to cleave virtually any mRNA sequence, and a cell can be routinely transformed with DNA coding for such ribozyme sequences such that a controllable and catalytically effective amount of the ribozyme is expressed. Accordingly the abundance of virtually any RNA species in a cell can be perturbed.

In another embodiment, activity of a target RNA (preferable mRNA) species, specifically its rate of translation, can be controllably inhibited by the controllable application of antisense nucleic acids. An "antisense" nucleic acid as used herein refers to a nucleic acid capable of hybridizing to a sequence-specific (e.g., non-poly A) portion of the target RNA, for example its translation initiation region, by virtue of some sequence complementarity to a coding and/or non-coding region. The antisense nucleic acids of the invention can be oligonucleotides that are double-stranded or single-stranded, RNA or DNA or a modification or derivative thereof, which can be directly administered in a controllable manner to a cell or which can be produced intracellularly by transcription of exogenous, introduced sequences in controllable quantities sufficient to perturb translation of the target RNA.

Preferably, antisense nucleic acids are of at least six nucleotides and are preferably oligonucleotides (ranging from 6 to about 200 oligonucleotides). In specific aspects, the oligonucleotide is at least 10 nucleotides, at least 15 nucleotides, at least 100 nucleotides, or at least 200 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone. The oligonucleotide may include other appending groups such as peptides, or agents facilitating transport across the cell membrane (see, e.g., Letsinger et al., 1989, Proc. Natl. Acad. Sci. U.S.A. 86: 6553–6556; Lemaitre et al., 1987, Proc. Natl. Acad. Sci. 84: 648–652; PCT Publication No. WO 88/09810, published Dec. 15, 1988), hybridization-triggered cleavage agents (see, e.g., Krol et al., 1988, BioTechniques 6:958–976) or intercalating agents (see, e.g., Zon, 1988, Pharm. Res. 5: 539–549).

In a preferred aspect of the invention, an antisense oligonucleotide is provided, preferably as single-stranded DNA. The oligonucleotide may be modified at any position on its structure with constituents generally known in the art.

The antisense oligonucleotides may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

In another embodiment, the oligonucleotide comprises at least one modified sugar moiety selected from the group including, but not limited to, arabinose, 2-fluoroarabinose, xylulose, and hexose.

In yet another embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the oligonucleotide is a 2-α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641).

The oligonucleotide may be conjugated to another molecule, e.g., a peptide, hybridization triggered cross-linking agent, transport agent, hybridization-triggered cleavage agent, etc.

The antisense nucleic acids of the invention comprise a sequence complementary to at least a portion of a target RNA species. However, absolute complementarity, although preferred, is not required. A sequence "complementary to at least a portion of an RNA," as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a target RNA it may contain and still form a stable duplex (or triplex, as the case may be). One skilled in the art can ascertain a tolerable degree of mismatch by use of standard procedures to determine the melting point of the hybridized complex. The amount of antisense nucleic acid that will be effective in the inhibiting translation of the target RNA can be is determined by standard assay techniques.

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc. In another embodiment, the oligonucleotide is a 2'-O-methylribonucleotide (Inoue et al., 1987, Nucl. Acids Res. 15:6131–6148), or a chimeric RNA-DNA analog (Inoue et al., 1987, FEBS Lett. 215; 327–330).

The synthesized antisense oligonucleotides can then be administered to a cell in a controlled manner. For example, the antisense oligonucleotides can be placed in the growth environment of the cell at controlled levels where they may be taken up by the cell. The uptake of the antisense oligonucleotides can be assisted by use of methods well known in the art.

In an alternative embodiment, the antisense nucleic acids of the invention are controllably expressed -intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequences encoding the antisense RNAs can be by any promoter known in the art to act in a cell of interest. Such promoters can be inducible or constitutive. Most preferably, promoters are controllable or inducible by the administration of an exogenous moiety in order to achieve controlled expression of the antisense oligonucleotide. Such controllable promoters include the Tet promoter. Less preferably usable promoters for mammalian cells include, but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296: 39–42), etc.

Therefore, antisense nucleic acids can be routinely designed to target virtually any mRNA sequence, and a cell can be routinely transformed with or exposed to nucleic acids coding for such antisense sequences such that an effective and controllable amount of the antisense nucleic acid is expressed. Accordingly the translation of virtually any RNA species in a cell can be controllably perturbed.

Finally, in a further embodiment, RNA aptamers can be introduced into or expressed in a cell. RNA aptamers are specific RNA ligands for proteins, such as for Tat and Rev RNA (Good et al., 1997, Gene Therapy 4:45–54) that can specifically inhibit their translation.

Methods of Modifying Protein Abundances

Methods of modifying protein abundances include, inter alia, those altering protein degradation rates and those using antibodies (which bind to proteins affecting abundances of activities of native target protein species). Increasing (or decreasing) the degradation rates of a protein species decreases (or increases) the abundance of that species. Methods for controllably increasing the degradation rate of a target protein in response to elevated temperature and/or exposure to a particular drug, which are known in the art, can be employed in this invention. For example, one such method employs a heat-inducible or drug-inducible N-terminal degron, which is an N-terminal protein fragment that exposes a degradation signal promoting rapid protein degradation at a higher temperature (e.g., 37° C.) and which is hidden to prevent rapid degradation at a lower temperature (e.g., 23° C.) (Dohmen et. al, 1994, Science 263:1273–1276). Such an exemplary degron is Arg-DHFR$^{ts}$, a variant of murine dihydrofolate reductase in which the N-terminal Val is replaced by Arg and the Pro at position 66 is replaced with Leu. According to this method, for example, a gene for a target protein, P, is replaced by standard gene targeting methods known in the art (Lodish et al., 1995, *Molecular Biology of the Cell*, W. H. Freeman and Co., New York, especially chap 8) with a gene coding for the fusion protein Ub-Arg-DHFR$^{ts}$-P ("Ub" stands for ubiquitin). The N-terminal ubiquitin is rapidly cleaved after translation exposing the N-terminal degron. At lower temperatures, lysines internal to Arg-DHFR$^{ts}$ are not exposed, ubiquitination of the fusion protein does not occur, degradation is slow, and active target protein levels are high. At higher temperatures (in the absence of methotrexate), lysines internal to Arg-DHFR$^{ts}$ are exposed, ubiquitination of the fusion protein occurs, degradation is rapid, and active target protein levels are low. Heat activation of degradation is controllably blocked by exposure methotrexate. This method is adaptable to other N-terminal degrons which are responsive to other inducing factors, such as drugs and temperature changes.

Target protein abundances and also, directly or indirectly, their activities can also be decreased by (neutralizing) antibodies. By providing for controlled exposure to such antibodies, protein abundances/activities can be controllably modified. For example, antibodies to suitable epitopes on protein surfaces may decrease the abundance, and thereby indirectly decrease the activity, of the wild-type active form of a target protein by aggregating active forms into complexes with less or minimal activity as compared to the wild-type unaggregated wild-type form. Alternately, antibodies may directly decrease protein activity by, e.g., interacting directly with active sites or by blocking access of substrates to active sites. Conversely, in certain cases, (activating) antibodies may also interact with proteins and their active sites to increase resulting activity. In either case, antibodies (of the various types to be described) can be raised against specific protein species (by the methods to be described) and their effects screened. The effects of the antibodies can be assayed and suitable antibodies selected that raise or lower the target protein species concentration and/or activity. Such assays involve introducing antibodies into a cell (see below), and assaying the concentration of the wild-type amount or activities of the target protein by standard means (such as immunoassays) known in the art. The net activity of the wild-type form can be assayed by assay means appropriate to the known activity of the target protein.

Antibodies can be introduced into cells in numerous fashions, including, for example, microinjection of antibodies into a cell (Morgan et al., 1988, Immunology Today 9:84–86) or transforming hybridoma mRNA encoding a desired antibody into a cell (Burke et al., 1984, Cell 36:847–858). In a further technique, recombinant antibodies can be engineering and ectopically expressed in a wide variety of non-lymphoid cell types to bind to target proteins as well as to block target protein activities (Biocca et al, 1995, Trends in Cell Biology 5:248–252). Preferably, expression of the antibody is under control of a controllable promoter, such as the Tet promoter. A first step is the selection of a particular monoclonal antibody with appropriate specificity to the target protein (see below). Then sequences encoding the variable regions of the selected antibody can be cloned into various engineered antibody formats, including, for example, whole antibody, Fab fragments, Fv fragments, single chain Fv fragments ($V_H$ and $V_L$ regions united by a peptide linker) ("ScFv" fragments), diabodies (two associated ScFv fragments with different specificities), and so forth (Hayden et al., 1997, Current Opinion in Immunology 9:210–212). Intracellularly expressed antibodies of the various formats can be targeted into cellular compartments (e.g., the cytoplasm, the nucleus, the mitochondria, etc.) by expressing them as fusions with the various known intracellular leader sequences (Bradbury et al., 1995, *Antibody Engineering* (vol. 2) (Borrebaeck ed.), pp 295–361, IRL Press). In particular, the ScFv format appears to be particularly suitable for cytoplasmic targeting.

Antibody types include, but are not limited to, polyclonal, monoclonal, chimeric, single chain, Fab fragments, and an Fab expression library. Various procedures known in the art may be used for the production of polyclonal antibodies to a target protein. For production of the antibody, various host animals can be immunized by injection with the target protein, such host animals include, but are not limited to, rabbits, mice, rats, etc. Various adjuvants can be used to increase the immunological response, depending on the host species, and include, but are not limited to, Freund's (complete and incomplete), mineral gels such as aluminum hydroxide, surface active substances such as lysolecithin, pluronic polyols, polyanions, peptides, oil emulsions, dinitrophenol, and potentially useful human adjuvants such as *bacillus* Calmette-Guerin (BCG) and *corynebacterium parvum*.

For preparation of monoclonal antibodies directed towards a target protein, any technique that provides for the production of antibody molecules by continuous cell lines in culture may be used. Such techniques include, but are not restricted to, the hybridoma technique originally developed by Kohler and Milstein (1975, Nature 256:495–497), the trioma technique, the human B-cell hybridoma technique (Kozbor et al., 1983, Immunology Today 4:72), and the EBV hybridoma technique to produce human monoclonal antibodies (Cole et al., 1985, *in Monoclonal Antibodies and Cancer Therapy*, Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. USA 80: 2026–2030), or by transforming human B cells with EBV virus in vitro (Cole et al., 1985, *in Monoclonal Antibodies and Cancer Therapy*, Alan R. Liss, Inc., pp. 77–96). In fact, according to the invention, techniques developed for the production of "chimeric antibodies" (Morrison et al., 1984, Proc. Natl. Acad. Sci. USA 81:6851–6855; Neuberger et al., 1984, Nature 312:604–608; Takeda et al., 1985, Nature 314: 452–454) by splicing the genes from a mouse antibody molecule specific for the target protein together with genes from a human antibody molecule of appropriate biological activity can be used; such antibodies are within the scope of this invention.

Additionally, where monoclonal antibodies are advantageous, they can be alternatively selected from large antibody libraries using the techniques of phage display (Marks et al., 1992, J. Biol. Chem. 267:16007–16010). Using this technique, libraries of up to $10^{12}$ different antibodies have been expressed on the surface of fd filamentous phage, creating a "single pot" in vitro immune system of antibodies available for the selection of monoclonal antibodies (Griffiths et al., 1994, EMBO J. 13:3245–3260). Selection of antibodies from such libraries can be done by techniques known in the art, including contacting the phage to immobilized target protein, selecting and cloning phage bound to the target, and subcloning the sequences encoding the antibody variable regions into an appropriate vector expressing a desired antibody format.

According to the invention, techniques described for the production of single chain antibodies (U.S. Pat. No. 4,946, 778) can be adapted to produce single chain antibodies specific to the target protein. An additional embodiment of the invention utilizes the techniques described for the construction of Fab expression libraries (Huse et al., 1989, Science 246:1275–1281) to allow rapid and easy identification of monoclonal Fab fragments with the desired specificity for the target protein.

Antibody fragments that contain the idiotypes of the target protein can be generated by techniques known in the art. For example, such fragments include, but are not limited to: the $F(ab')_2$ fragment which can be produced by pepsin digestion of the antibody molecule; the Fab' fragments that can be generated by reducing the disulfide bridges of the $F(ab')_2$ fragment, the Fab fragments that can be generated by treating the antibody molecule with papain and a reducing agent, and Fv fragments.

In the production of antibodies, screening for the desired antibody can be accomplished by techniques known in the art, e.g., ELISA (enzyme-linked immunosorbent assay). To select antibodies specific to a target protein, one may assay generated hybridomas or a phage display antibody library for an antibody that binds to the target protein.

Methods of Modifying Protein Activities

Methods of directly modifying protein activities include, inter alia, dominant negative mutations, specific drugs (used in the sense of this application) or chemical moieties generally, and also the use of antibodies, as previously discussed.

Dominant negative mutations are mutations to endogenous genes or mutant exogenous genes that when expressed in a cell disrupt the activity of a targeted protein species. Depending on the structure and activity of the targeted protein, general rules exist that guide the selection of an appropriate strategy for constructing dominant negative mutations that disrupt activity of that target (Hershkowitz, 1987, Nature 329:219–222). In the case of active monomeric forms, over expression of an inactive form can cause competition for natural substrates or ligands sufficient to significantly reduce net activity of the target protein. Such over expression can be achieved by, for example, associating a promoter, preferably a controllable or inducible promoter, of increased activity with the mutant gene. Alternatively, changes to active site residues can be made so that a virtually irreversible association occurs with the target ligand. Such can be achieved with certain tyrosine kinases by careful replacement of active site serine residues (Perlmutter et al., 1996, Current Opinion in Immunology 8:285–290).

In the case of active multimeric forms, several strategies can guide selection of a dominant negative mutant. Multimeric activity can be controllably decreased by expression of genes coding exogenous protein fragments that bind to multimeric association domains and prevent multimer formation. Alternatively, controllable over expression of an inactive protein unit of a particular type can tie up wild-type active units in inactive multimers, and thereby decrease multimeric activity (Nocka et al., 1990, The EMBO J. 9:1805–1813). For example, in the case of dimeric DNA binding proteins, the DNA binding domain can be deleted from the DNA binding unit, or the activation domain deleted from the activation unit. Also, in this case, the DNA binding domain unit can be expressed without the domain causing association with the activation unit. Thereby, DNA binding sites are tied up without any possible activation of expression. In the case where a particular type of unit normally undergoes a conformational change during activity, expression of a rigid unit can inactivate resultant complexes. For a further example, proteins involved in cellular mechanisms, such as cellular motility, the mitotic process, cellular architecture, and so forth, are typically composed of associations of many subunits of a few types. These structures are often highly sensitive to disruption by inclusion of a few monomeric units with structural defects. Such mutant monomers disrupt the relevant protein activities and can be controllably expressed in a cell.

In addition to dominant negative mutations, mutant target proteins that are sensitive to temperature (or other exogenous factors) can be found by mutagenesis and screening procedures that are well-known in the art.

Also, one of skill in the art will appreciate that expression of antibodies binding and inhibiting a target protein can be employed as another dominant negative strategy.

Drugs of specific known action

Finally, activities of certain target proteins can be controllably altered by exposure to exogenous drugs or ligands. In a preferable case, a drug is known that interacts with only one target protein in the cell and alters the activity of only that one target protein. Graded exposure of a cell to varying amounts of that drug thereby causes graded perturbations of pathways originating at that protein. The alteration can be either a decrease or an increase of activity. Less preferably, a drug is known and used that alters the activity of only a few (e.g., 2–5) target proteins with separate, distinguishable, and non-overlapping effects. Graded exposure to such a drug causes graded perturbations to the several pathways originating at the target proteins.

5.5 Measurement Methods

Drug response and pathway responses are obtained for use in the instant invention by measuring the cellular constituents changed by drug exposure or by pathway perturbation. These cellular characteristics can be of any aspect of the biological state of a cell. They can be of the transcriptional state, in which RNA abundances are measured, the translation state, in which protein abundances are measured, the activity state, in which protein activities are measured. The cellular characteristics can also be of mixed aspects, for example, in which the activities of one or more proteins originating a particular biological pathway are measured along with the RNA abundances (gene expressions) of cellular constituents in the pathway downstream of the originating protein(s). This section describes exemplary methods for measuring the cellular constituents in drug or pathway responses. This invention is adaptable to other methods of such measurement.

Embodiments of this invention based on measuring the transcriptional state of drug and pathway responses are preferred. The transcriptional state can be measured by techniques of hybridization to arrays of nucleic acid or nucleic acid mimic probes, described in the next subsection, or by other gene expression technologies, described in the subsequent subsection. However measured, the result is response data including values representing RNA abundance ratios, which usually reflect DNA expression ratios (in the absence of differences in RNA degradation rates). Such measurement methods are described in Section 5.5.1.

In various alternative embodiments of the present invention, aspects of the biological state other than the transcriptional state, such as the translational state, the activity state, or mixed aspects can be measured. Details of these embodiments are described in this section. Such measurement methods are described in Section 5.5.2.

5.5.1 Transcriptional State Measurement

Preferably, measurement of the transcriptional state is made by hybridization to transcript arrays, which are described in this subsection. Certain other methods of transcriptional state measurement are described later in this subsection.

Transcript Arrays Generally

In a preferred embodiment the present invention makes use of "transcript arrays" (also called herein "microarrays"). Transcript arrays can be employed for analyzing the transcriptional state in a cell, and especially for measuring the transcriptional states of a cells exposed to graded levels of a drug of interest or to graded perturbations to a biological pathway of interest.

In one embodiment, transcript arrays are produced by hybridizing detectably labeled polynucleotides representing the mRNA transcripts present in a cell (e.g., fluorescently labeled cDNA synthesized from total cell mRNA) to a microarray. A microarray is a surface with an ordered array of binding (e.g., hybridization) sites for products of many of the genes in the genome of a cell or organism, preferably most or almost all of the genes. Microarrays can be made in a number of ways, of which several are described below. However produced, microarrays share certain characteristics: The arrays are reproducible, allowing multiple copies of a given array to be produced and easily compared with each other. Preferably the microarrays are small, usually smaller than 5 cm$^2$, and they are made from materials that are stable under binding (e.g. nucleic acid hybridization) conditions. A given binding site or unique set of binding sites in the microarray will specifically bind the product of a single gene in the cell. Although there may be more than one physical binding site (hereinafter "site") per specific mRNA, for the sake of clarity the discussion below will assume that there is a single site.

It will be appreciated that when cDNA complementary to the RNA of a cell is made and hybridized to a microarray under suitable hybridization conditions, the level of hybridization to the site in the array corresponding to any particular gene will reflect the prevalence in the cell of mRNA transcribed from that gene. For example, when detectably labeled (e.g., with a fluorophore) cDNA complementary to the total cellular mRNA is hybridized to a microarray, the site on the array corresponding to a gene (i.e., capable of specifically binding the product of the gene) that is not transcribed in the cell will have little or no signal (e.g., fluorescent signal), and a gene for which the encoded mRNA is prevalent will have a relatively strong signal.

In preferred embodiments, cDNAs from two different cells are hybridized to the binding sites of the microarray. In the case of drug responses one cell is exposed to a drug and another cell of the same type is not exposed to the drug. In the case of pathway responses one cell is exposed to a pathway perturbation and another cell of the same type is not exposed to the pathway perturbation. The cDNA derived from each of the two cell types are differently labeled so that they can be distinguished. In one embodiment, for example, cDNA from a cell treated with a drug (or exposed to a pathway perturbation) is synthesized using a fluorescein-labeled dNTP, and cDNA from a second cell, not drug-exposed, is synthesized using a rhodamine-labeled dNTP. When the two cDNAs are mixed and hybridized to the microarray, the relative intensity of signal from each cDNA set is determined for each site on the array, and any relative difference in abundance of a particular mRNA detected.

In the example described above, the cDNA from the drug-treated (or pathway perturbed) cell will fluoresce green when the fluorophore is stimulated and the cDNA from the untreated cell will fluoresce red. As a result, when the drug treatment has no effect, either directly or indirectly, on the relative abundance of a particular mRNA in a cell, the mRNA will be equally prevalent in both cells and, upon reverse transcription, red-labeled and green-labeled cDNA will be equally prevalent. When hybridized to the microarray, the binding site(s) for that species of RNA will emit wavelengths characteristic of both fluorophores (and appear brown in combination). In contrast, when the drug-exposed cell is treated with a drug that, directly or indirectly, increases the prevalence of the mRNA in the cell, the ratio of green to red fluorescence will increase. When the drug decreases the mRNA prevalence, the ratio will decrease.

The use of a two-color fluorescence labeling and detection scheme to define alterations in gene expression has been described, e.g., in Shena et al., 1995, Quantitative monitoring of gene expression patterns with a complementary DNA microarray, *Science* 270:467–470, which is incorporated by reference in its entirety for all purposes. An advantage of using cDNA labeled with two different fluorophores is that a direct and internally controlled comparison of the mRNA levels corresponding to each arrayed gene in two cell states can be made, and variations due to minor differences in experimental conditions (e.g., hybridization conditions) will not affect subsequent analyses. However, it will be recognized that it is also possible to use cDNA from a single cell, and compare, for example, the absolute amount of a particular mRNA in, e.g., a drug-treated or pathway-perturbed cell and an untreated cell.

Preparation of Microarrays

Microarrays are known in the art and consist of a surface to which probes that correspond in sequence to gene products (e.g., cDNAs, mRNAs, cRNAs, polypeptides, and fragments thereof), can be specifically hybridized or bound at a known position. In one embodiment, the microarray is an array (i.e., a matrix) in which each position represents a discrete binding site for a product encoded by a gene (e.g., a protein or RNA), and in which binding sites are present for products of most or almost all of the genes in the organism's genome. In a preferred embodiment, the "binding site" (hereinafter, "site") is a nucleic acid or nucleic acid analogue to which a particular cognate cDNA can specifically hybridize. The nucleic acid or analogue of the binding site can be, e.g., a synthetic oligomer, a full-length cDNA, a less-than full length cDNA, or a gene fragment.

Although in a preferred embodiment the microarray contains binding sites for products of all or almost all genes in the target organism's genome, such comprehensiveness is not necessarily required. Usually the microarray will have binding sites corresponding to at least about 50% of the genes in the genome, often at least about 75%, more often at least about 85%, even more often more than about 90%, and most often at least about 99%. Preferably, the microarray has binding sites for genes relevant to the action of a drug of interest or in a biological pathway of interest. A "gene" is identified as an open reading frame (ORF) of preferably at least 50, 75, or 99 amino acids from which a messenger RNA is transcribed in the organism (e.g., if a single cell) or in some cell in a multicellular organism. The number of genes in a genome can be estimated from the number of mRNAs expressed by the organism, or by extrapolation from a well-characterized portion of the genome. When the genome of the organism of interest has been sequenced, the number of ORFs can be determined and mRNA coding regions identified by analysis of the DNA sequence. For example, the *Saccharomyces cerevisiae* genome has been completely sequenced and is reported to have approximately 6275 open reading frames (ORFS) longer than 99 amino acids. Analysis of these ORFs indicates that there are 5885 ORFs that are likely to specify protein products (Goffeau et al., 1996, Life with 6000 genes, *Science* 274:546–567, which is incorporated by reference in its entirety for all purposes). In contrast, the human genome is estimated to contain approximately $10^5$ genes.

Preparing Nucleic Acids for Microarrays

As noted above, the "binding site" to which a particular cognate cDNA specifically hybridizes is usually a nucleic acid or nucleic acid analogue attached at that binding site. In one embodiment, the binding sites of the microarray are DNA polynucleotides corresponding to at least a portion of each gene in an organism's genome. These DNAs can be obtained by, e.g., polymerase chain reaction (PCR) amplification of gene segments from genomic DNA, cDNA (e.g., by RT-PCR), or cloned sequences. PCR primers are chosen, based on the known sequence of the genes or cDNA, that result in amplification of unique fragments (i.e. fragments that do not share more than 10 bases of contiguous identical sequence with any other fragment on the microarray). Computer programs are useful in the design of primers with the required specificity and optimal amplification properties. See, e.g., Oligo version 5.0 (National Biosciences). In the case of binding sites corresponding to very long genes, it will sometimes be desirable to amplify segments near the 3' end of the gene so that when oligo-dT primed cDNA probes are hybridized to the microarray, less-than-full length probes will bind efficiently. Typically each gene fragment on the microarray will be between about 50 bp and about 2000 bp, more typically between about 100 bp and about 1000 bp, and usually between about 300 bp and about 800 bp in length. PCR methods are well known and are described, for example, in Innis et al. eds., 1990, *PCP Potocols: A Guide to Methods and Applications*, Academic Press Inc. San Diego, Calif., which is incorporated by reference in its entirety for all purposes. It will be apparent that computer controlled robotic systems are useful for isolating and amplifying nucleic acids.

An alternative means for generating the nucleic acid for the microarray is by synthesis of synthetic polynucleotides or oligonucleotides, e.g., using N-phosphonate or phosphoramidite chemistries (Froehler et al., 1986, *Nucleic Acid Res* 14:5399–5407; McBride et al., 1983, *Tetrahedron Lett.* 24:245–248). Synthetic sequences are between about 15 and about 500 bases in length, more typically between about and about 50 bases. In some embodiments, synthetic nucleic acids include non-natural bases, e.g., inosine. As noted above, nucleic acid analogues may be used as binding sites for hybridization. An example of a suitable nucleic acid analogue is peptide nucleic acid (see, e.g., Egholm et al., 1993, PNA hybridizes to complementary oligonucleotides obeying the Watson-Crick hydrogen-bonding rules, *Nature* 365:566–568; see also U.S. Pat. No. 5,539,083).

In an alternative embodiment, the binding (hybridization) sites are made from plasmid or phage clones of genes, cDNAs (e.g., expressed sequence tags), or inserts therefrom (Nguyen et al., 1995, Differential gene expression in the murine thymus assayed by quantitative hybridization of arrayed cDNA clones, *Genomics* 29:207–209). In yet another embodiment, the polynucleotide of the binding sites is RNA.

Attaching Nucleic Acids to the Solid Surface

The nucleic acid or analogue are attached to a solid support, which may be made from glass, plastic (e.g., polypropylene, nylon), polyacrylamide, nitrocellulose, or other materials. A preferred method for attaching the nucleic acids to a surface is by printing on glass plates, as is described generally by Schena et al., 1995, Quantitative monitoring of gene expression patterns with a complementary DNA microarray, *Science* 270:467–470. This method is especially useful for preparing microarrays of cDNA. See also DeRisi et al., 1996, Use of a cDNA microarray to analyze gene expression patterns in human cancer, *Nature Genetics* 14:457–460; Shalon et al., 1996, A DNA microarray system for analyzing complex DNA samples using two-color fluorescent probe hybridization, *Genome Res.* 6:639–645; and Schena et al., 1995, Parallel human genome analysis; microarray-based expression of 1000 genes, *Proc. Natl. Acad. Sci. USA* 93:10539–11286. Each of the aforementioned articles is incorporated by reference in its entirety for all purposes.

A second preferred method for making microarrays is by making high-density oligonucleotide arrays. Techniques are known for producing arrays containing thousands of oligonucleotides complementary to defined sequences, at defined locations on a surface using photolithographic techniques for synthesis in situ (see, Fodor et al., 1991, Light-directed spatially addressable parallel chemical synthesis, *Science* 251:767–773; Pease et al., 1994, Light-directed oligonucleotide arrays for rapid DNA sequence analysis, *Proc. Natl. Acad. Sci. USA* 91:5022–5026; Lockhart et al., 1996, Expression monitoring by hybridization to high-density oligonucleotide arrays, *Nature Biotech* 14:1675; U.S. Pat. Nos. 5,578,832; 5,556,752; and 5,510,270, each of which is incorporated by reference in its entirety for all purposes) or other methods for rapid synthesis and deposition of defined oligonucleotides (Blanchard et al., 1996, High-Density oligonucleotide arrays, Biosensors & Bioelectronics 11:687–90). When these methods are used, oligonucleotides (e.g., 20-mers) of known sequence are synthesized directly on a surface such as a derivatized glass slide. Usually, the array produced is redundant, with several oligonucleotide molecules per RNA. Oligonucleotide probes can be chosen to detect alternatively spliced mRNAs. Another preferred method of making microarrays is by use of an inkjet printing process to synthesize oligonucleotides directly on a solid phase, as described, e.g., in copending U.S. patent application Ser. No. 09/008,120 filed on Jan. 16, 1998 by Blanchard entitled "Chemical Synthesis Using Solvent Microdroplets", which is incorporated by reference herein in its entirety.

Other methods for making microarrays, e.g., by masking (Maskos and Southern, 1992, Nuc. Acids Res. 20:1679–1684), may also be used. In principal, any type of array, for example, dot blots on a nylon hybridization membrane (see Sambrook et al., Molecular Cloning—A Laboratory Manual (2nd Ed.), Vol. 1–3, Cold Spring Harbor Laboratory, Cold Spring Harbor, N.Y., 1989, which is incorporated in its entirety for all purposes), could be used, although, as will be recognized by those of skill in the art, very small arrays will be preferred because hybridization volumes will be smaller.

Generating Labeled Probes

Methods for preparing total and poly(A)$^+$ RNA are well known and are described generally in Sambrook et al., supra. In one embodiment, RNA is extracted from cells of the various types of interest in this invention using guanidinium thiocyanate lysis followed by CsCl centrifugation (Chirgwin et al., 1979, Biochemistry 18:5294–5299). Poly(A)$^+$ RNA is selected by selection with oligo-dT cellulose (see Sambrook et al., supra). Cells of interest include wild-type cells, drug-exposed wild-type cells, modified cells, and drug-exposed modified cells.

Labeled cDNA is prepared from mRNA by oligo dT-primed or random-primed reverse transcription, both of which are well known in the art (see e.g., Klug and Berger, 1987, Methods Enzymol. 152:316–325). Reverse transcription may be carried out in the presence of a dNTP conjugated to a detectable label, most preferably a fluorescently labeled dNTP. Alternatively, isolated mRNA can be converted to labeled antisense RNA synthesized by in vitro transcription of double-stranded cDNA in the presence of labeled dNTPs (Lockhart et al., 1996, Expression monitoring by hybridization to high-density oligonucleotide arrays, Nature Biotech. 14:1675, which is incorporated by reference in its entirety for all purposes). In alternative embodiments, the cDNA or RNA probe can be synthesized in the absence of detectable label and may be labeled subsequently, e.g., by incorporating biotinylated dNTPs or rNTP, or some similar means (e.g., photo-cross-linking a psoralen derivative of biotin to RNAs), followed by addition of labeled streptavidin (e.g., phycoerythrin-conjugated streptavidin) or the equivalent.

When fluorescently-labeled probes are used, many suitable fluorophores are known, including fluorescein, lissamine, phycoerythrin, rhodamine (Perkin Elmer Cetus), Cy2, Cy3, Cy3.5, Cy5, Cy5.5, Cy7, Fluor X (Amersham) and others (see, e.g., Kricka, 1992, Nonisotopic DNA Probe Techniques, Academic Press San Diego, Calif.). It will be appreciated that pairs of fluorophores are chosen that have distinct emission spectra so that they can be easily distinguished.

In another embodiment, a label other than a fluorescent label is used. For example, a radioactive label, or a pair of radioactive labels with distinct emission spectra, can be used (see Zhao et al., 1995, High density cDNA filter analysis: a novel approach for large-scale, quantitative analysis of gene expression, Gene 156:207; Pietu et al., 1996, Novel gene transcripts preferentially expressed in human muscles revealed by quantitative hybridization of a high density cDNA array, Genome Res. 6:492). However, because of scattering of radioactive particles, and the consequent requirement for widely spaced binding sites, use of radioisotopes is a less-preferred embodiment.

In one embodiment, labeled cDNA is synthesized by incubating a mixture containing 0.5 mM dGTP, dATP and dCTP plus 0.1 mM dTTP plus fluorescent deoxyribonucleotides (e.g., 0.1 mM Rhodamine 110 UTP (Perken Elmer Cetus) or 0.1 mM Cy3 dUTP (Amersham)) with reverse transcriptase (e.g., Superscript™ II, LTI Inc.) at 42° C. for 60 min.

Hybridization to Microarrays

Nucleic acid hybridization and wash conditions are chosen so that the probe "specifically binds" or "specifically hybridizes" to a specific array site, i.e., the probe hybridizes, duplexes or binds to a sequence array site with a complementary nucleic acid sequence but does not hybridize to a site with a non-complementary nucleic acid sequence. As used herein, one polynucleotide sequence is considered complementary to another when, if the shorter of the polynucleotides is less than or equal to 25 bases, there are no mismatches using standard base-pairing rules or, if the shorter of the polynucleotides is longer than 25 bases, there is no more than a 5% mismatch. Preferably, the polynucleotides are perfectly complementary (no mismatches). It can easily be demonstrated that specific hybridization conditions result in specific hybridization by carrying out a hybridization assay including negative controls (see, e.g., Shalon et al., supra, and Chee et al., supra).

Optimal hybridization conditions will depend on the length (e.g., oligomer versus polynucleotide greater than 200 bases) and type (e.g., RNA, DNA, PNA) of labeled probe and immobilized polynucleotide or oligonucleotide. General parameters for specific (i.e., stringent) hybridization conditions for nucleic acids are described in Sambrook et al., supra, and in Ausubel et al., 1987, Current Protocols in Molecular Biology, Greene Publishing and Wiley-Interscience, New York, which is incorporated in its entirety for all purposes. When the cDNA microarrays of Schena et al. are used, typical hybridization conditions are hybridization in 5×SSC plus 0.2% SDS at 65° C. for 4 hours followed by washes at 25° C. in low stringency wash buffer (1×SSC plus 0.2% SDS) followed by 10 minutes at 25° C. in high stringency wash buffer (0.1×SSC plus 0.2% SDS) (Shena et al., 1996, Proc. Natl. Acad. Sci. USA, 93:10614). Useful hybridization conditions are also provided in, e.g., Tijessen, 1993, Hybridization With Nucleic Acid Probes, Elsevier Science Publishers B.V. and Kricka, 1992, Nonisotopic DNA Probe Techniques, Academic Press San Diego, Calif.

Signal Detection and Data Analysis

When fluorescently labeled probes are used, the fluorescence emissions at each site of a transcript array can be, preferably, detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al., 1996, A DNA microarray system for analyzing complex DNA samples using two-color fluorescent probe hybridization, Genome Research 6:639–645, which is incorporated by reference in its entirety for all purposes). In a preferred embodiment, the arrays are scanned with a laser fluorescent scanner with a computer controlled X-Y stage and a microscope objective. Sequential excitation of the two fluorophores is achieved with a multi-line, mixed gas laser and the emitted light is split by wavelength and detected with two photomultiplier tubes. Fluorescence laser scanning devices are described in Schena et al., 1996, *Genome Res.* 6:639–645 and in other references cited herein. Alternatively, the fiber-optic bundle described by Ferguson et al., 1996, *Nature Biotech.* 14:1681–1684, may be used to monitor mRNA abundance levels at a large number of sites simultaneously.

Signals are recorded and, in a preferred embodiment, analyzed by computer, e.g., using a 12 bit analog to digital board. In one embodiment the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors may be made. For any particular hybridization site on the transcript array, a ratio of the emission of the two fluorophores can be calculated. The ratio is independent of the absolute expression level of the cognate gene, but is useful for genes whose expression is significantly modulated by drug administration, gene deletion, or any other tested event.

According to the method of the invention, the relative abundance of an mRNA in two cells or cell lines is scored as a perturbation and its magnitude determined (i.e., the abundance is different in the two sources of mRNA tested), or as not perturbed (i.e., the relative abundance is the same). As used herein, a difference between the two sources of RNA of at least a factor of about 25% (RNA from one source is 25% more abundant in one source than the other source), more usually about 50%, even more often by a factor of about 2 (twice as abundant), 3 (three times as abundant) or 5 (five times as abundant) is scored as a perturbation. Present detection methods allow reliable detection of difference of an order of about 3-fold to about 5-fold, but more sensitive methods are expected to be developed.

Preferably, in addition to identifying a perturbation as positive or negative, it is advantageous to determine the magnitude of the perturbation. This can be carried out, as noted above, by calculating the ratio of the emission of the two fluorophores used for differential labeling, or by analogous methods that will be readily apparent to those of skill in the art.

Measurement of Pathway Responses

In one embodiment of the invention, transcript arrays reflecting the transcriptional state of a cell of interest are made by hybridizing a mixture of two differently labeled probes each corresponding (i.e., complementary) to the mRNA of a different cell of interest, to the microarray. According to the present invention, the two cells are of the same type, i.e., of the same species and strain, but may differ genetically at a small number (e.g., one, two, three, or five, preferably one) of loci. Alternatively, they are isogeneic and differ in their environmental history (e.g., exposed to a drug versus not exposed).

In order to measure pathway responses, cells are prepared or grown in the presence of graded perturbations to a pathway of interest. The cells exposed to the perturbation and cells not exposed to the perturbation are used to construct transcript arrays, which are measured to find the mRNAs with modified expression and the degree of modification due to exposure to the drug. Thereby, the pathway response is obtained.

The density of levels of the graded drug exposure and graded perturbation control parameter is governed by the sharpness and structure in the individual gene responses— the steeper the steepest part of the response, the denser the levels needed to properly resolve the response. This exemplary density is approximately indicated by the example of FIG. 3. There, six exposures to methotrexate over a hundred-fold range of concentrations was just sufficient to resolve the gene expression responses. However, more exposures are preferably to more finely represent this pathway.

Further, it is preferable in order to reduce experimental error to reverse the fluorescent labels in two-color differential hybridization experiments to reduce biases peculiar to individual genes or array spot locations. In other words, it is preferable to first measure gene expression with one labeling (e.g., labeling perturbed cells with a first fluorochrome and unperturbed cells with a second fluorochrome) of the mRNA from the two cells being measured, and then to measure gene expression from the two cells with reversed labeling (e.g., labeling perturbed cells with the second fluorochrome and unperturbed cells with the first fluorochrome). Multiple measurements over exposure levels and perturbation control parameter levels provide additional experimental error control. With adequate sampling a trade-off may be made when choosing the width of the spline function S used to interpolate response data between averaging of errors and loss of structure in the response functions. Approximately ten measurements over drug exposure and perturbation control parameter intervals, repeated with reversal of the fluorescent labels, which together require approximately 20 hybridization experiments per drug response or perturbation response, achieve reliable identification of pathways and their member genes and proteins.

Measurement of Drua Response Data

To measure drug response data, the cells are exposed to graded levels of the drug or drug candidate of interest. When the cells are grown in vitro, the compound is usually added to their nutrient medium. In the case of yeast, it is preferable to harvest the yeast in early log phase, since expression patterns are relatively insensitive to time of harvest at that time. The drug is added is a graded amount that depends on the particular characteristics of the drug, but usually will be between about 1 ng/ml and 100 mg/ml. In some cases a drug will be solubilized in a solvent such as DMSO.

The cells exposed to the drug and cells not exposed to the drug are used to construct transcript arrays, which are measured to find the mRNAs with altered expression due to exposure to the drug. Thereby, the drug response is obtained.

Similarly for measurements of pathway responses, it is preferable also for drug responses, in the case of two-color differential hybridization, to measure also with reversed labeling. Also, it is preferable that the levels of drug exposure used proved sufficient resolution (e.g., by using approximately 10 levels of drug exposure) of rapidly changing regions of the drug response.

Other Methods of Transcriptional State Measurement

The transcriptional state of a cell may be measured by other gene expression technologies known in the art. Several such technologies produce pools of restriction fragments of limited complexity for electrophoretic analysis, such as methods combining double restriction enzyme digestion with phasing primers (see, e.g., European Patent 0 534858 A1, filed Sep. 24, 1992, by Zabeau et al.), or methods selecting restriction fragments with sites closest to a defined mRNA end (see, e.g., Prashar et al., 1996, Proc. Natl. Acad. Sci. USA 93:659–663). Other methods statistically sample cDNA pools, such as by sequencing sufficient bases (e.g., 20–50 bases) in each of multiple DNAs to identify each cDNA, or by sequencing short tags (e.g., 9–10 bases) which are generated at known positions relative to a defined mRNA end (see, e.g., Velculescu, 1995, Science 270:484–487).

5.5.2 Measurement of Other Aspects of Biological State

In various embodiments of the present invention, aspects f the biological state other than the transcriptional state, such as the translational state, the activity state, or mixed aspects can be measured in order to obtain drug and pathway responses. Details of these embodiments are described in this section.

Embodiments Based on Translational State Measurements

Measurement of the translational state may be performed according to several methods. For example, whole genome monitoring of protein (i.e., the "proteome," Goffeau et al., supra) can be carried out by constructing a microarray in which binding sites comprise immobilized, preferably monoclonal, antibodies specific to a plurality of protein species encoded by the cell genome. Preferably, antibodies are present for a substantial fraction of the encoded proteins, or at least for those proteins relevant to the action of a drug of interest. Methods for making monoclonal antibodies are well known (see, e.g., Harlow and Lane, 1988, *Antibodies: A Laboratory Manual*, Cold Spring Harbor, N.Y., which is incorporated in its entirety for all purposes). In a preferred embodiment, monoclonal antibodies are raised against synthetic peptide fragments designed based on genomic sequence of the cell. With such an antibody array, proteins from the cell are contacted to the array. and their binding is assayed with assays known in the art.

Alternatively, proteins can be separated by two-dimensional gel electrophoresis systems Two-dimensional gel electrophoresis is well-known in the art and typically involves iso-electric focusing along a first dimension followed by SDS-PAGE electrophoresis along a second dimension. See, e.g., Hames et al, 1990, *Gel Electrophoresis of Proteins: A Practical Approach*, IRL Press, New York; Shevchenko et al., 1996, *Proc. Nat'l Acad. Sci. USA* 93:1440–1445; Sagliocco et al., 1996, *Yeast* 12:1519–1533; Lander, 1996, *Science* 274:536–539. The resulting electropherograms can be analyzed by numerous techniques, including mass spectrometric techniques, western blotting and immunoblot analysis using polyclonal and monoclonal antibodies, and internal and N-terminal micro-sequencing. Using these techniques, it is possible to identify a substantial fraction of all the proteins produced under given physiological conditions, including in cells (e.g., in yeast) exposed to a drug, or in cells modified by, e.g., deletion or over-expression of a specific gene.

Embodiments Based on Other Aspects of the Biological State

Although monitoring cellular constituents other than mRNA abundances currently presents certain technical difficulties not encountered in monitoring mRNAs, it will be apparent to those of skill in the art that the use of methods of this invention, including application of various known methods of pathway perturbation, are applicable to any cellular constituent that can be monitored.

In particular, where activities of proteins relevant to the characterization of drug action can be measured, embodiments of this invention can be based on such measurements. Activity measurements can be performed by any functional, biochemical, or physical means appropriate to the particular activity being characterized. Where the activity involves a chemical transformation, the cellular protein can be contacted with the natural substrate(s), and the rate of transformation measured. Where the activity involves association in multimeric units, for example association of an activated DNA binding complex with DNA, the amount of associated protein or secondary consequences of the association, such as amounts of mRNA transcribed, can be measured. Also, where only a functional activity is known, for example, as in cell cycle control, performance of the function can be observed. However known and measured, the changes in protein activities form the response data analyzed by the foregoing methods of this invention.

In alternative and non-limiting embodiments, response data may be formed of mixed aspects of the biological state of a cell. Response data can be constructed from, e.g., changes in certain mRNA abundances, changes in certain protein abundances, and changes in certain protein activities.

5.6 Applications to Drug Discovery

The present invention has numerous applications in the field of drug discovery, some of which are presented herein. In one application, the present invention provides a method for determining other biological pathway of action of a candidate drug for which a putative pathway of action has already been identified are determined. As noted supra, drug development often involves testing numerous compounds for a specific effect on a known biological pathway, such as a pathway originating at a cloned gene sequence or isolated enzyme or protein. In this process, drug candidates that apparently affect the putative pathway are identified, but little or no information is generated about the specificity of the drug (e.g., what other biological pathways are affected), or about the particular effects of the drug on the affected pathways. The method of the present invention provides this information.

For example, provided with a candidate drug that appears to affect a putative biological pathway, the methods of the present invention can be applied to confirm that the putative pathway is indeed a pathway of action of the drug, as well as for development of drugs (e.g., such as an ideal drug) that are more specific for the putative pathway (i.e., are more pathway-specific) in that they affect fewer biological pathways other than the desired putative pathway. This application can be achieved by direct employment of the -methods described generally in Section 5.2 and specifically in Section 5.3 (especially with reference to FIG. 5). Accordingly, in one aspect, this is achieved by: (i) measuring drug response data for the drug or candidate of interest; (ii) measuring the perturbation response for the putative biological pathway of drug action (e.g., if the biological pathway originates at a gene, then the expression of the gene may be controlled in a graded manner); (iii) representing the drug response data as best as possible in terms of pathway response data for the putative pathway of drug action; and (iv) assessing the significance of the representation to determine whether significant effects of the drug have been fully represented and verifying that the putative pathway is actually a pathway of action of the drug.

If, as is described in more detail supra with respect to step 507, exposing the cell to the drug along with perturbations to the putative pathway results in interfering effects on the response of the cellular constituents of the pathway, then this indicates that the pathway is indeed a pathway of action of the drug. In other words, the combined response is assessed to determine whether it is more like the illustrated in FIG. 7A than that illustrated in FIG. 7B. On the other hand, if the effects of combined exposure are primarily additive (like that illustrated in FIG. 7B), then this indicates that the putative pathway is not a pathway of drug action. Further, if, as is described in more detail supra with respect to step 506, the best representation of the drug response data by the pathway response data is found to be highly significant, for example, by surpassing a 95% significance threshold, then this indicates that the candidate drug is highly specific for the putative biological pathway (with few or no direct effects on other biological pathways, such as those originating at other genes, or gene products, or gene product activities). On the other hand, if this representation is found to be not sufficiently significant, then this indicates that other biological pathways are affected by the drug or candidate of interest.

In the latter case, in which other biological pathways in the cell are affected, the structure of the candidate drug may be modified (e.g., using organic synthesis methods well known in the arts of pharmaceutical or medicinal chemistry) or closely related compounds may be identified, or the like, and tested according to the present invention until a drug that is more pathway-specific (i.e., affecting fewer pathways other than the putative pathway) for the putative pathway (or even an ideal drug affecting only the putative pathway) is identified.

In another application, the methods of this invention can be used to select, from a set of candidate compounds, the drug or drugs with the highest pathway specificity by identifying all the cellular biological pathways of compounds in the set. Usually, the drug with the highest pathway specificity will be the one that directly affects only its intended pathway. When the intended pathway is not known, the drug that affects the fewest number of pathways is likely to be more pathway-specific than a drug that affects a greater number of pathways, and is a preferred candidate. A drug with high specificity (i.e., highly pathway-specific) is of interest because such a drug will likely have fewer side effects when administered to a patient.

In further applications, the invention can be used to identify the pathway(s) of action a drug that has a known biological effect on cells (or on patients), but for which the mechanism or pathway of action is not known. By identifying the pathway of action of a drug with a desirable therapeutic activity it is possible to identify other compounds having a similar therapeutic activity, as well as to identify compounds with greater pathway specificity. In such an application, the drug response data is fit with a combination of pathways likely to be affected by the drug, or with pathways simply drawn from a compendium of pathways, and the pathway combination best fitting the drug response determined. Conversely, the methods of this invention can be used to identify a compound or compounds that affect a particular pre-determined biological pathway in a cell, or that affect a particular combination of pathways. In such an application, the significance of the best fit of the drug response data to the pathway response data (or combination of pathway response data) is determined to see if it meets a certain threshold of significance.

In yet a further application, the method is used to identify "secondary drug loci." Secondary drug loci are cellular constituents of any type (such as genes or gene products or gene product activities), that are indirectly affected by the administration of a drug. They are identified by the fact that they correspond to cellular constituents having positive or negative perturbations in the pathway response data, but are not directly affected by the drug. For example, secondary drug loci include cellular constituents in a biological pathway originating at a directly-affected target of the drug (excluding the originating directly-affected target cellular constituent). The identification of secondary drug loci is useful in drug design. As discussed above, the homeostatic mechanisms of the cell usually assure that a change in one cellular constituent (e.g., gene, or gene product, or gene product activity) is compensated for by changes in the expression and/or activity of other cellular constituents. Recognition of these compensatory changes provides a new approach to drug intervention, as follows: Disease can often be considered the result of abnormal activation of biological pathway as a result of abnormal expression of a cellular constituent originating that pathway (e.g., a gene of a host or a pathogen). Conventional approaches to drug intervention seek to modulate the abnormal pathway activity by acting at this primary originating cellular constituent. However, the present method identifies secondary drug loci, which are cellular constituents, such as genes or gene products, that a drug indirectly affects (e.g., by being part of an affected biological pathway) when a pathway is directly affected. Using this information, it is possible to identify drugs that affect the secondary cellular constituents, providing alternative approaches to treatment (and a much greater array of potential pathways for drug action).

For example, if in a diseased state cellular constituent X is under-expressed, the conventional goal of therapy is to restore the expression of X, and drugs may be identified that achieve this result by directly affecting the expression of X. However, the present method allows identification of other cellular constituents having X as a secondary drug loci, that is these other cellular constituents originate pathways including X that are also affected by the action of the drug. Corrected expression of element X will thereby result from the action of a drug on such pathways. Thus, secondary pathways (e.g., those originating at proteins, or at protein activities) that produce desired therapeutic outcomes if inhibited or activated can be identified, and drugs can be identified that affect these other pathways to achieve the desired therapeutic outcome (e.g., restoring the expression of X), other than by direct effects on X.

In additional applications, the methods of this invention can be used to identify biological pathways that mediate the therapeutic actions or that mediate the side-effects of a drug of interest by comparison of the drug of interest with other drugs having similar therapeutic effects. Two drugs are considered to have similar therapeutic effects if they both exhibit similar therapeutic efficacy for the same disease of disorder in a patient or in an animal disease model. Drugs known to have similar, or closely similar, therapeutic affects are often found to act on the same biological pathways. Therefore, the methods of this invention can be applied to determine the pathways affected by the drug of interest and also of a second drug with similar therapeutic effects. Pathways that are common to both drugs are those pathways likely to mediate the therapeutic effects of the drug of interest (and also of the second drug). By comparing common pathways determined for additional drugs with similar therapeutic effects, the pathways mediating the therapeutic effects of the drug of interest can be further narrowed or identified.

Similarly, pathways affected by a drug that mediate the side-effects can be determined by the methods of this invention. The pathways affected by the drug of interest and of a second drug with a similar therapeutic effects are determined according to this invention. The pathways of the drug of interest that are not also pathways of the second drug are likely to be those mediating the side-effects of the drug of interest. By comparing common pathways determined for additional drugs with similar therapeutic effects, pathways mediating the side-effects of the drug of interest effects can be more certainly identified. Optionally, a more pathway-specific derivative of the drug of interest can be identified by next applying the previous described steps for improving the specificity of the drug of interest in order to eliminate the pathways mediating side-effects.

When the cell employed in the methods of this invention is a non-human eukaryotic cell, e.g., a yeast cell, it is often possible to extrapolate from the effects of the drug in the non-human cell to the effect in the human cell. This is due, in part, to the fact that a large proportion of genes have homologous counterparts of similar function in most eukaryotes. As noted above, almost half of the proteins identified as defective in human heritable diseases show amino acid similarity to yeast proteins. It has also been reported that about 80% of all genes known to cause human disease have homologs in *C. elegans* ("Experts gather to discuss technologies being developed for functional genomic analysis," *Genetic Engineering News:*16, Nov. 15, 1996).

In yet additional applications, the methods of the present invention can be used to ascertain the similarity of the effects of different drugs. This application corresponds to the particular case wherein the number of pathways scaled to fit the drug response data is equal to unity, i.e., to one. Thus, in the particular embodiment, R denotes the response of the "perturbation" drug, referred to herein as Drug R, which is being compared to the response, D, generated by the first drug, referred to herein as Drug D. The correlation coefficient obtained from Eqns. 8 and 9, or, alternatively, the least-squares residual obtained from Eqn. 6, provides a quantitative measure of similarity of the effects of the two drugs.

This method of comparing drug responses is significantly superior to correlations based on single-concentration measurements, for the following reason. The two drugs in question, Drugs D and R, may have the same pathway of action but at different potencies. A measurement at one concentration therefore will sample the drug response curves, such as the those illustrated in FIG. 2A, at only one titration level. In general, the titration level corresponding to a given concentration of Drug D will be different from the titration level corresponding to the same concentration of Drug R. For example, the measurement of Drug D may correspond to Titration level 1 in FIG. 2A, whereas the measurement of Drug R may correspond to Titration level 4. Changes in only genes G1 and G2 will therefore be observed for Drug D, while changes in all of the genes G1–G6 will be observed for Drug R. Consequently, the similarity of the responses of Drugs D and R will not be as readily apparent as if the entire response curve from zero concentration to saturation is sampled for both Drug D and Drug R, and the best correlation found via the scaling transformation as described in Section 5.3.1, above.

Such a superior measure of drug similarity may be the basis, e.g., for the classification of new compounds into classes defined by existing compounds, including recognizing probable therapeutic or toxic effects based on this classification. Such a superior measure of drug similarity may also be the basis for the grouping of new or existing compounds so as to reduce redundancy of libraries or lists of compounds, or to support decisions about what screening or other action to take with a particular compound.

6 EXAMPLES

The following example of pathway perturbations by such drugs of known specific actions is presented by way of illustration of the previously described invention and are not limiting of that description. In this example, pathways are defined by the graded exposure of a cell to cyclosporin A ("CyA") and to methotrexate ("Mtx") and the pathway of action of an "unknown" drug, herein FK506, is determined.

By way of background, CyA acts directly to inhibit calcineurin, and can be used to define the pathway originating at calcineurin. Mtx acts directly to inhibit the DHFR (dihydrofolate reductase) protein, and can also be used to define the pathway originating at this protein. FK506 is also a specific regulator of the calcineurin protein, on which it acts via a complex with an FK506 binding protein (Cardenas et al., 1994, Yeast as model T cells, Perspectives in Drug Discovery and Design 2:103–126).

Figure 8A:
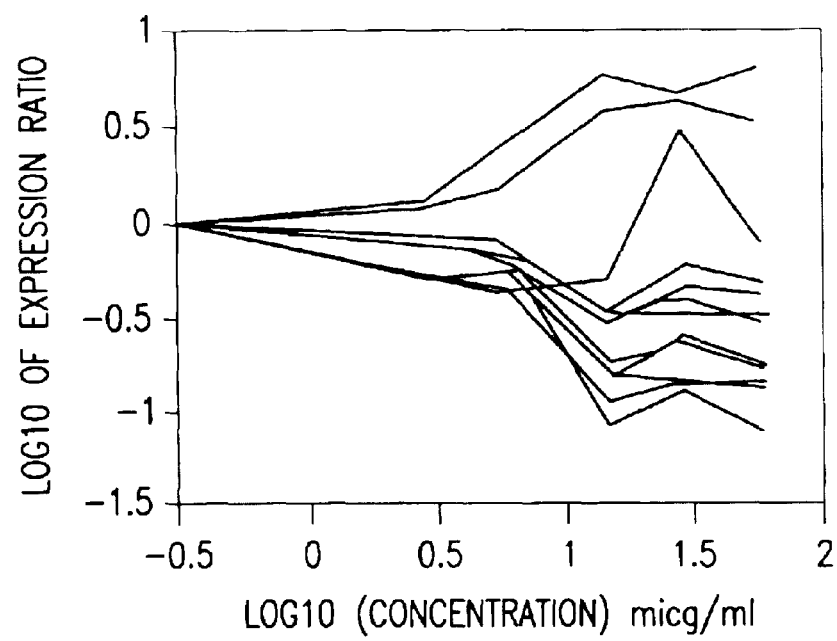
FIGS. 8A-C illustrate response curves of the yeast genes that had the largest expression ratio changes to exposure to the drugs cyclosporin A, methotrexate, and FK506, respectively.
Figure 8B:
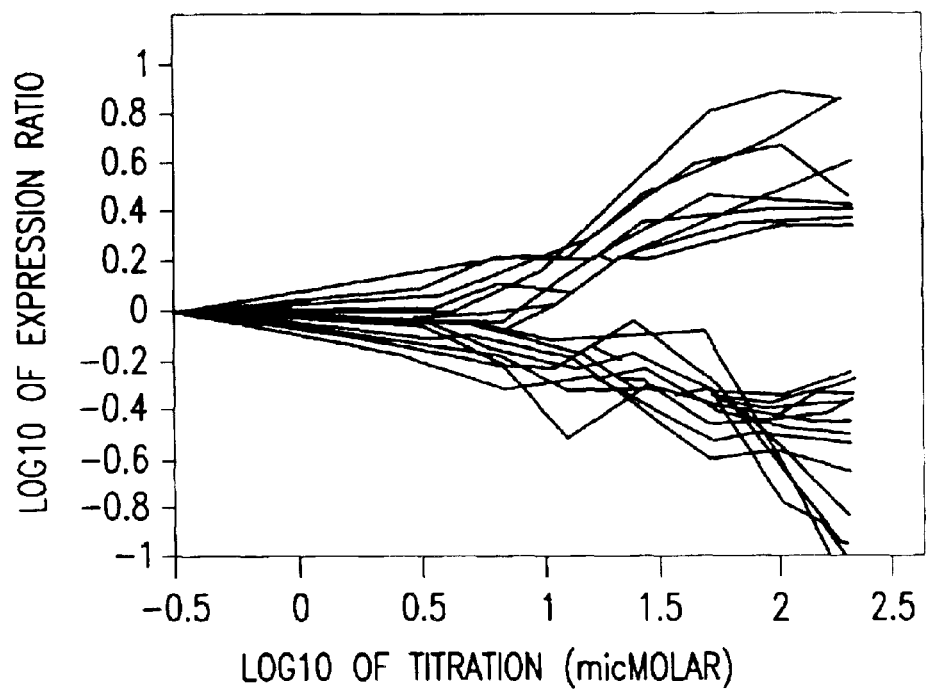
Figure 8C:
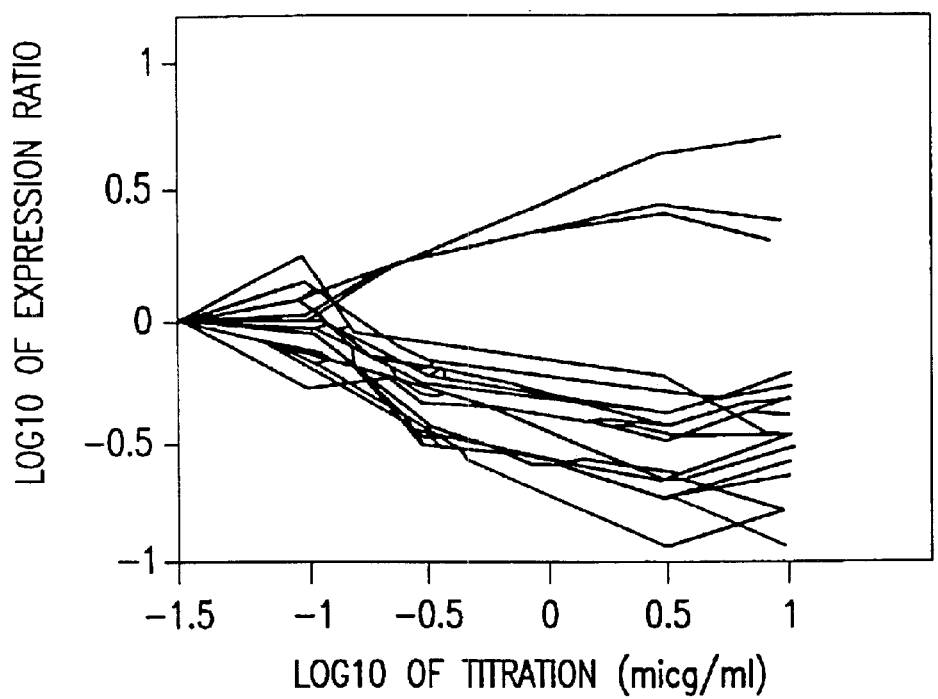

The gene expression measurements illustrated in FIGS. 8A-C were made as detailed below. To generate the cyclosporin dose response curves, an overnight starter culture of *S.cerevisiae* strain R563 (Genotype: Mat a ura3-52 lys2-801 ade2-101 trpl-Δ63 his3-Δ200 leu2-Δ1 his3::HIS3) was diluted into 200 ml of YAPD plus 10 mM $CaCl_2$ medium (see, e.g., Ausubel et al., eds., 1996, *Current Protocols in Molecular Biology*, John Wiley & Sons, Inc., especially ch. 13) to an $OD_{600}$ of 0.1 and grown at 30° C. with 300 rpm shaking. After a 30 min, cyclosporin A dissolved in ethanol was added to cultures at final concentrations of 60, 30, 15, 6 and 3 μg/ml. Control cultures were treated with the same volume of just ethanol. Growth was monitored by $OD_{600}$ and cells were harvested at $OD_{600}$= 1.4+/−0.1 by centrifugation for 2 min at ambient temperature in a Sorvall RC5C+centrifuge in a SLA-1500 rotor. The supernatant was discarded, the residual liquid removed by pipetting, and the cells were resuspended in 4 ml RNA Extraction Buffer (0.2 M Tris HCl pH 7.6, 0.5 M NaCl, 10 mM EDTA, 1% SDS). Cells were vortexed for 3 sec to resuspend the pellet and then immediately transferred to 50 ml conical centrifuge tubes containing 2.5 g baked glass beads (425–600 μm) and 4 ml phenol:chloroform (50:50 v/v). Tubes were vortexed for 2 min in the VWR Multi-tube Vortexer at setting 8 prior to centrifugation at 3000 rpm for 5 min at ambient temperature in a Sorvall Model T600D tabletop centrifuge to separate the phases. The aqueous phase was reextracted with equal volume of phenol:chloroform (50:50 v/v) by vortexing for 30 sec at setting 6 followed by centrifugation as before. To the aqueous phase was added 2.5 volumes of ethanol and the samples were stored at −80° C. until isolation of polyA+mRNA.

To generate FK506 dose response curves, the above procedure was followed except that FK506 dissolved in ethanol was added to cultures at final concentrations of 10, 3.1, 1.0, 0.31, 0.10 μg/ml.

To generate methotrexate dose response curves, an overnight starter culture of *S.cerevisiae* strain BY4741 (Genotype: Mat a his3Δ0 leu2D0 ura3Δ0 met15Δ0) was diluted into 200 ml of SC medium (see, e.g., Ausubel et al, ch. 13) to an $OD_{600}$ of 0.1 and grown at 30° C. with 300 rpm shaking. After 30 min, methotrexate dissolved in water was added to cultures at final concentrations of 200, 100, 50, 25, 6.2, and 3.1 μM. Control cultures were treated with the same volume of water. The rest of the procedure was as above.

In all cases, polyA+ RNA was isolated by oligo-dT cellulose chromatography using two selections by standard protocols (see, e.g., Sambrook et al. 1989, *Molecular Cloning A Laboratory Manual*, Cold Spring Harbor Laboratory Press). Two micrograms of polyA+ RNA was used in reverse transcription reactions as previously described in Section 5.5.1. cDNA was purified and hybridized to polylysine slides as also previously described in Section 5.5.1. Extent of hybridization was determined by scanning with a prototype multi-frame CCD camera slides produced by Applied Precision, Inc. Images were processed by informatics and imported into the Inpharma database and analyzed using the MatLab data analysis package.

FIG. 5c illustrates the drug response data generated by a series of FK506 exposures. This figure has values of the drug exposure on the horizontal axis, and values of the logarithm of the expression ratio of the genes most affected by FK506 on the vertical axis. FIG. 8A illustrates the pathway response data for the pathway originating at the calcineurin protein and generated by a series of CyA exposures. This figure and FIG. 8B have values of the pathway perturbation control parameter, which is in this case the level of drug exposure, on the horizontal axis, and values of the logarithm of the expression ratio of the genes most affected by these drugs on the vertical axis. FIG. 8B illustrates the pathway response data for the pathway originating at the DHFR (dihydrofolate reductase) protein and generated by a series of Mtx exposures.

Figure 8D:
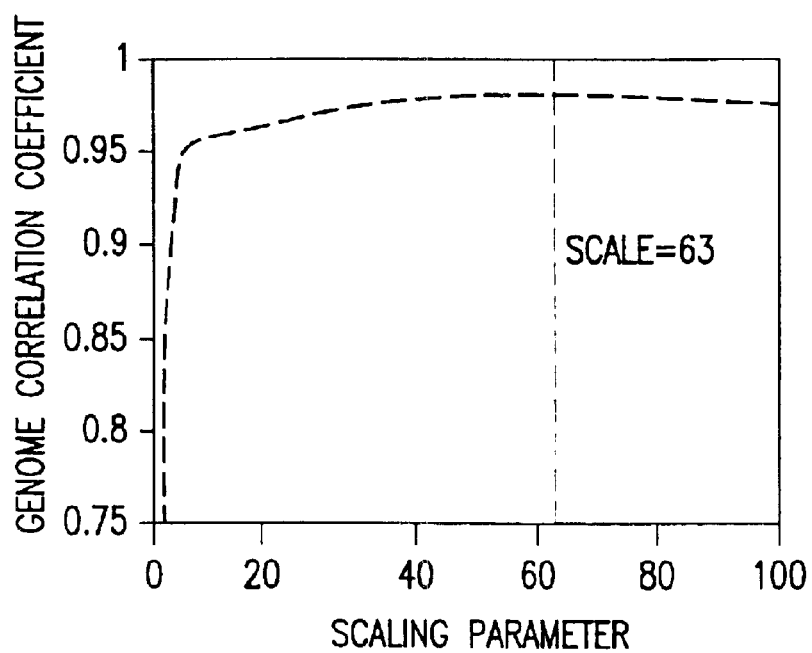

Fk506, the "unknown" drug, is modeled with a linear sum of the measured pathway responses resulting from graded exposures to CyA or Mtx (separately exposed), forming a composite response involving at least pathways originating at calcineurin and at DHFR. FIG. 8D shows a graph of the correlation coefficient, which is obtained by genome-wide correlation of the FK506 responses against the combined pathway responses of Cyc A and Methotrexate, against different values of the scaling parameter that was applied to the FK506 data. The correlation coefficient was obtained according to the methods outlined in Section 5.3.1, in particular according to Eqns. 8 and 9. The approximate relative potency of FK506 and Cyc A, which was approximately 63, was recovered as the location of the correlation peak illustrated in FIG. 5D.

Table I lists the set of genes common to FK506 and Cyc A responses. These genes were identified as those genes having a correlation coefficient between the drug and pathway response curves for that gene of at least 0.9 at the value of scaling parameter (63), which gave the maximum genome-wide correlation. These correlation coefficients were computed as $p_k(63)$ according to Eqn. 9, where the index "k" corresponds to a particular gene. These correlated genes were the same whether or not the Mtx pathway response is added to the minimization, illustrating the ability to identify a pathway within a composite response.

TABLE I

| With Methotrexate | Without Methotrexate |
|---|---|
| gyp7 | gyp7 |
| YJL171C | YJL171C |
| CMK2 | CMK2 |
| YRO2 | YRO2 |
| RIM101 | RIM101 |
| YKL218C | YKL218C |
| YLR414C | YLR414C |
| YDR425W | YDR425W |
| YNL195C | YNL195C |
| YOR385W | YOR385W |
| YOR220W | YOR220W |
| HAC1 | HAC1 |
| YLR121C | YLR121C |
| hxk1 | hxk1 |
| YHR097C | YHR097C |
| SUR1 | SUR1 |
| CWP1 | CWP1 |
| YBR005W | YBR005W |
| yap3 | yap3 |
| YMR316W | YMR316W |
| YBR004C | YBR004C |

This example illustrated the usefulness of the methods of this invention in that a maximum value of the scaling parameter and consistent sets of identified genes were easily identified.

In this experiment Cyc A and Methotrexate responses were added linearly for the purposes of the numerical analysis (as previously described) In case of actual simultaneous exposure to both drugs non-linear terms may need to be added to the model drug responses.

7 REFERENCES CITED

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A computer system for determining a representation of measured drug response of a cell type to a drug in terms of one or more biological pathway responses, said computer system comprising a processor and a memory coupled to said processor, said memory encoding one or more programs, said one or more programs causing said processor to perform a method comprising the steps of:

(a) receiving a drug response of said drug in said cell type, said drug response comprising quantitative measurements of a plurality of cellular constituents in a cell of said cell type at a plurality of levels of drug exposure;

(b) receiving one or more biological pathway responses, each of said one or more biological pathway responses comprising quantitative measurements of cellular constituents of a biological pathway in a cell of said cell type at a plurality of levels of a perturbation to said biological pathway, said one or more biological pathway responses comprising at least one biological pathway response from a biological pathway that is likely to be involved in action of said drug in said cell type;

(c) forming a model drug response as a combination of said one or more biological pathway responses, wherein each of said one or more biological pathway responses in said combination is subject to an independent scaling transformation;

(d) determining the value of a function of the difference between said drug response and said model drug response; and (e) minimizing said determined value of said function by varying the scaling transformations of said one or more biological pathway responses to obtain scaling transformations that minimize said determined value of said function;

wherein said combination of said one or more biological pathway responses subject to said scaling transformations is a representation of said measured drug response of said cell type to said drug.

2. The computer system of claim 1 wherein said steps of receiving comprise making said drug response and said biological pathway responses available in said memory.

3. The computer system of claim 1 wherein said forming a model drug response comprises adding said one or more biological pathway responses.

4. The computer system of claim 1 wherein said function comprises a sum of squares of the differences of said drug response and said model drug response at said levels of drug exposure, said model drug response being provided at said levels of drug exposure by transforming by said scaling transformations said levels of drug exposure to corresponding levels of perturbations to each of said biological pathways and by interpolating said biological pathway responses to said corresponding levels of perturbations.

5. The computer system of claim 1 wherein the method performed by said processor further comprises the steps of:
(f) determining an expected probability distribution of minimized determined values of said function, and
(g) assessing the statistical significance of the minimized determined value of said function in view of the expected probability distribution of minimized determined values of said function.

6. The computer system of claim 5 wherein the expected probability distribution of minimized determined values of said function is determined by:
(i) randomizing the drug response with respect to the plurality of levels of drug exposure or randomizing the model drug response by randomizing the one or more biological pathway responses with respect to the plurality of levels of perturbation to the one or more biological pathways;
(ii) determining a theoretical minimum value of the function by a method comprising:
determining scaling transformations of the one or more randomized biological pathway responses which minimize the function of the difference between the drug response and the randomized model drug response, if the one or more biological pathway responses are randomized, or determining scaling transformations of the one or more biological pathway responses which minimize the function of the difference between the randomized drug response and the model drug response, if the drug response is randomized; and
(iii) repeating steps (i) through (ii) to determine a plurality of theoretical minimum values, wherein said plurality of minimum values forms said expected probability distribution of minimized values.

7. The computer system of claim 1 wherein the method performed by the processor further comprises a step of verifying that said representation of said drug response is a representation of said drug response of said cell type to said drug by a method comprising selecting a model response that behaves most similarly to a combined drug-perturbation response, said combined drug perturbation response being provided by a method comprising quantitatively measuring a plurality of cellular constituents in a cell of said cell type exposed simultaneously to one or more levels of said exposure to said drug and to one or more levels of perturbations in said one or more biological pathways,
wherein the model drug response is selected from the group consisting of:
(i) a first model drug response comprising the combination of one or more biological pathway responses subject to the scaling transformations evaluated at one or more first sums, each first sum being the sum of one of said one or more levels of drug exposure subject to said scaling transformations and one of said one or more levels of perturbations to said biological pathways.
(ii) a second model drug response comprising one or more second sums, each second sum being the sum of said drug response evaluated at one of said one or more levels of drug exposure and said combination of said one or more biological pathway responses subject to the scaling transformations evaluated at one of said one or more levels of perturbations to said biological pathways,
wherein said representation is verified as a representation of said drug response of said cell type to said drug if the first model response is selected.

8. The computer system of claim 1 wherein the method performed by the processor further comprises a step of assigning a cellular constituent present in said drug response to the one of said one or more biological pathways in which the biological pathway response of the cellular constituent subject to its scaling transformation has the greatest correlation with the drug response of the cellular constituent.

9. The computer system of claim 1 wherein said scaling transformations comprise transformations of said levels of drug exposure to corresponding levels of said perturbations to said biological pathways.

10. The computer system of claim 2 wherein said transformations of said levels of drug exposure are by linear mapping.

11. The computer system of claim 1 wherein said one or more programs further cause said processor to interpolate the quantitative measurements of cellular constituents of the biological pathway in said cell of said cell type at a plurality of levels of perturbation so that the one or more biological pathway responses are interpolated.

12. The computer system of claim 11 wherein the interpolating comprises approximation by a sum of spline functions.

13. The computer system of claim 11 wherein the interpolating comprises approximation by a Hill function.

14. The computer system of claim 1 wherein the one or more biological pathways in the cell type are those biological pathways likely to be involved in the action of the drug in the cell type.

15. The computer system of claim 1 wherein the one or more biological pathways are selected from a compendium of biological pathways present in the cell type.

16. The computer system of claim 1 wherein the cell type is substantially isogeneic to *Saccharomyces cerevisiae*.

17. The computer system of claim 1 wherein the cellular constituents comprise abundances of a plurality of RNA species present in the cell type.

18. The computer system of claim 17 wherein the abundances of the plurality of RNA species are measured by a method comprising contacting a gene transcript array with RNA from a cell of the cell type, or with cDNA derived therefrom, wherein a gene transcript array comprises a surface with attached nucleic acids or nucleic acid mimics, said nucleic acids or nucleic acid mimics being capable of hybridizing with said plurality of RNA species or with cDNA species derived therefrom.

19. The computer system of claim 18 wherein the quantitative measurements of cellular constituents in step (a) are provided by a method comprising contacting one or more gene transcript arrays (i) with RNA, or with cDNA derived therefrom, from a cell of said cell type that is exposed to said drug, and (ii) with RNA, or with cDNA derived therefrom, from a cell of said cell type that is not exposed to said drug, and
wherein said quantitative measurements of cellular constituents in step (b) are provided by a method comprising contacting one or more gene transcript arrays (i) with RNA, or with cDNA derived therefrom, from a cell of said cell type that is exposed to said perturbation to said biological pathway, and (ii) with RNA, or with cDNA derived therefrom, from a cell of said cell type that is not exposed to said perturbation to said biological pathway.

20. The computer system of claim 1 wherein the cellular constituents comprise abundances of a plurality of protein species present in the cell type.

21. The computer system of claim 20 wherein the abundances of the plurality of protein species are measured by a method comprising contacting an antibody array with proteins from a cell of the cell type, wherein the antibody array comprises a surface with attached antibodies that are capable of binding with the plurality of protein species.

22. The computer system of claim 20 wherein the abundances of the plurality of protein species are measured by a method comprising performing two-dimensional electrophoresis of proteins from a cell of the cell type.

23. The computer system of claim 1 wherein the cellular constituent comprise activities of a plurality of protein species present in the cell type.

24. The computer system of claim 1 wherein the one or more biological pathways in the cell type comprise biological pathways originating at one or more specific cellular constituents, and wherein the perturbations to the biological pathways are performed by a method comprising modifying the one or more specific cellular constituents.

25. The computer system of claim 24 wherein the one or more specific cellular constituents are modified by a method comprising causing expression of the one or more specific cellular constituents under the control of a controllable expression system.

26. The computer system of claim 24 wherein the one or more specific cellular constituents are modified by a method comprising controllable transfection of genes expressing the one or more specific cellular constituents.

27. The computer system of claim 24 wherein the one or more specific cellular constituents are modified by a method comprising controllably decreasing abundances of RNA species encoding the one or more specific cellular constituents in a cell of the cell type.

28. The computer system of claim 27 wherein the method of controllable decreasing abundances of RNA species comprises exposing a cell of the cell type to ribozymes targeted to cleave the RNA species.

29. The computer system of claim 24 wherein the one or more specific cellular constituents are modified by a method comprising controllably decreasing the rate of translation of RNA species encoding the one or more specific cellular constituents in a cell of the cell type.

30. The computer system of claim 29 wherein the method of controllably decreasing the rate of translation of RNA species comprises exposing a cell of the cell type to antisense nucleic acids or antisense nucleic acid mimics that hybridize to the RNA species or to DNA encoding the RNA species.

31. The computer system of claim 24 wherein the one or more specific cellular constituents are abundances of protein species or activities of protein species, and wherein the one or more specific cellular constituents are modified by a method comprising controllably decreasing the abundances in a cell of the cell type.

32. The computer system of claim 31 wherein the method of controllably decreasing the abundances comprises causing expression in a cell of the cell type of the one or more protein species as fusion proteins comprising the protein species and a degron, wherein the degron is controllable to increase the rate of degradation of the protein species.

33. The computer system of claim 31 wherein the method of controllably decreasing the abundances comprises exposing a cell of the cell type to antibodies, wherein the antibodies bind to the protein species.

34. The computer system of claim 24 wherein the one or more specific cellular constituents are activities of protein species, and wherein the one or more specific cellular constituents are modified by a method comprising controllably decreasing the activities in a cell of the cell type.

35. The computer system of claim 34 wherein the method of controllably decreasing the activities comprises exposing a cell of the cell type to drugs which directly and specifically inhibit the activities of the protein species.

36. The computer system of claim 34 wherein the method of controllably decreasing the activities comprises exposing a cell of the cell type to dominant negative mutant protein species, wherein the dominant negative mutant protein species are proteins inhibiting said activities.

37. A computer system for determining a representation of measured drug response of a cell type to a drug in terms of one or more biological pathway responses, comprising a processor, and a memory coupled to said processor and encoding one or more programs, wherein said one or more programs cause said processor to perform a method that comprises determining the scaling transformation of one or more biological pathway responses which minimize the value of a function of the difference between a provided drug response and a model drug response, wherein:

(a) said one or more biological pathway responses are the product of a method comprising quantitatively measuring cellular constituents of one or more biological pathways in a cell of said cell type at a plurality of levels of perturbation to said biological pathways, said one or more biological pathway responses comprising at least one biological pathway response from a biological pathway that is likely to be involved in action of said drug in said cell type;

(b) said provided drug response is provided by a method comprising quantitatively measuring a plurality of cellular constituents in a cell of the cell type at a plurality of levels of exposure to said drug; and (c) said model drug response is represented as a combination of said one or more biological pathway responses, each of said one or more biological pathway responses in said combination being subject to an independent scaling transformation; and wherein the combination of said one or more biological pathway responses subject to said scaling transformations is a representation of said measured drug response of said cell type to said drug.

38. The computer system of claim 37 wherein said computer system assigns a statistical significance to the combination of said one or more biological pathway responses subject to said scaling transformations, wherein the statistical significance is assigned by a method comprising:

(a) obtaining an expected probability distribution of minimized values of the function; and (b) assessing statistical significance of an actual minimized value of the function in view of the expected probability distribution, wherein the actual minimized value of the function is determined from the provided drug response and the model drug response.

39. The computer system of claim 38 wherein the expected probability distribution is obtained by a method comprising:

(a) randomizing the drug response with respect to the plurality of levels of drug exposure, or, randomizing the model drug response by a method comprising randomizing the one or more biological pathway responses with respect to the plurality of levels of perturbation to the one or more biological pathways;

(b) determining a theoretical minimum value of the function by a method comprising:

determining scaling transformations of the one or more randomized biological pathway responses which minimize the function of the difference between the drug response and the randomized model drug response, if the one or more biological pathway responses are randomized, or determining scaling transformations of the one or more biological pathway responses which minimize the function of the difference between the randomized drug response and the model drug response, if the drug response is randomized; and (c) repeating steps (a) through (b), so that a plurality of theoretical minimum values is thereby determined, wherein the plurality of theoretical minimum values forms the expected probability distribution.

41. A computer system for determining a representation of measured environmental response of a cell type to an environmental change in terms of one or more biological pathway responses, said computer system comprising:

a processor, and a memory coupled to said processor and encoding one or more programs, a memory coupled to said processor and encoding one or more programs, wherein said one or more programs cause said processor to perform a method that comprises determining the scaling transformation of one or more biological pathway responses which minimize the value of an objective function of the difference between a received environmental response and a model environmental response, wherein:

(a) said one or more biological pathway responses are the product of a method comprising quantitatively measuring cellular constituents of one or more biological pathways in a cell of said cell type at a plurality of levels of perturbation to said biological pathways, said one or more biological pathway responses comprising at least one biological pathway response from a biological pathway that is likely to be involved in effect of said environmental change on said cell;

(b) said received environmental response is provided by a method comprising quantitatively measuring a plurality of cellular constituents in a cell of the cell type at a plurality of levels of exposure to said environmental change; and (c) said model environmental response is represented as a combination of said one or more biological pathway responses, each of said one or more biological pathway responses in said combination being subject to an independent scaling transformation; and wherein the combination of said one or more biological pathway responses subject to said scaling transformations is a representation of said measured environmental response of said cell type to said environmental change.

41. A computer system for determining a representation of measured environmental response of a cell type to an environmental change in terms of one or more biological pathway responses, said computer system comprising:

a processor, and a memory coupled to said processor and encoding one or more programs, wherein said one or more programs cause said processor to perform a method comprising the steps of:

(a) receiving an environmental response to said environmental change upon said cell type, said environmental response comprising quantitative measurements of a plurality of cellular constituents in a cell of said cell type at a plurality of levels of exposure to said environmental change;

(b) receiving one or more biological pathway responses, each of said one or more biological pathway responses comprising quantitative measurements of cellular constituents of a biological pathway in a cell of said cell type at a plurality of levels of a perturbation to said biological pathway, said one or more biological pathway responses comprising at least one biological pathway response from a biological pathway that is likely to be involved in effect of said environmental change on said cell;

(c) forming a model environmental response as a combination of said one or more biological pathway responses, wherein each of said one or more biological pathway responses in said combination is subject to an independent scaling transformation;

(d) determining the value of a function of the difference between said environmental response and said model environmental response; and (e) minimizing said determined value of said function by varying the scaling transformation of said one or more biological pathway responses to obtain scaling transformations that minimize said determined value of said function;

wherein said combination of said one or more biological pathway responses subject to said scaling transformations is a representation of said measured environmental response of said cell type to said environmental change.

* * * * *